US011739065B2

(12) United States Patent
Blomgren et al.

(10) Patent No.: US 11,739,065 B2
(45) Date of Patent: *Aug. 29, 2023

(54) FXR (NR1H4) MODULATING COMPOUNDS

(71) Applicant: Gilead Sciences, Inc., Foster City, CA (US)

(72) Inventors: Peter A. Blomgren, Issaquah, WA (US); Kevin S. Currie, North Bend, WA (US); Christian Gege, Ehingen (DE); Jeffrey E. Kropf, Issaquah, WA (US); Jianjun Xu, Bellevue, WA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/537,250

(22) Filed: Nov. 29, 2021

(65) Prior Publication Data

US 2022/0204460 A1 Jun. 30, 2022

Related U.S. Application Data

(63) Continuation of application No. 17/217,781, filed on Mar. 30, 2021, now abandoned, which is a continuation of application No. 16/989,335, filed on Aug. 10, 2020, now Pat. No. 10,981,881, which is a continuation of application No. 16/541,073, filed on Aug. 14, 2019, now Pat. No. 10,774,054, which is a continuation of application No. 15/618,666, filed on Jun. 9, 2017, now Pat. No. 10,421,730.

(60) Provisional application No. 62/349,490, filed on Jun. 13, 2016.

(51) Int. Cl.
| | |
|---|---|
| *C07D 261/10* | (2006.01) |
| *C07D 401/14* | (2006.01) |
| *C07D 413/12* | (2006.01) |
| *C07D 413/14* | (2006.01) |
| *A61K 31/42* | (2006.01) |
| *A61K 31/44* | (2006.01) |
| *C07C 13/04* | (2006.01) |
| *C07C 25/13* | (2006.01) |
| *C07C 39/28* | (2006.01) |
| *C07D 205/02* | (2006.01) |

(52) U.S. Cl.
CPC ............ *C07D 261/10* (2013.01); *A61K 31/42* (2013.01); *A61K 31/44* (2013.01); *C07C 13/04* (2013.01); *C07C 25/13* (2013.01); *C07C 39/28* (2013.01); *C07D 205/02* (2013.01); *C07D 401/14* (2013.01); *C07D 413/12* (2013.01); *C07D 413/14* (2013.01)

(58) Field of Classification Search
CPC .............................. C07D 261/10; A61K 31/42
See application file for complete search history.

(56) References Cited

U.S. PATENT DOCUMENTS

| | | | |
|---|---|---|---|
| 4,943,584 | A | 7/1990 | Theobald et al. |
| 5,256,666 | A | 10/1993 | Mueller et al. |
| 5,258,551 | A | 11/1993 | Murabayashi et al. |
| 5,502,252 | A | 3/1996 | Takase et al. |
| 5,633,272 | A | 5/1997 | Talley et al. |
| 5,849,746 | A | 12/1998 | Chambers et al. |
| 5,854,268 | A | 12/1998 | Baker et al. |
| 5,912,243 | A | 6/1999 | Dowling et al. |
| 6,407,140 | B1 | 6/2002 | Gregory et al. |
| 6,974,830 | B2 | 12/2005 | Bauer et al. |
| 7,034,046 | B2 | 4/2006 | Bauer et al. |
| 7,098,336 | B2 | 8/2006 | Bauer et al. |
| 7,560,551 | B2 | 7/2009 | Cee et al. |
| 8,188,080 | B2 | 5/2012 | Mustelin et al. |
| 8,193,192 | B2 | 6/2012 | Kremoser et al. |
| 8,222,256 | B2 | 7/2012 | Zhang |
| 8,952,042 | B2 | 2/2015 | Kremoser et al. |
| 9,139,539 | B2 | 9/2015 | Kinzel et al. |
| 9,539,244 | B2 | 1/2017 | Kinzel et al. |
| 9,751,874 | B2 | 9/2017 | Gege et al. |
| 9,820,979 | B2 | 11/2017 | Kinzel et al. |
| 9,855,249 | B2 | 1/2018 | Cole et al. |
| 9,938,278 | B2 | 4/2018 | Gege et al. |
| 10,220,027 | B2 | 3/2019 | Kinzel et al. |
| 10,485,795 | B2 | 11/2019 | Kinzel et al. |
| 10,981,881 | B2 | 4/2021 | Blomgren et al. |
| 2003/0130296 | A1 | 7/2003 | Bauer et al. |
| 2003/0149087 | A1 | 8/2003 | Bauer et al. |
| 2003/0187042 | A1 | 10/2003 | Bauer et al. |
| 2004/0048908 | A1 | 3/2004 | Momose et al. |

(Continued)

FOREIGN PATENT DOCUMENTS

| | | |
|---|---|---|
| CA | 1145344 | 4/1983 |
| CN | 104045635 | 9/2014 |

(Continued)

OTHER PUBLICATIONS

Abel et al., (2010) "Synthesis and pharmacological validation of a novel series of non-steroidal FXR agonists", Bioorganic & Medicinal Chemistry Letters 20: 4911-4917.

(Continued)

*Primary Examiner* — Kamal A Saeed

(74) *Attorney, Agent, or Firm* — Sheppard Mullin Richter & Hampton LLP

(57) ABSTRACT

The present disclosure relates generally to compounds which bind to the NR1H4 receptor (FXR) and act as agonists of FXR. The disclosure further relates to the use of the compounds for the preparation of a medicament for the treatment of diseases and/or conditions through binding of said nuclear receptor by said compounds and to a process for the synthesis of said compounds.

17 Claims, 2 Drawing Sheets

Specification includes a Sequence Listing.

(56) References Cited

U.S. PATENT DOCUMENTS

| | | |
|---|---|---|
| 2004/0105883 A1 | 6/2004 | Gao et al. |
| 2004/0105884 A1 | 6/2004 | Gao et al. |
| 2004/0105885 A1 | 6/2004 | Gao |
| 2004/0106607 A1 | 6/2004 | Arora et al. |
| 2004/0131670 A1 | 7/2004 | Gao |
| 2004/0152699 A1 | 8/2004 | Arora et al. |
| 2004/0157881 A1 | 8/2004 | Maekawa et al. |
| 2005/0272779 A1 | 12/2005 | Edwards et al. |
| 2006/0063772 A1 | 3/2006 | Arora et al. |
| 2007/0010562 A1 | 1/2007 | Bauer et al. |
| 2008/0032990 A1 | 2/2008 | Khalifah et al. |
| 2008/0114044 A1 | 5/2008 | Epple et al. |
| 2008/0182837 A1 | 7/2008 | Steurer et al. |
| 2008/0194634 A1 | 8/2008 | Arndt et al. |
| 2008/0207910 A1 | 8/2008 | Podhorez et al. |
| 2009/0074717 A1 | 3/2009 | Leivers et al. |
| 2009/0076103 A1 | 3/2009 | Olson et al. |
| 2009/0105251 A1 | 4/2009 | Jones et al. |
| 2009/0143451 A1 | 6/2009 | Andrews et al. |
| 2009/0197880 A1 | 8/2009 | Leivers et al. |
| 2009/0286782 A1 | 11/2009 | Ibrahim et al. |
| 2009/0286806 A1 | 11/2009 | Pajouhesh et al. |
| 2009/0306086 A1 | 12/2009 | Ibrahim et al. |
| 2010/0016313 A1 | 1/2010 | Millan et al. |
| 2010/0029655 A1 | 2/2010 | Leivers et al. |
| 2010/0048910 A1 | 2/2010 | Godschalx et al. |
| 2010/0093751 A1 | 4/2010 | Hynd et al. |
| 2010/0184809 A1 | 7/2010 | Kremoser et al. |
| 2010/0197662 A1 | 8/2010 | Ogawa et al. |
| 2010/0210660 A1 | 8/2010 | Kremoser et al. |
| 2010/0216827 A1 | 8/2010 | Ma et al. |
| 2010/0234347 A1 | 9/2010 | Dollinger et al. |
| 2010/0240657 A1 | 9/2010 | Sapountzis et al. |
| 2010/0256145 A1 | 10/2010 | Bak-Jensen et al. |
| 2011/0044943 A1 | 2/2011 | Leivers et al. |
| 2011/0212975 A1 | 9/2011 | Kao et al. |
| 2011/0220880 A1 | 9/2011 | Cheng et al. |
| 2011/0257196 A1 | 10/2011 | Lu et al. |
| 2011/0306493 A1 | 12/2011 | Paulini et al. |
| 2011/0312950 A1 | 12/2011 | Eckhardt et al. |
| 2012/0015988 A1 | 1/2012 | Hickey et al. |
| 2012/0021519 A1 | 1/2012 | Ichida et al. |
| 2012/0022067 A1 | 1/2012 | Chen et al. |
| 2012/0029027 A1 | 2/2012 | Estenne-Bouhtou et al. |
| 2012/0071524 A1 | 3/2012 | Lu et al. |
| 2012/0110705 A1 | 5/2012 | Le Vezouet et al. |
| 2012/0122681 A1 | 5/2012 | Le Vezouet et al. |
| 2012/0220603 A1 | 8/2012 | Pajouhesh et al. |
| 2012/0232116 A1 | 9/2012 | Kremoser et al. |
| 2012/0245166 A1 | 9/2012 | Grimaldi et al. |
| 2013/0231348 A1 | 9/2013 | Campbell et al. |
| 2013/0261108 A1 | 10/2013 | Tully et al. |
| 2013/0281503 A1 | 10/2013 | Melander et al. |
| 2014/0039007 A1 | 2/2014 | Tully et al. |
| 2014/0249100 A1 | 9/2014 | Shalwitz et al. |
| 2015/0082981 A1 | 3/2015 | Shiflett |
| 2015/0291572 A1 | 10/2015 | Schunk et al. |
| 2016/0376279 A1 | 12/2016 | Evans et al. |
| 2017/0073635 A1 | 3/2017 | Zhang |
| 2017/0204073 A1 | 7/2017 | Almstead et al. |
| 2017/0204096 A1 | 7/2017 | Gelin et al. |
| 2017/0279055 A1 | 9/2017 | Jang et al. |
| 2017/0304270 A1 | 10/2017 | Or et al. |
| 2017/0304271 A1 | 10/2017 | Or et al. |
| 2017/0304272 A1 | 10/2017 | Or et al. |
| 2017/0333399 A1 | 11/2017 | Or et al. |
| 2017/0334893 A1 | 11/2017 | Or et al. |
| 2017/0334894 A1 | 11/2017 | Or et al. |
| 2017/0355685 A1 | 12/2017 | Blomgren et al. |
| 2017/0355693 A1 | 12/2017 | Blomgren et al. |
| 2017/0355694 A1 | 12/2017 | Gege |
| 2017/0368038 A1 | 12/2017 | Badman et al. |
| 2018/0009754 A1 | 1/2018 | Long et al. |
| 2018/0030003 A1 | 2/2018 | Wang et al. |
| 2018/0051258 A1 | 2/2018 | Zhang et al. |
| 2018/0099957 A1 | 4/2018 | Ma et al. |
| 2018/0123052 A1 | 5/2018 | Zysman-Colman et al. |
| 2018/0280394 A1 | 10/2018 | Bates et al. |
| 2019/0308962 A1 | 10/2019 | Blomgren et al. |
| 2019/0315729 A1 | 10/2019 | Blomgren et al. |
| 2020/0071282 A1 | 3/2020 | Blomgren et al. |
| 2020/0255418 A1 | 8/2020 | Blomgren et al. |
| 2020/0281911 A1 | 9/2020 | Dalton et al. |
| 2020/0315972 A1 | 10/2020 | Kirby et al. |
| 2022/0204491 A1 | 6/2022 | Blomgren et al. |
| 2022/0242858 A1 | 8/2022 | Blomgren et al. |
| 2022/0370366 A1 | 11/2022 | Kirby et al. |

FOREIGN PATENT DOCUMENTS

| | | |
|---|---|---|
| CN | 104513213 | 4/2015 |
| CN | 106146483 | 11/2016 |
| CN | 106588804 | 4/2017 |
| CN | 106632294 | 5/2017 |
| CN | 106748922 | 5/2017 |
| CN | 107021957 | 8/2017 |
| CN | 107021958 | 8/2017 |
| EP | 1894924 | 3/2008 |
| EP | 2128158 | 12/2009 |
| EP | 2289883 | 3/2011 |
| EP | 3257847 | 12/2017 |
| JP | 2008308448 | 12/2008 |
| WO | WO-94/17059 | 8/1994 |
| WO | WO-94/24095 | 10/1994 |
| WO | WO-97/12883 | 4/1997 |
| WO | WO-00/37077 | 6/2000 |
| WO | WO-00/77011 | 12/2000 |
| WO | WO-03/015771 | 2/2003 |
| WO | WO-03/015777 | 2/2003 |
| WO | WO-03/016280 | 2/2003 |
| WO | WO-03/016288 | 2/2003 |
| WO | WO-03/080803 | 10/2003 |
| WO | WO-2004/024162 | 3/2004 |
| WO | WO-2004/045511 | 6/2004 |
| WO | WO-2004/046068 | 6/2004 |
| WO | WO-2004/046162 | 6/2004 |
| WO | WO-2004/048349 | 6/2004 |
| WO | WO-2004/087076 | 10/2004 |
| WO | WO-2005/056554 | 6/2005 |
| WO | WO-2005/077345 | 8/2005 |
| WO | WO-2005/077373 | 8/2005 |
| WO | WO-2005/123731 | 12/2005 |
| WO | WO-2006/101052 | 9/2006 |
| WO | WO-2007/070796 | 6/2007 |
| WO | WO-2007/076260 | 7/2007 |
| WO | WO-2007/092751 | 8/2007 |
| WO | WO-2007/095174 | 8/2007 |
| WO | WO-2007/110237 | 10/2007 |
| WO | WO-2007/140174 | 12/2007 |
| WO | WO-2007/140183 | 12/2007 |
| WO | WO-2007/140200 | 12/2007 |
| WO | WO-2008/002573 | 1/2008 |
| WO | WO-2008/025539 | 3/2008 |
| WO | WO-2008/025540 | 3/2008 |
| WO | WO-2008/051942 | 5/2008 |
| WO | WO-2008/073825 | 6/2008 |
| WO | WO-2008/097235 | 8/2008 |
| WO | WO-2008/155054 | 12/2008 |
| WO | WO-2008/157270 | 12/2008 |
| WO | WO-2009/005998 | 1/2009 |
| WO | WO-2009/012125 | 1/2009 |
| WO | WO-2009/081197 | 7/2009 |
| WO | WO-2009/127321 | 10/2009 |
| WO | WO-2009/149795 | 12/2009 |
| WO | WO-2010/034649 | 4/2010 |
| WO | WO-2010/034657 | 4/2010 |
| WO | WO-2010/036362 | 4/2010 |
| WO | WO-2010/052253 | 5/2010 |
| WO | WO-2010/093191 | 8/2010 |
| WO | WO-2011/020615 | 2/2011 |
| WO | WO-2011/109059 | 9/2011 |
| WO | WO-2012/076063 | 6/2012 |
| WO | WO-2012/087519 | 6/2012 |
| WO | WO-2012/087521 | 6/2012 |

(56) References Cited

FOREIGN PATENT DOCUMENTS

| | | |
|---|---|---|
| WO | WO-2013/001030 | 1/2013 |
| WO | WO-2013/007387 | 1/2013 |
| WO | WO-2013/037482 | 3/2013 |
| WO | WO-2013/192097 | 12/2013 |
| WO | WO-2014074848 | 5/2014 |
| WO | WO-2014/181287 | 11/2014 |
| WO | WO-2014/184271 | 11/2014 |
| WO | WO-2015/017813 | 2/2015 |
| WO | WO-2015/036442 | 3/2015 |
| WO | WO-2015/065983 | 5/2015 |
| WO | WO-2015/069666 | 5/2015 |
| WO | WO-2015/116856 | 8/2015 |
| WO | WO-2015/138969 | 9/2015 |
| WO | WO-2015/138986 | 9/2015 |
| WO | WO-2015/162244 | 10/2015 |
| WO | WO-2015/162538 | 10/2015 |
| WO | WO-2015/165960 | 11/2015 |
| WO | WO-2015/181275 | 12/2015 |
| WO | WO-2016/055441 | 4/2016 |
| WO | WO-2016/073767 | 5/2016 |
| WO | WO-2016/081918 | 5/2016 |
| WO | WO-2016/086115 | 6/2016 |
| WO | WO-2016/086134 | 6/2016 |
| WO | WO-2016/086169 | 6/2016 |
| WO | WO-2016/086218 | 6/2016 |
| WO | WO-2016/096115 | 6/2016 |
| WO | WO-2016/096116 | 6/2016 |
| WO | WO-2016/112305 | 7/2016 |
| WO | WO-2017/011466 | 1/2017 |
| WO | WO-2017/096130 | 6/2017 |
| WO | WO-2017/097870 | 6/2017 |
| WO | WO-2017/117687 | 7/2017 |
| WO | WO-2017/118294 | 7/2017 |
| WO | WO-2017/118762 | 7/2017 |
| WO | WO-2017/122209 | 7/2017 |
| WO | WO-2017/128896 | 8/2017 |
| WO | WO-2017/133521 | 8/2017 |
| WO | WO-2017/147047 | 8/2017 |
| WO | WO-2017/162211 | 9/2017 |
| WO | WO-2017/210526 | 12/2017 |
| WO | WO-2017/216727 | 12/2017 |
| WO | WO-2017/218330 | 12/2017 |
| WO | WO-2017/218337 | 12/2017 |
| WO | WO-2018/024224 | 2/2018 |
| WO | WO-2018/039384 | 3/2018 |
| WO | WO-2018/039386 | 3/2018 |
| WO | WO-2018/059314 | 4/2018 |
| WO | WO-2018/060075 | 4/2018 |
| WO | WO-2018/075207 | 4/2018 |
| WO | WO-2018/075650 | 4/2018 |
| WO | WO-2018/087599 | 5/2018 |
| WO | WO-2018/089212 | 5/2018 |
| WO | WO-2018/183193 | 10/2018 |
| WO | WO-2018/190643 | 10/2018 |
| WO | WO-2018/191393 | 10/2018 |
| WO | WO-2019023245 | 1/2019 |
| WO | WO-2020/150136 | 7/2020 |
| WO | WO-2020/172075 | 8/2020 |
| WO | WO-2020/185686 | 9/2020 |

OTHER PUBLICATIONS

Abu-Hayyeh et al., (2010) "Sulphated progesterone metabolites attenuate FXR function", 61st Annual Meeting of the American Association for the Study of Liver Diseases (Abstract).

Adams et al., (2012) "In vitro and in vivo regulation of FGF21 by FXR", 2012 Genetic and Molecular Basis of Obesity and Body Weight Regulation (J7) held jointly with 2012 Pathogenesis of Diabetes: Emerging Insights into Molecular Mechanisms (J8), (Abstract).

Adorini, (2008) "Clinical Translation of FXR agonists for the Treatment of Liver and Metabolic Disorders", 2008 Nuclear Receptors: Orphan Brothers (Z1), (Abstract).

Akwabi-Ameyaw et al., (2009) "FXR agonist activity of conformationally constrained analogs of GW 4064", Bioorganic & Medicinal Chemistry Letters 19: 4733-4739.

Alasmael et al., (2014) "The regulatory role of Farsenoid X Receptor on Matrix Metalloproteinases-2 and -9 in advanced Breast Cancer", The European Association for Cancer Research Conference Series on Goodbye Flat Biology: 30 Models and the Tumour Microenvironment (Abstract).

Ali et al., (2014) "Recent advances in the development of Farsenoid X Receptor agonists", Annals of Translational Medicine 3(1): 1-16.

Alrashid et al,. (2007) "FXR plays a key role in the anti-proliferative and apoptotic responses of bile acids in coloncarcinoma cell lines", 98th Annual Meeting of the American Association for Cancer Research, (Abstract).

Alvarez et al., "Reduced hepatic expression of Farsenoid X Receptor in hereditary cholestasis associated to mutation in ATP8B1 ", Human Molecular Genetics,13(20): 2451-2460, 2004.

Amiri-Kordestani et al., Why Do Phase III Clinical Trials in Oncology fail so Often?, vol. 104, Issue 8, Apr. 18, 2012. DOI: 10.1093/jnci/djs180. 2 pages.

Ananthanarayanan et al., "Human Bile Salt Export Pump Promoter is Transactivated by the Farsenoid X Receptor/Bile Acid Receptor", The Journal of Biological Chemistry, 276(31): 28857-28865, Aug. 3, 2001.

Andreone et al., (2014) "The FXR Agonist Obeticholic Acid (OCA) Improves Liver Biochemistry Parameters Correlated With Clinical Benefit Across a Range of Patient Characteristics", 65th Annual Meeting and Postgraduate Course of the American Association for the Study of Liver Diseases (AASLD), (Abstract).

Anonymous: "Cilofexor", Internet Citation, Jun. 6, 2018, XP002781675, Retrieved from the Internet: www.probechem.com/products_Cilofexor.aspx, retrieved on Jun. 5, 2018.

Anonymous: Safety, Tolerability, and Efficacy of Cilofexor in Adults With Primary Sclerosing Cholangitis Without Cirrhosis, ClinicalTrials.gov 2016, XP055703962, Retrieved from the Internet: clinicaltrials.gov/ct2/show/NCT02943460, retrieved on Jun. 11, 2020, 8 pages.

Aparecida et al., (2012) "Alcoholic liver steatosis in mice is aggravated by low-protein diet and reversed by FXR agonist", 1st Conference on Metabolism, Diet and Disease (Abstract).

Aranda et al., "Nuclear Hormone Receptors and Gene Expression", Physiological Reviews 81(3): 1269-1304, Jul. 2001.

Ashland; Pharmaceutical Technology Report: PTR-096. Utility of PolyplasdoneTM crospovidone as a Solubilizer; 2014; ashland.com/file_source/Ashland/Product/Documents/Pharmaceutical_1/PTR_096_Polyplasdone_crospovidone_Solubilizer.pdf; accessed Aug. 14, 2021 (Year: 2014). 5 pages.

Auwerx, (2006) "Turning Up the Heat with Bile Acids", Nuclear Receptors: Steroid Sisters (X4), (Abstract).

Baghdasaryan et al., (2010) "Therapeutic Effects of FXR and TGR5 Activation in the MDR2 (ABCB4)Mouse Model of Sclerosing Cholangitis", 45th Annual Meeting of the European Association for the Study of the Liver (EASL), (Abstract).

Baghdasaryan et al., (2010) "Therapeutic Targeting of Nuclear and Membrane Bile Acid Receptors in a Mouse Model of Chronic Cholestasis", 61st Annual Meeting of the American Association for the Study of Liver Diseases (AASLD), (Abstract).

Baghdasaryan et al., (2011) "FXR but not Tgr5 activation stimulates HCO3—rich bile secretion and ameliorates liver damage in Mdr2-/- (Abcb4-/-) mouse model of chronic liver injury", 62nd Annual Meeting of the American Association for the Study of Liver Diseases (AASLD), (Abstract).

Balasubramaniyan et al., (2005) "Human Organic Solute Transporter Alpha (OST-ALPHA) is Transactivated by FXR, HNF-4 Alpha and FTF/LRH-1: Implications for Basolateral Bile Acid Transport in Human Liver", 56th Annual Meeting of the American Association for the Study of Liver Diseases (AASLD), (Abstract).

Balbach et al., "Pharmaceutical evaluation of early development candidates "the 100 mg approach"", International Journal of Pharmaceutics, 2004, vol. 275, pp. 1-12.

Ballatori et al., (2010) "Ost alpha-Ost beta: A key membrane transporter of bile acids and conjugated steroids", Front Biosci 14: 2829-2844.

(56) References Cited

OTHER PUBLICATIONS

Bart et al., (2004) "Perspective targets in the treatment of the metabolic syndrome", 13th European Congress on Obesity (European Association for the Study of Obesity, (Abstract).

Bass et al., (2011) "Conformationally constrained Farsenoid X Receptor (FXR) agonists: Heteroaryl replacements of the naphthalene", Bioorganic & Medicinal Chemistry Letters 21: 1206-1213.

Bechmann et al., (2011) "Free fatty acids repress SHP activation and adiponectin counteracts bile acid induced liver injury: New target options for NASH treatment?", 62nd Annual Meeting of the American Association for the Study of Liver Diseases (AASLD), (Abstract).

Beth et al., "Soy Lipid-Derived Phytosterols are FXR Antagonists-Potential Role in Total Parenteral Nutrition-Associated Cholestasis (TPNAC)", Digestive Disease Week 2004: American Association for the Study of Liver Diseases, American Gastroenterological Association, American Society for Gastrointestinal Endoscopy, Society for Surgery of the Alimentary Tract, (Abstract).

Beuers et al., (2014) "FXR Agonist Obeticholic Acid: Pruritus, A Common Side Effect Ameliorated by Dose Titration", 65th Annual Meeting and Postgraduate Course of the American Association for the Study of Liver Diseases (AASLD), (Abstract).

Bianchi et al., (2011) "Farnesoid-X-receptor (FXR) agonist INT-747 restores hepatic DDAH activity after ischemia/reperfusion injury", 35° Congresso Nazionale della Societa Italiana di Farmacologia (SIF)/35th National Congress of the Italian Society of Pharmacology, (Abstract).

Bilz et al., "Activation of the Farsenoid X Receptor improves lipid metabolism in combined hyperlipidemic hamsters", Am. J. Physiol. Endocrinol. Metab., 290(4) E716-722, 2006, doi: 10.1152/aipendo. 00355.2005.

Boesjes et al., (2014) "Hepatic Farnesoid X-Receptor Isoforms a2 and a4 Differentially Modulate Bile Salt and Lipoprotein Metabolism in Mice", Plos One 9: 1-19.

Bowlus et al., (2014) "Obeticholic Acid in PBC Patients: The Utility of Titration Based on Therapeutic Response and Tolerability", 65th Annual Meeting and Postgraduate Course of the American Association for the Study of Liver Diseases (AASLD), (Abstract).

Brzozowski et al., "Molecular basis of agonism and antagonism in the oestrogen receptor", Nature, 389:753-758, Oct. 16, 1997.

Buttar et al., (2007) "Role of Farnesoid-X-receptor in Esophageal Carcinogenesis" Digestive Disease Week 2007 (DDW): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).

Cai et al., "FXR: a target for cholestatic syndromes?", Expert Opin. Ther. Targets, 10(3): 409-421, 2006.

Caira, M. R., Crystalline Polymorphism of Organic Compounds, Topics in Current Chemistry 1998, vol. 198, Springer Verlag Berlin Heidelberg, pp. 163-208, XP001156954.

Cariou et al., "The Farsenoid X Receptor Modulates Adiposity and Peripheral Insulin Sensitivity in Mice", The Journal of Biological Chemistry, 28, 11039-11049, Apr. 21, 2006.

Cariou et al., (2005) "Farsenoid X Receptor (FXR) regulates peripheral insulin sensitivity", 41st Annual Meeting of the European Association for the Study of Diabetes (EASD), (Abstract).

Carotti, et al., (2014), "Beyond bile acids: targeting Farnesoid X Receptor (FXR) with natural and synthetic ligands", Curr Top Med Chem, 14:2129-42.

Carr, et al., (2015), "FXR agonists as therapeutic agents for non-alcoholic fatty liver disease", Curr Atheroscler Rep, 17:500.

Cha et al., (2009) "Farsenoid X Receptor (FXR) Agonist Improves Insulin Resistance and Ameliorates Diabetic Nephropathy in db/db Mice", 42nd Annual Meeting and Exposition of the American Society of Nephrology (ASN), (Abstract).

Changming et al., (2009) "Ileal bile acid binding protein mediates the chemopreventative effect of ursodeoxycholic acid by activating nuclear receptor FXR in colorectal cancer cells", 100th Annual Meeting of the American Association for Cancer Research (AACR), (Abstract).

Chen et al., "Progressive Familial Intrahepatic Cholestasis: Type I, Is Associated With Decreased Farsenoid X Receptor Activity", Gastroenterology, 126, 756-764, Mar. 2004.

Cheng et al., (2011) "Farsenoid X Receptor (FXR) controls expression of Fibroblast Growth Factor 21 (FGF21) in liver cells", 4th International Congress on Prediabetes and the Metabolic Syndrome, (Abstract).

Chennamsetty et al., (2010) "Role of Farsenoid X Receptor Agonists in the In Vivo and In Vitro Expression of Apolipoprotein(a)", 78th European Atherosclerosis Society Congress (EAS), (Abstract).

Chiang et al., (2004) "Mechanisms of bile acid inhibition of genes in bile acid synthesis", Falk Symposium No. 141, Bile Acids and Cholesterol Metabolism and its Therapeutical Implications, (Abstract).

Chignard et al., (2003) "The VILP receptor VPAC-1 in highly expressed and regulated by FXR and RXR alpha nuclear receptors in the human gallbladder epithelium", 54th Annual Meeting of the American Association for the Study of Liver Diseases (AASLD), (Abstract).

Cho et al., (2011) "Guggulsterone Inhibits LXRa Mediated SREBP-1C-Dependent Hepatic Steatosis through PKC Dependent Pathway", 46th Annual Meeting of the European Association for the Study of the Liver (EASL), (Abstract).

Chouinard et al., (2007) "Bile Acid 7a-Hydroxylase and 12s-Hydroxylase Indices Convey Target Pharmacology, Predict Preclinical Endpoint Efficacy and Offer Utility as Clinical Translational Markers of FXR Agonist Activity", Nuclear Receptors and Metabolism (Z1) held jointly with Metabolic Syndrome and Cardiovascular Risk (Z2), (Abstract).

Chu et al., (2013) "Bile Acids Induce COX-2 Expression in Human Esophagus via Activation of Farsenoid X Receptor (FXR) and NfB", 54th Annual Meeting at Digestive Disease Week (DDW 2013): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).

Claudel et al., "The Farsenoid X Receptor: A Molecular Link Between Bile Acid and Lipid and Glucose Metabolism", Arteriosclerosis, Thrombosis, and Vascular Biology, 25, 2020-2031, 2005, obtained from URL=http://atvb.ahaioumals.org, download date Jan. 19, 2012.

Claudel et al., (2005) "Constitutive Androstane Receptor Negatively Regulates Human Apolipoprotein A-1 Expression", 78th Annual Scientific Sessions of the American Heart Association (AHA), (Abstract).

ClinicalTrials.gov; NCT02781584 (Year: 2016). 7 pages.

ClinicalTrials.gov; NCT02854605 (Year: 2016). 5 pages.

Communication pursuant to Rule 114(2) EPC, observations by a third party for European Patent Application No. 20708721.4 dated Sep. 20, 2021. 8 pages.

Cortes et al., (2005) "Recombinant Adenovirus-Mediated Functional Expression and Heterodimeric Nuclear Receptor-Dependent Regulation Of Syndecan-1 in the Murine Liver: Implications in Cholesterol Metabolism", Digestive Disease Week 2005 (DDW): American Association for the Study of Liver Diseases, American Gastroenterological Association, American Society for Gastrointestinal Endoscopy, Society for Surgery of the Alimentary Tract, (Abstract).

Crawley, M.L., Farnesoid X receptor modulators: a patent review, Expert Opinion on Therapeutic Patents. 2010, vol. 20, No. 8, doi:10.1517/13543776.2010.496777, ISSN 1354-3776, pp. 1047-1057, XP055401832.

D'Amore et al., (2014) "Design, Synthesis, and Biological Evaluation of Potent Dual Agonists of Nuclear and Membrane Bile Acid Receptors", Journal of Medicinal Chemistry 57: 937-954.

Das et al., (2007) "Farsenoid X Receptor Dependent Regulation of MMP9 in Blood Outgrowth Endothelial Cells Contributes to Cell Migration and Homing Through A Pathway involving SHP and KLF repressor proteins", Digestive Disease Week 2007 (DDW): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).

(56) References Cited

OTHER PUBLICATIONS

Das et al., (2007) "FXR bile acid receptor activates focal adhesion kinase and stress fiber-mediated motility in endothelial cells", 58th Annual Meeting of the American Association for the Study of Liver Diseases (AASLD), (Abstract).
Das et al., (2009) "FXR Promotes Endothelial Cell Motility through Reciprocal Regulation of FAK and MMP-9", 2009 Experimental Biology Annual Meeting (FASEB) held jointly with the the American Association of Anatomists (AAA), the American Physiological Society (APS), American Society for Biochemistry and Molecular Biology (ASBMB), American Society for Investigative Pathology (ASIP), American Society for Nutrition (ASN), and the American Society for Pharmacology and Experimental Therapeutics (ASPET), (Abstract).
De Oliveira et al., (2012) "Bile acid receptor agonists INT-747 and INT-777 decrease estrogen deficiency-related postmenopausal obesity and hepatic steatosis", 63rd Annual Meeting and Postgraduate Course of the American Association for the Study of Liver Diseases (AASLD), (Abstract).
Demars et al., (2005) "Farnesoid-X-receptor and carcinogenesis in Barrett's esophagus", 96th American Association for Cancer Research Annual Meeting, (Abstract).
Deuschle et al., (2012) "FXR directly controls the tumor suppressor NDRG2 and FXR agonists reduce tumor growth and metastasis in an orthotopic xenograft mouse model", 47th Annual Meeting of the European Association for the Study of the Liver (EASL), (Abstract).
Deuschle et al., (2014) "The nuclear bile acid receptor FXR controls the liver derived tumor suppressor histidine-rich glycoprotein", International Journal of Cancer, 00: 00-00.
Dodson et al., (2005) "Concerted Control of Lipids and Insulin Sensitization by FXR", 87th Annual Meeting of the Endocrine Society (ENDO), (Abstract).
Dodson et al., (2007) "Concerted control of insulin sensitization through lipid and carbohydrate metabolism by FXR", Nuclear Receptors and Metabolism (Z1) held jointly with Metabolic Syndrome and Cardiovascular Risk (Z2), (Abstract).
Doggrell, "New targets in and potential treatments for cholesterol gallstone disease", Current Opinion in Investigational Drugs 7(4): 344-348, 2006.
Dossa et al., (2014) "Bile Acids Differentially Control Intestinal Cell Proliferation via Src Kinase", 2014 Clinical Congress of the American College of Surgeons (ACS), (Abstract).
Dossa et al., (2014) "Intestinal bile acids differentially control intestinal cell proliferation", 34th Annual Meeting of the Surgical Infection Society (SIS), (Abstract).
Duran-Sandoval et al., "Potential regulatory role of the Farsenoid X Receptor in the metabolic syndrome", Biochimie 87:93-98, 2005.
Edwards et al., (2007) "FXR Modulates Lipid and Glucose Metabolism", Nuclear Receptors and Metabolism (Z1) held jointly with Metabolic Syndrome and Cardiovascular Risk (Z2), (Abstract).
Eloranta et al., (2004) "Coordinate transcriptional regulation of bile acid homeostasis and drug metabolism", Archives of Biochemistry and Biophysics 433: 397-412.
Eloranta et al., (2005) "Human organic solute transporter-alpha (OSTalpha) and -beta (OSTbeta) genes are transactivated by the nuclear bile acid receptor/Farsenoid X Receptor (FXR)", 56th Annual Meeting of the American Association for the Study of Liver Diseases (AASLD), (Abstract).
European Search Report for EP11005722, completed Sep. 13, 2011, 2 pages.
European Search Report for EP15002478.4, completed Nov. 17, 2015, 8 pages.
Extended European search report for European Application No. 17175336.1 dated Jul. 19, 2017. 8 pages.
Extended European search report for European Application No. 19188723.1 dated Oct. 24, 2019. 8 pages.
Extended European search report for European Application No. 20179813.9 dated Aug. 3, 2020. 6 pages.
Extended European Search Report for European Patent Application No. 17000383.4 dated Oct. 4, 2017. (8 pages).
Evans et al., (2007) "Activation of Farsenoid X Receptor (FXR) in the treatment of dyslipidemia", Nuclear Receptors and Metabolism (Z1) held jointly with Metabolic Syndrome and Cardiovascular Risk (Z2), (Abstract).
Evans et al., (2007) "Activation of Farsenoid X Receptor (FXR) protects against diet-induced dyslipidemia", 76th European Atherosclerosis Society Congress (EAS), (Abstract).
Evans, "The Nuclear Receptor Superfamily: A Rosetta Stone for Physiology", Molecular Endocrinology 19(6): 1429-1438, Jun. 2005.
Falk et al., (2006) "Primary biliary cirrhosis: From ursodeoxycholic acid towards targeting strategies for therapy", Falk Symposium No. 155: XIX International Bile Acid Meeting—Bile Acids: Biological Actions and Clinical Relevance (Abstract).
Fang et al., (2008) "The acetylase p300 and deacetylase SIRT1 are critical in vivo FXR cofactors in regulation of liver metabolism", 2008 Nuclear Receptors: Orphan Brothers (Z1), (Abstract).
Feng et al., (2009) "Identification of an N-oxide pyridine GW4064 analog as a potent FXR agonist", Bioorganic & Medicinal Chemistry Letters 19: 2595-2598.
Figge et al., "Hepatic Overexpression of Murine Abcb11 Increases Hepatobiliary Lipid Secretion and Reduces Hepatic Steatosis", The Journal of Biological Chemistry 279(4): 2790-2799, Jan. 23, 2004.
Fiorucci et al., "Protective Effects of 6-Ethyl Chenodeoxycholic Acid, a Farsenoid X Receptor Ligand, in Estrogen-Induced Cholestasis", The Journal of Pharmacology and Experimental Therapeutics 313(2): 604-612, 2005.
Fiorucci et al., "The Nuclear Receptor SHP Mediates Inhibition of Hepatic Stellate Cells by FXR and Protects Against Liver Fibrosis", Gastroenterology 127(5): 1497-1512, Nov. 2004.
Fiorucci et al., (2003) "The FXR-agonist, 6-Ethyl-Chenodeoxycholic Acid (6-ECDCA), protects against estrogen-induced cholestasis in rats", Pellicciari R. Digestive Disease Week 2003 (DDW): American Association for the Study of Liver Diseases, American astroenterological Association, American Society for Gastrointestinal Endoscopy, Society for Surgery of the Alimentary Tract (Abstract).
Fiorucci et al., (2005), "A Farsenoid X Receptor-Small Heterodimer Partner Regulatory Cascade Modulates Tissue Metalloproteinase Inhibitor-1 and Matrix Metalloprotease Expression in Hepatic Stellate Cells and Promotes Resolution of Liver Fibrosis", The Journal of Pharmacology and Experimental Therapeutics, 314: 584-595.
Fiorucci et al., (2010) "The Bile Acid Sensor FXR Modulates Hydrogen Sulfide Generation in the Gastric Mucosa and Protects Against Injury Caused by Aspirin", Digestive Disease Week 2010 (DDW), (Abstract).
Fiorucci et al., (2014) "Targeting FXR in cholestasis: hype or hope", Expert Opinion 18 (12).
Flatt et al., (2005) "SAR of highly potent full-range modulators of the Farsenoid X Receptor", 229th National Meeting of the American Chemical Society (Abstract).
Flesch et al., (2014) "Screening, synthesis and characterization of novel ligands for Farsenoid X Receptor (FXR)", 2014 Annual Meeting on Trends and Perspectives in Pharmaceutical Sciences (DPhG) Annual Meeting of the German Pharmaceutical Society (DPhG), (Abstract).
Flesch et al., (2014) "Screening, Synthesis and Characterization of Novel Ligands for Farsenoid X Receptor (FXR)", 23rd International Symposium on Medicinal Chemistry (ISMC) held Jointly with the European Federation for Medicinal Chemistry (EFMC), (Abstract).
Flesch et al., (2015) "Fragmentation of GW4064 led to a highly potent partial Farsenoid X Receptor agonist with improved drug-like properties", Bioorganic & Medicinal Chemistry 13:3490-8.
Forman et al., "Identification of a Nuclear Receptor That is Activated by Farnesol Metabolites", Cell 81:687-693, Jun. 2, 1995.
Fuchs et al., (2012) "Changes in hepatic bile acid composition protect BSEP (ABCB11) KO mice from hepatic inflammation in methionine choline deficient (MCD)-diet induced NASH", 63rd Annual Meeting and Postgraduate Course of the American Association for the Study of Liver Diseases (AASLD), (Abstract).
Fuchs et al., (2012) "FXR is a key player in NAFLD development by controlling chop expression", 47th Annual Meeting of the European Association for the Study of the Liver (EASL), (Abstract).

(56) References Cited

OTHER PUBLICATIONS

Fuchs et al., (2013) "FXR controlled CHOP as novel key player in NAFLD progression", 64th Annual Meeting and Postgraduate Course of the American Association for the Study of Liver Diseases (AASLD), (Abstract).
Fuchs et al., (2014) "Intrahepatic Changes in Bile Acid Composition Protects Bsep (ABCB11) KO Mice From Hepatic Injury in Methionine Choline-Deficient Diet Induced NASH", 55th Annual Meeting at Digestive Disease Week (DDW 2014 ): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Gadaleta et al., (2009) "FXR activation represses TNFa-induced NF-?B signalling", 2009 Spring Meeting of the Dutch Society for Gastroenterology/2009 Voorjaarsvergadering Nederlandse Vereniging voor Gastroenterologie (Abstract).
Gadaleta et al., (2010) "Intestinal Bile Salt Nuclear Receptor FXR Protects From Inflammatory Bowel Disease: Potential Therapeutic Implications", Digestive Disease Week 2010 (DDW), (Abstract).
Gadaleta et al., (2011) "Farsenoid X Receptor activation inhibits inflammation and preserves the intestinal barrier in inflammatory bowel disease", Inflammatory bowel disease 60: 463-472.
Gautier et al., (2011) "Farsenoid X Receptor Activation Induces Cholesteryl Ester Transfer Protein Expression in Humans and Transgenic Mice", 12th Annual Conference on Arteriosclerosis, Thrombosis and Vascular Biology (ATVB) in collaboration with the Council on Peripheral Vascular Disease (Abstract).
Gautier et al., (2011) "Farsenoid X Receptor Activation Induces Cholesteryl Ester Transfer Protein Expression in Humans and Transgenic Mice", 79th European Atherosclerosis Society Congress (EAS), (Abstract).
Gege et al., (2014) "Knocking on FXR's Door: The "Hammerhead"-Structure Series of FXR Agonists—Amphiphilic Isoxazoles with Potent In Vitro and In Vivo Activities", Current Topics in Medicinal Chemistry 14: 1-16.
Gioiello et al., (2014) "Bile Acid Derivatives as Ligands of the Farsenoid X Receptor: Molecular Determinants for Bile Acid Binding and Receptor Modulation", Current Topics in Medicinal Chemistry 14: 2159-2174.
Giordano et al., (2010) "Activated Farsenoid X Receptor Inhibits Growth of Tamoxif en-Resistant MCF-7 Breast Cancer Cells, through Down-Regulation of HER2 Expression", 92nd Annual Meeting of the Endocrine Society (ENDO), (Abstract).
Giordano et al., (2010) "Activated Farsenoid X Receptor inhibits growth of tamoxifen-resistant breast cancer cells", 2010 Experimental Biology Annual Meeting (FASEB) held jointly with the American Association of Anatomists (AAA), the American Physiological Society (APS), American Society for Biochemistry and Molecular Biology (ASBMB), American Society for Investigative Pathology (ASIP), American Society for Nutrition (ASN) and the American Society for Pharmacology and Experimental Therapeutics (ASPET), (Abstract).
Giordano et al., (2014) "FXR Ligands, by Interfering with Tumor/Microenvironment Crosstalk, Inhibit Breast Tumor Growth and Progression", 2nd Joint Meeting of Pathology and Laboratory Diagnostics, 32.Congress of the Societa Italiana di Patologia e Medicina Traslazionale, 64.National Congress of the Associazione Italiana di Patologia Clinica e Medicina Molecolare/32nd Congress of the Italian Society of Pathology and Translational Medicine and 64th National Congress of the Italian Association of Clinical Pathology and Molecular Medicine (Abstract).
Glastras et al., (2013) "The role of FXR in maternal obesity related renal injury in mother and offspring", 2013 Annual Scientific Meeting of the Australian Diabetes Educators Association (ADEA) and the Australian Diabetes Society (ADS), (Abstract).
Gnerre et al., (2004) "CYP3A4 and CYP3A11 are regulated by the nuclear receptor FXR and primary bile acids in cell cultures and in mice", 15th International Symposium on Microsomes and Drug Oxidations: Chemical Biology in the Postgenomic Era—New Approaches and Applications (Abstract).
Gokhale et al., Chapter 4—API Solid-Form Screening and Selection. Developing Solid Oral Dosage Forms: Pharmaceutical Theory and Practice 2017, pp. 85-112.
Goodwin et al., "A Regulatory Cascade of the Nuclear Receptors FXR, SHP-1, and LRH-1 Represses Bile Acid Biosynthesis", Molecular Cell 6: 517-526, Sep. 2000.
Grefhorst et al., (2004) "The role of nuclear hormone receptors in hepatic insulin resistance", 3rd Dutch Endo-Neuro-Psycho Meeting 2004 (Abstract).
Guan et al., (2008) "Nuclear receptors and metabolic syndrome", 2008 Beijing Conference of Physiological Sciences jointly supported by the American Physiological Society, Australian Physiological Society, Canadian Physiological Society, Chinese Association for Physiological Sciences, and the Physiological Society (UK), (Abstract).
Guo-Ning et al., (2014) "Synthesis and Bioactivity of Chalcones and Related Compounds as Farsenoid X Receptor (FXR) Antagonists", 34th National Medicinal Chemistry Symposium (NMCS), (Abstract).
Habegger et al., (2012) "Fibroblast Growth Factor 21 and Farsenoid X Receptor Mediate Chronic Glucagon Action", 72nd Annual Meeting and Scientific Sessions of the American Diabetes Association (ADA), (Abstract).
Hambruch et al., (2012) "Synthetic Farsenoid X Receptor agonist PX20606 demonstrates anti-atherosclerotic effects and lowers cholesterol in HDL2 but not in HDL3 subtractions", Poster.
Hambruch et al., (2013) "FXR Agonist Px-102 Improves Hepatic Steatosis in NAFLD Rodent Models", 23rd Conference of the Asia Pacific Associaton for the Study of the Liver (APASL 2013): Transforming Science to Clinical Practice (Abstract).
Hambruch, et al, (2013) "FXR agonist Px-102 improves hepatic steatosis in NAFLD mouse models", Phenex (Poster).
Hanniman et al., "Loss of functional Farsenoid X Receptor increases atherosclerotic lesions in apolipoprotein E-deficient mice", Journal of Lipid Research, 46:2595-2604, 2005.
Hansen et al., (2014) "The FXR agonist obeticholic acid improves alkaline phosphatase/bilirubin response criterion associated with transplant-free survival in primary biliary cirrhosis", 2014 European Association for the Study of the Liver (EASL) Monothematic Conference: Primary Biliary Cirrhosis (PBC), (Abstract).
Harnish et al., (2007) "A synthetic Farsenoid X Receptor (FXR) agonist protects against diet-induced dyslipidemia", 16th International Symposium on Drugs Affecting Lipid Metabolism (Abstract).
Harnish et al., (2007) "The Farsenoid X Receptor (FXR) Antagonizes Oxidized LDL Receptor, LOX-1, Activation", 80th Annual Scientific Sessions of the American Heart Association (AHA), (Abstract).
Harnish, (2007) "A Synthetic Farsenoid X Receptor Agonist Protects Against Diet-Induced Dyslipidemia", 80th Annual Scientific Sessions of the American Heart Association (AHA), (Abstract).
Harriman et al., Acetyl-CoA carboxylase inhibition by ND-630 reduces hepatic steatosis, improves insulin sensitivity, and modulates dyslipidemia in rats, PNAS, pp. E1796-E1805, Published online Mar. 14, 2016, pnas.org/cgi/doi/10.1073/pnas.1520686113.
Hartman et al., (2007) "Farsenoid X Receptor (FXR) Regulates RECK Expression", 58th Annual Meeting of the American Association for the Study of Liver Diseases (AASLD), (Abstract).
Hawksworth, (2010) "Hepatictransporters—Regulation, induction and potential for drug-drug interactions", 8th Southeast European Congress on Xenobiotic Metabolism and Toxicity (XEMET 2010), (Abstract).
He et al., "Downregulation of Endothelin-1 by Farsenoid X Receptor in Vascular Endothelial Cells", Circulation Research 98(2): 192-199, 2006, plus online supplement, obtained from URL=http://circres.ahaioumals.org, download date Jun. 11, 2012, 14 pages.
Healy et al., Pharmaceutical solvates, hydrates and amorphous forms: A special emphasis on cocrystals, Advanced Drug Delivery Reviews 2017, vol. 117, pp. 25-46, doi.org/10.1016/j.addr.2017.03.002.

(56) References Cited

OTHER PUBLICATIONS

Heery et al., "A signature motif in transcriptional co-activators mediates binding to nuclear receptors", Nature 387:733-736, Jun. 12, 1997.
Heinzel et al., "A complex containing N-CoR, mSin3 and histone deacetylase mediates transcriptional repression", Nature, 387:43-48, May 1, 1997.
Henry et al., (2009) "Farsenoid X Receptor Agonists: A New Therapeutic Class for Diabetes and Fatty Liver Disease? The First FXR Therapeutic Study in Diabetes", 69th Annual Meeting and Scientific Sessions of the American Diabetes Association (ADA), (Abstract).
Hirschfield et al., (2014) "Efficacy of Obeticholic Acid in Patients with Primary Biliary Cirrhosis and Inadequate Response to Ursodeoxycholic Acid", Gastroenterology 148: 751-761.
Hoegenauer et al., (2014) "G-Protein-coupled Bile Acid Receptor 1 (GPBAR1 ,TGR5) agonists reduce the production of proinflammatory cytokines and stabilize the 57 alternative macrophage phenotype", Journal of Medicinal Chemistry 57: 10343-54.
Holt et al., "Definition of a novel growth factor-dependent signal cascade for the suppression of bile acid biosynthesis", Genes & Development 17:1581-1591, 2003.
Horth et al., (2009) "Influence of bile acids on stimulus-secretion coupling in pancreatic beta cells", Fruhjahrstagung der Deutschen Gesellschaft fur Experimentelle und Klinische Pharmakologie und Toxikologie/50th Spring Meeting of the German Society for Experimental and Clinical Pharmacology and Toxicology (Abstract).
Horth et al., (2010) "The function of murine pancreatic beta cells is affected by bile acids", Fruhjahrstagung der Deutschen Gesellschaft fur Experimentelle und Klinische Pharmakologie und Toxikologie/ 51st Spring Meeting of the German Society for Experimental and Clinical Pharmacology and Toxicology (Abstract).
Horth et al., (2011) "Bile acids affect the function of murine pancreatic beta cells", 47th Annual Meeting of the European Association for the Study of Diabetes (EASD), (Abstract).
Horth et al., (2011) "Link between the nuclear farnesoid receptor and KATP channel activity in beta-cells", 90th Annual Meeting of the German Physiological Society/Deutsche Physiologische Gesellschaft (PPG), (Abstract).
Houssin et al., (2010) "The FXR activators, chenodeoxycholic acid and GW4064 inhibit the proliferation of prostate cancer LNCaP and LAPC-4 cells", 2010 Nuclear Receptors: Signaling, Gene Regulation and Cancer (X7), (Abstract).
Howarth et al., (2007) "Is the Farsenoid X Receptor in Japanese medaka (*Oryzias latipes*) a target for exogenous compounds?", 46th Annual Meeting of the Society of Toxicology (Abstract).
Hsu et al., (2014) "Quantitative Profiling of Environmental Chemicals and Drugs for Farsenoid X Receptor Activity", 53rd Annual Meeting of the Society of Toxicology (SOT 2014), (Abstract).
Huang et al., "Farsenoid X Receptor Activates Transcription of the Phospholipid Pump MDR3", The Journal of Biological Chemistry 278(51): 51085-51090. Dec. 19, 2003.
Huang et al., "Nuclear Receptor-Dependent Bile Acid Signaling Is Required for Normal Liver Regeneration", Science 312:233-236, Apr. 14, 2006.
Huang et al., (2014) "Recent Advances in Non-Steroidal FXR Antagonists Development for Therapeutic Applications", Current Topics in Medicinal Chemistry 14: 2175-2187.
Huang et al., Design, Synthesis, and Biological Evaluation of Novel Nonsteroidal Farnesoid X Receptor (FXR) Antagonists: Molecular Basis of FXR Antagonism, ChemMedChem 2015, 10, pp. 1184-1199.
Hulzebos et al., (2005) "Pharmacological FXR Activation and the Enterohepatic Circulation of Bile Salts in Rats: Inhibition of Cholate Synthesis Rate and Reduced Cholate Pool Size", 115th Annual Meeting of the American Pediatric Society and 74th Annual Meeting of the Society for Pediatric Research together with the American Society of Pediatric Hematology/Oncology (ASPHO), the American Society of Pediatric Nephrology, the Lawson Wilkins Pediatric Endocrine Society and the Pediatric Infectious Disease Society (Abstract).
Hwang et al., (2004) "The Cellular Distribution of FXR and RXRa Expression in Developing Rat Ileal Mucosa", Digestive Disease Week 2004 (DDW): American Association for the Study of Liver Diseases, American Gastroenterological Association, American Society for Gastrointestinal Endoscopy, Society for Surgery of the Alimentary Tract (Abstract).
Idelman et al., (2012) "Activation of the farnesoid X-receptor (FXR) suppresses cyclin D1 expression and decreases proliferation of colon and breast cancer cells", 63rd Annual Meeting and Postgraduate Course of the American Association for the Study of Liver Diseases (AASLD), (Abstract).
Idelman et al., (2014) "Activation of the farnesoid X-receptor suppresses cyclin D1 expression and decreases proliferation", 2014 Experimental Biology Annual Meeting (FASEB) held jointly with the the American Association of Anatomists (AAA), the American Physiological Society (APS), American Society for Biochemistry and Molecular Biology (ASBMB), American Society for Investigative Pathology (ASIP), American Society for Nutrition (ASN), Chinese Pharmacological Society (CPS) and the American Society for Pharmacology and Experimental Therapeutics (ASPET), (Abstract).
Ikpa et al., (2014) "Impaired FXR Signaling in the CF Intestine", 28th Annual North American Cystic Fibrosis Conference (NACFC), (Abstract).
Inagaki et al., "Fibroblast growth factor 15 functions as an enterohepatic signal to regulate bile acid homeostasis", Cell Metabolism, 2, 217-225, Oct. 2005.
Inagaki et al., "Regulation of antibacterial defense in the small intestine by the nuclear bile acid receptor", Proc. Natl. Acad. Sci USA, 103, 3920-3905, 2006, doi:10.1073/pnas.0509592103.
Inagaki et al., (2004) "Bile acid receptor, FXR, regulates host defense in intestine", 18th International Bile Acid Meeting: Bile Acid and Cholesterol Metabolism and its Therapeutic Implications (Abstract).
Inagaki et al., (2004) "Bile acid receptor, FXR, regulates host defense in intestine", Falk Symposium No. 141 Bile Acids and Cholesterol Metabolism and its Therapeutical Implications (Abstract).
Inagaki et al., (2006) "Regulation of Mucosal Defense in Intestine by the Nuclear Bile Acid Receptor", Nuclear Receptors: Orphan Brothers (X3), (Abstract).
International Preliminary Report on Patentability for International Application No. PCT/US2017/036727 dated Dec. 18, 2018. 7 pages.
International Search Report and Written Opinion for International Application No. PCT/US2017/036727 dated Sep. 4, 2017. 11 pages.
International Search Report and Written Opinion for International Application No. PCT/US2020/013319 dated May 6, 2020. 15 pages.
International Search Report and Written Opinion for International Application No. PCT/US2020/018403 dated Jun. 3, 2020. 19 pages.
International Search Report and Written Opinion for International Application No. PCT/US2020/021722 dated Jun. 19, 2020. 15 pages.
International Search Report and Written Opinion dated Aug. 8, 2017, for PCT/US2017/036743, 14pgs.
International Search Report and Written Opinion for International Application No. PCT/EP2012/002941 dated Aug. 16, 2012. (9 pages).
Ishii, (2010) "Bile acids and their pathophysiological role in metabolic disorders", 83rd Annual Meeting of the Japanese Society for Pharmacology (Abstract).
Jae et al., (2009) "Antidiabetic effects of novel ligands for the orphan nuclear receptor LRH-1", 2009 Type 2 Diabetes and Insulin Resistance (J3), (Abstract).
Jain et al., (2009) "Enteral bile acids improve TPN related cholestasis and gut mucosal atrophy: potential role of FXR and FGF19", 22nd Annual Meeting of the North American Society for Pediatric Gastroenterology, Hepatology and Nutrition (NASPGHAN), (Abstract).
Jeong et al., (2005) "Expression of All 48 Nuclear Hormone Receptors in Lung Cancer", Molecular Pathogenesis of Lung Cancer: Opportunities for Translation to the Clinic, (Abstract).

(56) References Cited

OTHER PUBLICATIONS

Jiang et al., (2006) "Protective Role of FXR Activation in Diabetic Nephropathy", 39th Annual Meeting and Exposition of the American Society of Nephrology (ASN): Renal Week 2006 (Abstract).
Jiang et al., (2007) "FXR Modulates Renal Lipid Metabolism, Fibrosis, and Inflammation", 40th Annual Meeting and Exposition of the American Society of Nephrology (ASN): Renal Week 2007 (Abstract).
Jiang et al., (2009) "A Novel Bile Acid Receptor Agonist Prevents Diabetic Nephropathy", 42nd Annual Meeting and Exposition of the American Society of Nephrology (ASN): Renal Week 2009 (Abstract).
Jiang et al., (2014) "Intestinal Farsenoid X Receptor signaling promotes nonalcoholic fatty liver disease", The Journal of Clinical Investigation 125: 386-402.
Johansson, (2004) "Effects of the thyroid receptor-beta agonist, GC-1, on bile acid in intact male mice", 18th International Bile Acid Meeting: Bile Acid and Cholesterol Metabolism and its Therapeutic Implications (Abstract).
John et al., (2004) "18th International Bile Acid Meeting: Bile Acid and Cholesterol Metabolism and its Therapeutic Implications", (Abstract).
Johnson et al., Relationships between drug activity in NCI preclinical in vitro and in vivo models and early clinical trials, British Journal of Cancer (2001), 84(10), pp. 1424-1431. doi: 10.1054/bjoc.2001.1796, www.idealibrary.com.
Johnston, et al., (2013) "A New Therapy for Chronic Diarrhea? a Proof of Concept Study of the FXR Agonist Obeticholic Acid in Patients With Primary Bile Acid Diarrhea", 54th Annual Meeting at Digestive Disease Week (DDW 2013): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Journe et al., "Association between Farsenoid X Receptor expression and cell proliferation in estrogen receptor-positive luminal-like breast cancer from postmenopausal patients", Breast Cancer Res. Treat. 115(3): 523-534, 2009, doi: 10.1007/s10549-008-0094-2.
Journe et al., (2006) "Bone-Derived Lipid Stimulates MCF-7 Breast Cancer Cell Growth through Farsenoid X Receptor-Mediated Estrogen Receptor Activation", 28th Annual Meeting of the American Society for Bone and Mineral Research (ASBMR), (Abstract).
Journe et al., (2006) "Crosstalk between Farsenoid X Receptor and estrogen receptor might account for mitogenic effect of bone-derived lipids in bone metastasis from breast cancer", 6th International Meeting on Cancer Induced Bone Disease (CABS), (Abstract).
Journe et al., (2006) "Farnesol, an intermediate of the mevalonate pathway, stimulates MCF-7 breast cancer cell growth: evidence for a positive crosstalk between Farsenoid X Receptor and estrogen receptor", 29th Annual San Antonio Breast Cancer Symposium (SABCS), (Abstract).
Journe et al., (2006) "Farsenoid X Receptor: a new marker of poor prognosis in luminal subtype of breast carcinomas?", 29th Annual San Antonio Breast Cancer Symposium (SABCS), (Abstract).
Journe et al., (2007) "Activation of Farsenoid X Receptor in Breast Cancer Cell Lines by Bone-Derived Lipid", 29th Annual Meeting of the American Society for Bone and Mineral Research (ASBMR), (Abstract).
Journe et al., (2007) "Bone-derived lipids stimulate breast cancer cell growth through a crosstalk between Farsenoid X Receptor and estrogen receptor: in vitro and clinical data", 34th European Symposium on Calcified Tissues (ECTS), (Abstract).
Jung et al., (2004) "Reverse cholesterol transport in cholangiocytes is regulated by LXR", 55th Annual Meeting of the American Association for the Study of Liver Diseases (AASLD), (Abstract).
Jung et al., (2006) "PXR is a target of FXR", 16th International Symposium on Microsomes and Drug Oxidations (MDO), (Abstract).
Kainuma, M. et al., "Design, synthesis, and evaluation of non-steroidal Farsenoid X Receptor (FXR) antagonist", 2007, Bioorg. Med. Chem., 15, 2587-2600.

Kansy et al., "Physicochemical high throughput screening: parallel artificial membrane permeation assay in the description of passive absorption processes", J. Med. Chem. 41(7), 1007-1010, Mar. 26, 1998.
Kast et al., "Farnesoid X-Activated Receptor Induces Apolipoprotein C-II Transcription: a Molecular Mechanism Linking Plasma Triglyceride Levels to Bile Acids", Molecular Endocrinology, 5(10): 1720-1728, 2001.
Kast et al., "Regulation of Multidrug Resistance-associated Protein 2 (ABCC2) by the Nuclear Receptors Pregnane X Receptor, Farnesoid X-activated Receptor, and Constitutive Androstane Receptor", The Journal of Biological Chemistry, 277(4):2908-2915, 2002.
Katona et al., (2006) "Synthesis and Nuclear Receptor Agonistic/Antagonistic Profiles of Enantiomeric Bile Acids", 97th Annual Meeting and Expo of the American Oil Chemists Society Joint Symposium on Biosciences: A Global Business Forum on Fats, Oils, Surfactants, Lipids, and Related Materials (Abstract).
Kawamura. et al., (2012) "Functional Analysis of the Farsenoid X Receptor in Colorectal Cancer Cells", 35th Annual Meeting of Molecular Biology Society of Japan (MBSJ), (Abstract).
Keating et al., (2009) "Farsenoid X Receptor Activation Downregulates Chloride Secretion in Colonic Epithelial Cells", Digestive Disease Week 2009 (DDW), (Abstract).
Keating et al., (2010) "Farnesoid X-receptor Agonists Inhibit Colonic Secretion In Vitro and In Vivo", Digestive Disease Week 2010 (DDW), (Abstract).
Keitel et al., (2014) "TGR5: Pathogenetic Role and/or Therapeutic Target in Fibrosing Cholangitis?", Clinic Rev Allerg Immunol 48: 218-25.
Kennie et al., (2013) "Relative Potencies of Bile Acids in Inducing Fibroblast Growth Factor 19 in the Human Ileum", 54th Annual Meeting at Digestive Disease Week (DDW 2013): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Kerr et al., (2012) "Cysteine Sulfinic Acid Decarboxylase Regulation by Bile Acids: A Role for FXR and SHP in Hepatic Taurine Metabolism", 53rd Annual Meeting at Digestive Disease Week (DDW 2012): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Kim et al., "Spontaneous hepatocarcinogenesis in Farsenoid X Receptor-null mice", Carcinogenesis 28(5): 940-946, 2007.
Kim et al., (2014) "Therapeutic Targets and Management of Non-Alcoholic Steatohepatitis", 20th Annual Meeting of the Korean Association for the Study of the Liver (KASL) and Postgraduate Course—Liver Week (Abstract).
Kir et al., (2011) "FGF19 as a Postprandial, Insulin-Independent Activator of Hepatic Protein and Glycogen Synthesis", Science 331: 1621-4.
Klaman et al., (2007) "Potent FXR Agonist Decreases Triglyceride and Cholesterol Levels in Dyslipidemic Mice, but Does Not Lower Glycemia in Insulin Resistant Mouse Models", 67th Annual Meeting and Scientific Sessions of the American Diabetes Association (ADA), (Abstract).
Kliewer, (2006) "Coordinate Regulation of Bile Acid Homeostasis & Innate Immunity by the Nuclear Bile Acid Receptor", 88th Annual Meeting of the Endocrine Society (ENDO), (Abstract).
Komichi et al., (2004) "A Nuclear Receptor Ligand Down-Regulates Cytosolic Phospholipase A2 (cPLA2) Expression to Reduce bile Acid-Induced Cyclooxygenase 2 (COX-2) Activity in Cholangiocytes: Implication of Anti-Carcinogenic Action of Farsenoid X Receptor (FXR) Agonist", Digestive Disease Week 2004 (DDW): American Association for the Study of Liver Diseases, American Gastroenterological Association, American Society for Gastrointestinal Endoscopy, Society for Surgery of the Alimentary Tract (Abstract).
Kong et al., (2009) "Suppression of cyp7a1 gene transcription by FXR in mice is mediated through the intestineinitiated FGF15/FGFR4 pathway rather than the liver-initiated SHP/LRH1 path-

(56) References Cited

OTHER PUBLICATIONS way", 60th Annual Meeting of the American Association for the Study of Liver Diseases (AASLD), (Abstract).
Kong et al., (2011) "Differential Roles of Intestinal Fgf15 and Hepatic Shp in Feed-back Suppression of Cyp7a1 and Cyp8b1 Gene Transcription in Mice", 62nd Annual Meeting of the American Association for the Study of Liver Diseases (AASLD), (Abstract).
Kowdley et al., (2011) "An international study evaluating the Farsenoid X Receptor agonist obeticholic acid as monotherapy in PBC", 46th Annual Meeting of the European Association for the Study of the Liver (EASL), (Abstract).
Kowdley et al., (2014) "FXR Agonist Obeticholic Acid: Sustained Improvement in Markers of Cholestasis and Long-Term Safety in Patients with Primary Biliary Cirrhosis through 4 Years", 65th Annual Meeting and Postgraduate Course of the American Association for the Study of Liver Diseases (AASLD), (Abstract).
Kremoser et al., (2010) "FXR agonists as novel medication for metabolic syndrome and NASH", 16th World Congress of Basic and Clinical Pharmacology (WorldPharma 2010) of the International Union of Pharmacology (IUPHAR), (Abstract).
Kremoser et al., (2010) "Phenex Pharmaceuticals AG", Poster.
Kremoser et al., (2012) "FXR agonists prevent steatosis, hepatocyte death and progression of NASH towards hcc in a hypoinsulinaemic mouse model of progressive liver disease", 47th Annual Meeting of the European Association for the Study of the Liver (EASL), (Abstract).
Kremoser et al., (2012) "Synthetic FXR agonists improve liver histopathology and reduce liver tumor formation in mouse models of NASH and liver cancer", 22nd Conference of the Asian Pacific Association for the Study of the Liver (APASL), (Abstract).
Kumar et al., (2009) "Farsenoid X Receptor Agonist (GW4064) Protects the Kidney from Ischemic Acute Kidney Injury", 42nd Annual Meeting and Exposition of the American Society of Nephrology (ASN): Renal Week 2009 (Abstract).
Kunne et al., (2011) "Hepatic steatosis in mice lacking hepatic cytochrome p450 activity is bile salt dependent", 62nd Annual Meeting of the American Association for the Study of Liver Diseases (AASLD), (Abstract).
Kurata et al., (2011) Pathophysiological Role of Chenodeoxycholic Acid on Hepatic Disposition of Metformin via Organic Cation Transporter 1 in Acute Cholestasis, 2011 Annual Meeting of the American Association of Pharmaceutical Scientists (AAPS), (Abstract).
Lambert et al., "The Farnesoid X-receptor is an Essential Regulator of Cholesterol Homeostasis", The Journal of Biological Chemistry, 278, 2563-2570, 2003.
Lamers et al., (2012) "Structure and Ligand-Based Identification of Novel Synthetic Ligands for Farsenoid X Receptor", 22nd Biennial International Symposium on Medicinal Chemistry (EFMC-ISMC 2012), (Abstract).
Lamers et al., (2014) "Medicinal Chemistry and Pharmacological Effects of Farsenoid X Receptor (FXR) Antagonists", Current Topics in Medicinal Chemistry 14: 2188-2205.
Lamers et al., (2014) "Pyridinol/Pyridinon Tautomerism Determining Activity at Farsenoid X Receptor (FXR): New Agonistic or Antagonistic Ligands of FXR", 23rd International Symposium on Medicinal Chemistry (ISMC) held Jointly with the European Federation for Medicinal Chemistry (EFMC), (Abstract).
Lamers et al., (2014) "Pyridinol/Pyridinon-tautomerism determining activity at Farsenoid X Receptor: new agonistic or antagonistic ligands of FXR", 2014 Annual Meeting on Trends and Perspectives in Pharmaceutical Sciences (DPhG) Annual Meeting of the German Pharmaceutical Society (DPhG), (Abstract).
Lavine et al., (2014) "Association of Hepatic Nuclear Hormone Receptor Expression Profiles with Features of Hepatic Histology in Children with Nonalcoholic Fatty Liver Disease", 65th Annual Meeting and Postgraduate Course of the American Association for the Study of Liver Diseases (AASLD), (Abstract).
Lawson, J. et al.. "Diarylcyclobutane analogs of diethylstilbestrol", 1974, J. Med. Chem., 17, 383-386.

Leckie et al., (2009) "Modulation of the DDAH-ADMA pathway with the Farnesoid receptor (FXR) agonist INT-747 restores hepatic eNOS activity and lowers portal pressure in cirrhotic rats", 2009 Annual Meeting of the British Association for the Study of the Liver (BASL), (Abstract).
Leclercq, (2009) "Experimental therapies in NASH", 2009 European Association for the Study of Liver Special Conference: Non Alcoholic Fatty Liver Disease/Non Alcoholic Steato-Hepatitis (NAFLD/NASH) and Related Metabolic Disease (Abstract).
Lee et al., (2010) "FXR Positively Regulates Hepatic SIRT1 Levels Via MicroRNA-34a Inhibition", 92nd Annual Meeting of the Endocrine Society (ENDO), (Abstract).
Li et al., (2010) "Transgenicexpression of CYP7A1 in mouse livers promotes biliary cholesterol secretion via FXRdependent induction of hepatic ABCG5 and ABCG8 expression", 61st Annual Meeting of the American Association for the Study of Liver Diseases (AASLD), (Abstract).
Li et al., (2015) "Bile acids as metabolic regulators", Curr Opin Gastroenterol 31: 000-000.
Li et al., Farnesoid X Receptor Agonists as Therapeutic Target for Cardiometabolic Diseases, Frontiers in Pharmacology, vol. 11, Article 1247, 1-15 (Year: 2020).
Li et al., Bile Acids and Farnesoid X Receptor: Novel Target for the Treatment of Diabetic Cardiomyopathy, Current Protein Peptide Science, 20(10):976-983. (Year: 2019).
Lian et al., (2011) "Hepatoprotective effect of Farsenoid X Receptor on liver injury in systemic lupus erythematosus", 12th Annual European League Against Rheumatism (EULAR 2011), (Abstract).
Liebman et al., (2004) "PPAR-y Agonists Modulate Renal Lipid Metabolism and Prevent the Development of Glomerulosclerosis in Zucker Diabetic Fatty Rats", 37th Annual Meeting and Exposition of the American Society of Nephrology (ASN), (Abstract).
Liem et al., (2010) "Regulation of FXR transcriptional activity by AMPK", 2010 Nuclear Receptors: Signaling, Gene Regulation and Cancer (X7), (Abstract).
Lihong et al., (2006) "FXR Agonist, GW4064, Reverses Metabolic Defects in High-Fat Diet Fed Mice", 66th Annual Meeting and Scientific Sessions of the American Diabetes Association (ADA), (Abstract).
Lihong et al., American Diabetes Association (ADA) 66th annual scientific sessions, Jun. 2006, Abstract No. 856-P.
Lin, (2008) "Study of role of Farsenoid X Receptor in hepatocarcinoma cells", Biennial Shanghai—Hong Kong International Liver Congress 2008 (Abstract).
Liu et al., "Hepatoprotection by the Farsenoid X Receptor agonist GW4064 in rat models of intra- and extrahepatic cholestasis", The Journal of Clinical Investigation, 112, 1678-1687, 2003, doi: 10.1172/JCI200318945.
Liu et al., (2004) "Protection against cclinduced hepatic fibrosis by the Farsenoid X Receptor agonist GW4064 in rat", 55th Annual Meeting of the American Association for the Study of Liver Diseases (AASLD), (Abstract).
Loomba et al., (2015) "Polyunsaturated fatty acid metabolites as novel lipidomic biomarkers for noninvasive diagnosis of nonalcoholic steatohepatitis", Journal of Lipid Research 56: 2015.
Lu et al., "Molecular Basis for Feedback Regulation of Bile Acid Synthesis by Nuclear Receptors", Molecular Cell, 6, 507-515, 2000.
Luketic et al., (2014) "Efficacy of Obeticholic Acid In Primary Biliary Cirrhosis as Assessed by Response Criteria Associated With Clinical Outcome: A Poise Analysis", 65th Annual Meeting and Postgraduate Course of the American Association for the Study of Liver Diseases (AASLD), (Abstract).
Lundquist et al., (2010), "Improvement of Physiochemical Properties of the Tetrahydroazepinoindole Series of Farsenoid X Receptor (FXR) Agonists: Beneficial Modulation of Lipids in Primates", J. Med. Chem., 53:1774-1787.
Ma et al., "Farsenoid X Receptor is essential for normal glucose homeostasis", The Journal of Clinical Investigation, 116, 1102-1109, 2006, doi: 10.1172/JCI25604.
Ma et al., (2004) "The Role of Farsenoid X Receptor (FXR) in Glucose Metabolism", 86th Annual Meeting of the Endocrine Society (ENDO), (Abstract).

(56) References Cited

OTHER PUBLICATIONS

Makishima et al., "Identification of a Nuclear Receptor for Bile Acids", Science, 284,:1362-1365, 1999.
Maloney et al., "Identification of a Chemical Tool for the Orphan Nuclear Receptor FXR", Journal of Medicinal Chemistry, 43, 2971-2974, 2000.
Maloney et al., "Identification of a Chemical Tool for the Orphan Nuclear Receptor FXR", Journal of Medicinal Chemistry, Supporting Info Page, 6 pages, 2000.
Maneschi et al., (2013) "The FXR agonist obeticholic acid normalizes lipid droplet and triglyceride handling in visceral adipose tissue preadipocytes from a non-genomic rabbit model of metabolic syndrome", 16th European Congress of Endocrinology (ECE), (Abstract).
Mangelsdorf et al., "The Nuclear Receptor Superfamily: The Second Decade", Cell, 83, 835-839, 1995.
Mangelsdorf, (2005) "The Contrasting Roles of LXRs and FXR in Lipid Metabolism", Bioactive Lipids, Lipidomics and their Targets (Z1), (Abstract).
Mangelsdorf, (2006) "Nuclear receptors and transcriptional control of lipid metabolism", 197th Annual Meeting of the Society for Endocrinology (Abstract).
Maran et al., "FXR Deficiency in Mice Leads to Increased Intestinal Epithelial Cell Proliferation and Tumor Development", American Society for Pharmacology and Experimental Therapeutics, Published on Nov. 3, 2008 as DOI: 10.1124/jpet.108.145409, 35 pages.
Marinozzi et al., (2014) "Medicinal Chemistry of Farsenoid X Receptor (FXR) Modulators: The-State-of-the-Art", Current Topics in Medicinal Chemistry 14(19): 2127-2128.
Martinez-Fernandez et al., (2008) "Specific down-regulation of the bile acid sensor FXR by silencing ATP8B1 in HepG2 cells. Effect of the FXR agonist GW4064", 3rd World Congress of Pediatric Gastroenterology, Hepatology and Nutrition (WCPGHAN) held jointly with the 41st Annual Meeting of the European Society for Pediatric Gastroenterology, Hepatology and Nutrition (ESPGHAN), (Abstract).
Maruyama et al., (2010) "Selective anti-androgens with a 3,3-diphenylpentane skeleton", 2010 International Chemical Congress of Pacific Basin Societies (PACIFICHEM 2010), (Abstract).
Marzolini et al., (2004) "Unexpected Complexity in Nuclear Receptor Activation by HIV Protease Inhibitors and Induction of CYP Enzymes and Transporters", 2004 Annual Meeting and Science Innovation Exposition of The American Association for the Advancement of Science (Abstract).
Mason et al., (2010) "Farnesoid-X Receptor Agonists: a New Class of Drugs for the Treatment of PBC? An International Study Evaluating the Addition of Obeticholic Acid (INT-747) to Ursodeoxycholic Acid", 61st Annual Meeting of the American Association for the Study of Liver Diseases (AASLD), (Abstract).
Matsumura et al., "Palladium-Catalyzed Asymmetric Arylation, Vinylation, and Allenylation of Tert-cyclobutanols via Enantioselective C—C Bond Cleavage", 2003, J. Am. Chem. Soc., 125, 8862-8869.
Matsuzaki et al., (2012) "FXR Activation Promotes CDX2 Degradation via the Ubiquitin-Proteosome System with Upregulation of microRNA-221/222 in Human Esophageal Cells", 5th Annual International Gastrointestinal Consensus Symposium (IGICS), (Abstract).
McMahan et al., (2009) "FXR and TGR5 activation improves nonalcoholic fatty liver disease (nafld) and increases intrahepatic myeloid suppressor cells", 60th Annual Meeting of the American Association for the Study of Liver Diseases (AASLD), (Abstract).
McMahan et al., (2011) "Bile-Acid Receptor Activation Shifts Hepatic Monocytes/Macrophages Towards an Anti-Inflammatory Phenotype and Improves Non-Alcoholic Fatty Liver Disease", 62nd Annual Meeting of the American Association for the Study of Liver Diseases (AASLD), (Abstract).
McMahan et al., (2014) "Downregulation of pro-fibrotic and pro-inflammatory genes in liver sinusoidal endothelial cells following activation of the bile acid receptors FXR and TGR5", 65th Annual Meeting and Postgraduate Course of the American Association for the Study of Liver Diseases (AASLD), (Abstract).
McMillin et al., (2014) "Central expression of the hypothalamic neuropeptide galanin is upregulated in rodent models of primary sclerosing cholangitis", 65th Annual Meeting and Postgraduate Course of the American Association for the Study of Liver Diseases (AASLD), (Abstract).
McNulty et al., (2007) "FXR Plays A Major Role In Cholic Acid Mediated Effects In High-fat Diet Fed Mice", 67th Annual Meeting and Scientific Sessions of the American Diabetes Association (ADA), (Abstract).
Meech et al., (2014) "UDP-glycosyltransferase 8 (UGT8) galactosidates bile acids and modulates FXR signalling", 2014 Joint Scientific Meeting of the Australasian Society of Clinical and Experimental Pharmacologists and Toxicologists (ASCEPT) and the Molecular Pharmacology of GPCRs (MPGPCR), (Abstract).
Mencarelli et al., (2009) "FXR Activation Corrects Immune-Dysfunction and Attenuates Inflammation in a Rodent Model of Hepatitis", Digestive Disease Week 2009 (DDW), (Abstract).
Menendez et al., (2014) "The effects of bile acids on intestinal antimicrobial peptides expression", 2014 Annual Meeting of the Canadian Association of Gastroenterology (CAG) held jointly with the Canadian Association for the Study of the Liver (CASL): Canadian Digestive Disease Week (CDDW), (Abstract).
Merk et al., (2012) "Medicinal chemistry of Farsenoid X Receptor ligands: from agonists and antagonists to modulators", Future Med. Chem. 4(8), 1015-1036.
Merk et al., (2014) "Development of partial Farsenoid X Receptor (FXR) agonists", 2014 Annual Meeting on Trends and Perspectives in Pharmaceutical Sciences (DPhG) Annual Meeting of the German Pharmaceutical Society (DPhG), (Abstract).
Merk et al., (2014) "Development of Partial Farsenoid X Receptor (FXR) Agonists", 23rd International Symposium on Medicinal Chemistry (ISMC) held Jointly with the European Federation for Medicinal Chemistry (EFMC), (Abstract).
Miyata et al., "Role of Farsenoid X Receptor in the Enhancement of Canalicular Bile Acid Output and Excretion of Unconjugated Bile Acids: A Mechanism for Protection against Cholic Acid-Induced Liver Toxicity", The Journal of Pharmacology and Experimental Therapeutics, 312: 759-766, 2005.
Miyazaki et al., (2013) "Deoxycholic Acid Contributes to Chronic Kidney Disease-Dependent Vascular Calcification", 86th Annual Scientific Sessions of the American Heart Association (AHA 2013) and 2013 Resuscitation Science Symposium (RSS), (Abstract).
Modica et al., Nuclear Bile Acid Receptor FXR Protects against Intestinal Tumorigenesis, Cancer Res, 68, 9589-9594, Dec. 1, 2008.
Mohan et al., (2014) "Mechanism of FXR Mediated Apoptosis in Breast Cancer", 2014 Surrey Postgraduate Research Conference of the University of Surrey (Abstract).
Moloney et al., (2009) "The Effect of the Farsenoid X Receptor (FXR) and It's Agonist—GSK488062B—On Experimental Models of Colitis and Cytokine Production from IBD Tissue", Digestive Disease Week 2009 (DDW), (Abstract).
Mookerjee et al., (2014) "Effects of the FXR agonist obeticholic acid on hepatic venous pressure gradient (HVPG) in alcoholic cirrhosis: a proof of concept phase 2a study", 2014 International Liver Congress (ILC) and 49th annual meeting of the European Association for the Study of the Liver (EASL), (Abstract).
Moraes et al., (2009) "The nuclear receptor FXR as a novel regulator of platelet function", 22nd Biennial Congress of the International Society on Thrombosis and Haemostasis (ISTH) held jointly with the 55th Scientific and Standardisation Committee (SSC), (Abstract).
Moschetta et al., "Prevention of cholesterol gallstone disease by FXR agonists in a mouse model", Nature Medicine, 10, 1352-1358, 2004.
Moschetta et al., (2005) "The Role of LXRs and FXR in Enterohepatic Lipid Metabolism", Tissue-Selective Nuclear Receptors (D4), (Abstract).
Moscovitz et al., (2014) "Activation of the Farsenoid X Receptor Restores Hepatic and Intestinal Bile Acid Synthetic Enzyme and Transporter Expression in Pregnant Mice", 53rd Annual Meeting of the Society of Toxicology (SOT 2014), (Abstract).

(56) References Cited

OTHER PUBLICATIONS

Moussa et al., (2014) "Activation of Bile Acid Receptor (FXR) Attenuates Osteoclast Differentiation, Survival and Function", 60th Annual Meeting of the Orthopaedic Research Society (ORS 2014), (Abstract).
Moya et al., (2009) "Role of nuclear receptor ligands in fatty acid-induced hepatic steatosis", 2009 Joint Meeting of the European Association for the Study of the Liver (EASL) and the American Association for the Study of Liver Diseases (AASLD) Monothematic Conference: Nuclear Receptors and Liver Disease (Abstract).
Mroz et al., (2011) "The nuclear bile acid receptor, Farsenoid X Receptor, inhibits CFTR expression and Cisecretion in colonic epithelial cells", 2011 Annual Conference of the Physiological Society (Abstract).
Mroz et al., (2013) "Activation of the nuclear bile acid receptor, Farsenoid X Receptor, acutely regulates cAMPstimulated Cl-secretion in colonic epithelial cells", 2013 Physiological Society Joint Themed Meeting on Epithelia and Smooth Muscle Interactions in Health and Disease (Abstract).
Mroz et al., (2014) "Agonists of the nuclear bile acid receptor, FXR, prevent secretory diarrhea by a novel mechanism involving repression of CFTR promoter activity", 2014 Conference on Physiology—Physiological Society (Abstract).
Mudaliar et al., (2009) "Farnesoid-X receptor agonists—a new therapeutic class for diabetes and NAFLD—first clinical data", 45th Annual Meeting of the European Association for the Study of Diabetes (EASD), (Abstract).
Nejak-Bowen et al., (2013) "Novel therapeutic implications of modulating β-Catenin during intrahepatic cholestasis", 64th Annual Meeting and Postgraduate Course of the American Association for the Study of Liver Diseases (AASLD), (Abstract).
Nettles et al., "Ligand Control of Coregulator Recruitment to Nuclear Receptors", Annu. Rev. Physiol. 67, 09-333, 2005.
Neuschwander Tetri, (2015) "Targeting the FXR Nuclear Receptor to Treat Liver Disease", Division of Gastroenterology and Hepatology.
Neuschwander-Tetri et al., (2014) "Farnesoid X nuclear receptor ligand obeticholic acid for non-cirrhotic, non-alcoholic steatohepatitis (FLINT): a multicentre, randomised, placebo-controlled trial", The Lancet 385 (9972): 956-965.
Neuschwander-Tetri et al., Supplementary Appendix: Farnesoid-X nuclear receptor ligand obeticholic acid for non-cirrhotic, non-alcoholic steatohepatitis (FLINT): a multicentre, randomised, placebo-controlled trial. The Lancet 2014; published online Nov 7. dx.doi. org/10.1016/S0140-6736(14)61933-4.
Nevens et al., (2014) "An International Phase 3 Study of the FXR Agonist Obeticholic Acid in PBC Patients: Effects on Markers of Cholestasis Associated with Clinical Outcomes and Hepatocellular Damage", 65th Annual Meeting and Postgraduate Course of the American Association for the Study of Liver Diseases (AASLD), (Abstract).
Nevens et al., (2014) "The first primary biliary cirrhosis (PBC) phase 3 trial in two decades—an international study of the FXR agonist obeticholic acid in PBC patients", 2014 International Liver Congress (ILC) and 49th annual meeting of the European Association for the Study of the Liver (EASL), (Abstract).
Nijmeijer et al., (2009) "Genetic Variants of Farsenoid X Receptor (FXR) Predispose to Mortality and Infectious Complications in Acute Pancreatitis", Digestive Disease Week 2009 (DDW), (Abstract).
Ning et al., Nuclear Receptors in the Pathogenesis and Management of Inflammatory Bowel Disease, Hindawi Mediators of Inflammation, Article ID 2624941, 1-13. (Year: 2019).
Nolan et al., (2012) "The induction of FGF19 in human ileum by bile acids reflects their relative potencies as FXR-binding ligands", 20th Annual Meeting of the United European Gastroenterology Week (UEGW), (Abstract).
Nolan et al., (2014) "The Effects of Obeticholic Acid, a Farsenoid X Receptor Agonist, in Patients With Chronic Diarrhea Secondary to Crohn's Ileal Disease", 55th Annual Meeting at Digestive Disease Week (DDW 2014 ): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Opposition filed by Laboratorios Legrand S.A. for Colombian Patent Application No. NC2021/0009240 dated Nov. 19, 2021. 26 pages.
Parks et al., "Bile Acids: Natural Ligands for an Orphan Nuclear Receptor", Science, 284, 1365-1368, May 21, 1999.
Patani et al., Bioisosterism: A Rational Approach in Drug Design, Chemical Reviews, 1996, vol. 96, pp. 3147-3176.
Patel et al., "Cilofexor, a Nonsteroidal FXR Agonist, in Non-Cirrhotic Patients with Nonalcoholic Steatohepatitis: A Phase 2 Randomized Controlled Trial," Hepatology, vol. 72(1), 2020, pp. 58-71, first published Mar. 1, 2020.
Patman et al., (2014) "A variant of FGF19 protects the liver from cholestatic injury without inducing cancer", Nature Reviews Gastroenterology & Hepatology.
Payer et al., (2014) "The synthetic FXR agonist PX20606 attenuates bacterial translocation, intestinal inflammation, and reduces splanchnic blood flow in portal hypertensive mice", 47. Jahrestagung der Osterreichischen Gesellschaft fur Gastroenterologie und Hepatologie (OGGH) statt gemeinsam mit der 25. Lehrgang der Osterreichischen Gesellschaft fur Gastroenterologie und Hepatologie / 47th Annual Meeting of the Austrian Society for Gastroenterology and Hepatology held jointly with the 25th training course of the Austrian Society of Gastroenterology and Hepatology (Abstract).
Pedraz et al., (2012) "Transcription elongation factor TFIIS.1 gene is regulated by Farsenoid X Receptor", 37th Congress of Federation of the European Biochemical Societies (FEBS) held jointly with the 22nd Conference of the International Union of Biochemistry and Molecular Biology (IUBMB) and the Spanish Society of Biochemistry and Molecular Biology (SSBMB), (Abstract).
Pellicciari et al., "6a-Ethyl-Chenodeoxycholic Acid (6-ECDCA), a Potent and Selective FXR Agonist Endowed with Anticholestatic Activity", Journal of Medicinal Chemistry, 45. 3569-3572, Aug. 15, 2002.
Pellicciari, (2008) "Novel targets for metabolic diseases", Metabolic Disorders: From Bench to Bedside (Abstract).
Pellicciari, (2009) "Genomic and nongenomic bile acid receptors as novel targets for the treatment of metabolic disorders", 6th Biennial Joint Meeting of the European Federation for Medicinal Chemistry (EFMC), (Abstract).
Peng et al., (2012) "SRC-Mediated Cross-Talk Between Farnesoid X and Epidermal Growth Factor Receptors Inhibits Human Intestinal Cell Proliferation and Tumorigenesis", 53rd Annual Meeting at Digestive Disease Week (DDW 2012): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Penna et al., (2009) "Inhibition of experimental colitis by Farsenoid X Receptor agonists", 2009 European Congress of Immunology (ECI): 2nd Joint Meeting of European National Societies of Immunology under the Auspices of EFIS (Abstract).
Perttila et al., (2010) "Adiponutrin, a lipid droplet surface enzyme—evidence for regulation by ChREBP, SREBP1c and FXR in human hepatocytes", 46th Annual Meeting of the European Association for the Study of Diabetes (EASD), (Abstract).
Plass et al., "Farsenoid X Receptor and Bile Salts are Involved in Transcriptional Regulation of the Gene Encoding the Human Bile Salt Export Pump", Hepatology, 35, 589-596, Mar. 2002.
Porez et al., Bile acid receptors as targets for the treatment of dyslipidemia and cardiovascular disease, Journal of Lipid Research, 53, 1723-1737. (Year: 2012).
Poupon, (2007) "Targeting cholestasis", European Association for the Study of the Liver Monothematic Conference: Primary Biliary Cirrhosis (PBC), (Abstract).
Prentiss et al., (2008) "Characterization of transporter expression in primary cultures of human hepatocytes", 10th European Meeting of the International Society for the Study of Xenobiotics (ISSX), (Abstract).

(56) References Cited

OTHER PUBLICATIONS

Prough et al., (2014) "PCB regulation of hepatic nuclear receptors: Implications for hepatic steatosis", 5th Asia Pacific Regional Meeting of the International Society for the Study of Xenobiotics (ISSX 2014), (Abstract).
PubChem CID 132234195, retrieved from internet on Feb. 19, 2021. 8 pages.
PubChem CID 140823897, retrieved from internet on Feb. 19, 2021. 8 pages.
Qin et al., (2006) "Bile acids induces hypercholesterolemia through a FXR-independent mechanism in LDLR Knockout mice", Nuclear Receptors: Orphan Brothers (X3), (Abstract).
Qin et al., (2006) "Bile acis induce hypercholesterolemia through a FXR-independent mechanism in LDLR knockout mice", 14th International Symposium on Atherosclerosis (ISA), (Abstract).
Quiroga et al., (2012) "Deficiency of Carboxylesterase 1/Esterase-x Results in Obesity, Hepatic Steatosis, and Hyperlipidemia", Hepatology, 56 (6): 2188-2198.
Radreau et al., (2014) "Bile acids receptor FXR agonists repress HBV replication in HepaRG cell", 65th Annual Meeting and Postgraduate Course of the American Association for the Study of Liver Diseases (AASLD), (Abstract).
Ratziu et al., (2014) "Starting the battle to control non-alcoholic steatohepatitis", Institute for Cardiometabolism and Nutrition, Universite Pierre et Marie Curie, Assistance Publique Hopitaux de Paris.
Renga et al., (2009) "A Dark Side of FXR Activation in Cholestasis. FXR Is a Negative Regulator of MRP4", Digestive Disease Week 2009 (DDW), (Abstract).
Renga et al., (2012) "A Farnesoid-X-receptor (FXR)-Glucocorticoid Receptor (GR) Cascade Regulates Intestinal Innate Immunity in Response to FXR Activation", 53rd Annual Meeting at Digestive Disease Week (DDW 2012): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Renga et al., (2012) "Theonellasterol: a highly selective FXR antagonist that protects against liver injury in cholestasis", 34th National Conference of the Division of Organic Chemistry—Italian Chemical Society/ 34 Convegno Nazionale della Divisione di Chimica Organica—Societa Chimica Italiana (SCI), (Abstract).
Richter et al., (2011) "Discovery of novel and orally active FXR agonists for the potential treatment of dyslipidemia & diabetes", Bioorganic & Medicinal Chemistry Letters 21: 191-194.
Richter et al., (2011) "Optimization of a novel class of benzimidazole-based Farsenoid X Receptor (FXR) agonists to improve physicochemical and ADME properties", Bioorganic & Medicinal Chemistry Letters 21:1134-1140.
Ricketts et al., (2006) "The coffee diterpene, cafestol regulates cholesterol homeostasis from the intestine via FXR and FGF15", Nuclear Receptors: Orphan Brothers (X3), (Abstract).
Rizzo et al., "Role of FXR in Regulating Bile Acid Homeostasis and Relevance for Human Diseases", Current Drug Targets—Immune, Endocrine & Metabolic Disorders, 5, 289-303, 2005.
Rizzo et al., (2009) "INT-747: a Potent and Selective FXR Agonist Regulating Glucose Metabolism and Enhancing Insulin Secretion", 60th Annual Meeting of the American Association for the Study of Liver Diseases (AASLD), (Abstract).
Rizzo et al., (2009) "The Farsenoid X Receptor agonist int-747 enhances glucose-induced insulin secretion", 2009 Joint Meeting of the European Association for the Study of the Liver (EASL) and the American Association for the Study of Liver Diseases (AASLD) Monothematic Conference: Nuclear Receptors and Liver Disease (Abstract).
Rizzo et al., (2010) "Functional characterization of the semi-synthetic bile acid derivative INT-767, a dual FXR and TGR5 agonist", 16th World Congress of Basic and Clinical Pharmacology (WorldPharma 2010) of the International Union of Pharmacology (IUPHAR), (Abstract).
Rizzo et al., (2010) "Functional characterization of the semi-synthetic bile acid derivative INT-767, a dual FXR and TGR5 agonist", 45th Annual Meeting of the European Association for the Study of the Liver (EASL), (Abstract).
Rizzo et al., (2010) "Functional characterization of the semi-synthetic bile acid derivative INT-767, a dual FXR and TGR5 agonist", 61st Annual Meeting of the American Association for the Study of Liver Diseases (AASLD), (Abstract).
Rizzo et al., (2011) "Functional Characterization of the Semi-synthetic Bile Acid Derivative Int-767, a Dual FXR and TGR5 Agonist", 21st Conference of the Asian Pacific Association for the Study of the Liver (APASL), (Abstract).
Robitaille et al., (2008) "Role of the Farsenoid X Receptor (FXR) in intestinal epithelial cell growth and differentiation", 2008 Annual Meeting of the Canadian Digestive Disease Week (CDDW), (Abstract).
Saal et al., Pharmaceutical salts: A summary on doses of salt formers from the Orange Book, European Journal of Pharmaceutical Sciences 2013, vol. 49, No. 4, XP028676562, doi.org/10.1016/j.ejps.2013.05.026. 10 pages.
Sanyal et al., (2009) "A New Therapy for Nonalcoholic Fatty Liver Disease and Diabetes? INT-747—the First FXR Hepatic Therapeutic Study", 60th Annual Meeting of the American Association for the Study of Liver Diseases (AASLD), (Abstract).
Sanyal et al., (2013). "Novel therapeutic targets for alcoholic hepatitis", 14th Biennial Congress of the European Society for Biomedical Research on Alcoholism (ESBRA), (Abstract).
Sanyal, (2011) "Emerging Treatments of NASH", 21st Conference of the Asian Pacific Association for the Study of the Liver (APASL), (Abstract).
Sanz Ortega et al., (2012) "Effect of treatment with glucocorticoids FXR-mediated signaling pathway and bile acid homeostasis", 37th Congress of Federation of the European Biochemical Societies (FEBS) held jointly with the 22nd Conference of the International Union of Biochemistry and Molecular Biology (IUBMB) and the Spanish Society of Biochemistry and Molecular Biology (SEBBM), (Abstract).
Savkur et al., (2005) "Regulation of Pyruvate Dehydrogenase Kinase Expression by the Farsenoid X Receptor", Bioactive Lipids, Lipidomics and their Targets (Z1), (Abstract).
Schaap et al., (2006) "Evidence for regulation of human FGF19 gene expression by ileal FXR", 57th Annual Meeting of the American Association for the Study of Liver Diseases (AASLD), (Abstract).
Schaap et al., (2009) "FGF19 represses CYP7A1 through an ERK1/2-dependent pathway", 2009 Joint Meeting of the European Association for the Study of the Liver (EASL) and the American Association for the Study of Liver Diseases (AASLD) Monothematic Conference: Nuclear Receptors and Liver Disease (Abstract).
Schaap et al., (2014) "Bile acid receptors as targets for drug development", Nat. Rev. Gastroenterol. Hepatol. 11, 55-67.
Schena et al., "Mammalian Glucocorticoid Receptor Derivatives Enhance Transcription in Yeast", Science 241, 965-967, Aug. 19, 1988.
Schittenhelm et al., (2013) "Bile acids affect beta-cell function and glucose homeostasis by interference with the Farsenoid X Receptor (FXR)", 92nd Annual Meeting of the German Physiological Society/ Deutsche Physiologische Gesellschaft (DPG), (Abstract).
Schonewille et al., (2014) "Combination treatment of the novel pharmacological FXR-compound PX20606 and ezetimibe leads to massively increased neutral sterols excretion in mice", 82nd European Atherosclerosis Society Congress (EAS), (Abstract).
Schubert-Zsilavecz, (2014) "Medicinal chemistry of Farsenoid X Receptor ligands", 134th Annual Meeting of the Pharmaceutical Society of Japan (PSJ), (Abstract).
Schwabl et al., (2014) "The synthetic FXR agonist PX20606 attenuates bacterial translocation, intestinal inflammation, and reduces splanchnic blood flow in portal hypertensive mice", 2014 International Liver Congress (ILC) and 49th annual meeting of the European Association for the Study of the Liver (EASL), (Abstract).
Sepe et al., (2012) "Conicasterol E, a small heterodimer partner sparing farnesoid-X-receptor modulator endowed with a pregnane-X-receptor agonistic activity, from the marine sponge *Theonella swinhoei*", 34th National Conference of the Division of Organic

(56) References Cited

OTHER PUBLICATIONS

Chemistry—Italian Chemical Society/ 34 Convegno Nazionale della Divisione di Chimica Organica—Societa Chimica Italiana (SCI), (Abstract).
Shah et al., Emerging drugs for the treatment of non-alcoholic steatohepatitis: a focused review of farnesoid X receptor agonists, Expert Opinion on Emerging Drugs, 25 (3), 251-260. (Year: 2020).
Shapiro et al., (2009) "First human experience with a synthetic Farsenoid X Receptor (FXR) agonist—INT-747 (6-ethylchenodeoxycholic acid)", 2009 Joint Meeting of the European Association for the Study of the Liver (EASL) and the American Association for the Study of Liver Diseases (AASLD) Monothematic Conference: Nuclear Receptors and Liver Disease (Abstract).
Shapiro et al., (2009) "First Human Experience With A Synthetic Farsenoid X Receptor (FXR) Agonist-INT-747 (6a-Ethylchenodeoxycholic Acid)", 60th Annual Meeting of the American Association for the Study of Liver Diseases (AASLD), (Abstract).
Sinal et al., "Targeted Disruption of the Nuclear Receptor FXR/BAR Impairs Bile Acid and Lipid Homeostasis", Cell 102:731-744, Sep. 15, 2000.
Singhal et al., "Drug polymorphism and dosage form design: a practical perspective", Advanced Drug Delivery Reviews, 2004, vol. 56, pp. 335-347.
Smalley Jr. et al., (2015) "Novel heterocyclic scaffolds of GW4064 as Farsenoid X Receptor agonists", Bioorganic & Medicinal Chemistry Letters 25: 280-284.
Song et al., (2008) "Bile Acids Activate Farsenoid X Receptor and Fibroblast Growth Factor 19 Signaling To Inhibit Cholesterol 7a-Hydroxylase Gene Expression in Human Hepatocytes", 90th Annual Meeting of the Endocrine Society (ENDO), (Abstract).
Soo Shin et al., (2013) "Positive regulation of osteogenesis by bile acid through FXR", 40th Annual Congress of the European Calcified Tissue Society (ECTS 2013), (Abstract).
Staels, (2006) "Nuclear receptors as therapeutic targets to modulate the metabolic syndrome", 31st International Meeting of the Federation of the European Biochemical Societies (FEBS), (Abstract).
Staels, (2009) "Bile acids: from simple detergents to complex signalling molecules controlling lipid and glucose homeostasis", 6th Annual Congress on Metabolic Syndrome, Type II Diabetes and Atherosclerosis (Abstract).
Stayrook et al., (2005) "Regulation of Carbohydrate Metabolism by the Farsenoid X Receptor", Bioactive Lipids, Lipidomics and their Targets (Z1), (Abstract).
Stayrook et al., Regulation of Carbohydrate Metabolism by the Farsenoid X Receptor, Endocrinology, 146, 984-991, 2005.
Stojancevic et al., The impact of farnesoid X receptor activation on intestinal permeability in inflammatory bowel disease, Can J Gastroenterol, 26(9), 631-637. (Year: 2012).
Suzuki et al., (2008) "Mechanism of regulation of bile acid transport in the small intestine", Falk Symposium 165: 20th International Bile Acid Meeting (Abstract).
Swales et al., "The Farsenoid X Receptor is Expressed in Breast Cancer and Regulates Apoptosis and Aromatase Expression", Cancer Res., 66, 10120-10126, Oct. 15, 2006.
Taiwanese Search Report for TW101123785, completed Jan. 16, 2013, 4 pages.
Takada et al., (2006) "Transcriptional regulation of mouse organic solute transporter alpha and beta by FXR and LXR alpha", Falk Symposium No. 155: XIX International Bile Acid Meeting—Bile Acids: Biological Actions and Clinical Relevance (Abstract).
Tanaka, A., Emerging novel treatments for autoimmune liver diseases, Hepatology Research, 49:489-499. (Year: 2019).
Tazuma et al., (2004) "A nuclear receptor ligand down-regulates cytosolic phospholipase AcPLA expression to reduce bile acid-induced cyclooxygenase 2 (COX-2) activity in cholangiocytes: Implication of anticarcinogenic action of Farsenoid X Receptor (FXR) agonist", Falk Symposium No. 141 Bile Acids and Cholesterol Metabolism and its Therapeutical Implications (Abstract).
Tazuma, (2004) "A nuclear receptor ligand down-regulates cytosolic phosphollpaseA2(cPLA2)expression to reduce bile acid-Induced cyclooxygenase 2 (COX-2) activity in cholangiocytes: Implication of anticarcinogenic action of farnesold X receptor (FXR) agonist", 18th International Bile Acid Meeting: Bile Acid and Cholesterol Metabolism and its Therapeutic Implications. (Abstract).
Tomlinson et al., "Transgenic Mice Expressing Human Fibroblast Growth Factor-19 Display Increased Metabolic Rate and Decreased Adiposity", Endocrinology, 143, 1741-1747, May 2002.
Trauner (2010) "Nuclear hormone receptors-biliary diseases", 2010 European Association for the Study of the Liver (EASL) Monothematic Conference: Signaling in the Liver, (Abstract).
Trauner (2014) "Bile acids as regulators of hepatic transport and metabolism in cholestatic and metabolic liver diseases", 20th International Symposium on Microsomes and Drug Oxidations, (Abstract).
Trauner (2014) "FXR VS PPAR Agonists: Competitors or fellow-combatants", 2014 European Association for the Study of the Liver (EASL) Monothematic Conference: Primary Biliary Cirrhosis (PBC), (Abstract).
Trauner et al., The Nonsteroidal Farnesoid X Receptor Agonist Cilofexor (GS-9674) Improves Markers of Cholestasis and Liver Injury in Patients With Primary Sclerosing Cholangitis, Hepatology 2019, vol. 70, No. 3, pp. 788-801, XP055702995.
Unsworth et al., (2014) "Non-genomic effects of nuclear receptors: Different mechanisms of regulation of outside-in signalling in platelets", 2nd European Platelet Group Conference (EUPLAN), (Abstract).
Uriarte et al., (2014) "Ileal FGF15 contributes to fibrosis-associated hepatocellular carcinoma development", International Journal of Cancer.
Urizar et al., "A Natural Product That Lowers Cholesterol as an Antagonist Ligand for FXR", Science, 296, 1703-1706, May 31, 2002.
Urizar et al., "The Farnesoid X-activated Receptor Mediates Bile Acid Activation of Phospholipid Transfer Protein Gene Expression", The Journal of Biological Chemistry, 275, 39313-39317, Dec. 15, 2000.
Vairappan et al., (2009) "Modulation of the DDAH-ADMA pathway with the Farnesoid receptor (FXR) agonist INT-747 restores hepatic eNOS activity and lowers portal pressure in cirrhotic rats", 2009 Annual Meeting of the British Association for the Study of the Liver, (Abstract).
Vairappan et al., (2009) "Modulation of the DDAH-ADMA pathway with the Farsenoid X Receptor (FXR) agonist INT-747 restores hepatic eNOS activity and lowers portal pressure in cirrhotic rats", 60th Annual Meeting of the American Association for the Study of Liver Diseases, (Abstract).
Vaquero et al., (2012) "Role of BCRP in FXR-induced chemoresistance in liver and intestinal cancer cells", 37th Congress of Federation of the European Biochemical Societies (FEBS) held jointly with the 22nd Conference of the International Union of Biochemistry and Molecular Biology (IUBMB) and the Spanish Society of Biochemistry and Molecular Biology, (Abstract).
Vassie et al., (2014) "Obeticholic Acid, a Farsenoid X Receptor Agonist, Reduces Bile Acid Synthesis in Patients With Primary Bile Acid Diarrhea", 55th Annual Meeting at Digestive Disease Week (DDW 2014): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Verbeke et al., (2013) "Obeticholic acid, a farnesoid-X receptor agonist, improves portal hypertension by two distinct pathways in cirrhotic rats", 64th Annual Meeting and Postgraduate Course of the American Association for the Study of Liver Diseases, (Abstract).
Verbeke et al., (2014) "Obeticholic acid, a Farnesoid-X receptor agonist, improves portal hypertension in cirrhotic rats", 26th Belgian Week of Gastroenterology, (Abstract).
Verbeke et al., (2014) "Obeticholic acid, a Farnesoid-X receptor agonist, reduces bacterial translocation and restores intestinal permeability in a rat model of cholestatic liver disease", 2014 International Liver Congress (ILC) and 49th annual meeting of the European Association for the Study of the Liver, (Abstract).

(56) References Cited

OTHER PUBLICATIONS

Verbeke et al., (2014) "Obeticholic acid, an FXR agonist, reduces bacterial translocation in experimental cholestasis", 26th Belgian Week of Gastroenterology, (Abstract).
Visschers et al., (2011) "FXR stimulation with INT-747 in a rat biliary drainage model protects from hepatocellular injury after loss of enterohepatic circulation", 2011 Annual Meeting of the British Association for the Study of the Liver, (Abstract).
Visschers et al., (2012) "Cholangiopathy is the trigger for intestinal failure associated liver disease through failure of cyp7a1 inhibition resulting from lack of FXR stimulation after biliary drainage in rats", 34th Annual Congress of the European Society for Clinical Nutrition and Metabolism, (Abstract).
Visschers et al., (2012) "FXR stimulation with INT-747 in a rat biliary drainage model protects from hepatocellular injury after loss of enterohepatic circulation", 47th Annual Meeting of the European Association for the Study of the Liver, (Abstract).
Vlasuk et al., (2007) "Introduction to mechanistic approaches to increasing high density lipoprotein cholesterol", 233rd National Meeting of the American Chemical Society (Abstract).
Voskoglou-Nomikos et al., Clinical Predictive Value of the in Vitro Cell Line, Human Xenograft, and Mouse Allograft Preclinical Cancer Models[1], Clinical Cancer Research, vol. 9, pp. 4227-4239, Sep. 15, 2003.
Wagner et al., (2007) "Absence of FXR Protects Mice from Bile-infarcts in Biliary Obstruction by Reduction of Bile Acid-Independent Bile Flow: Implications for Targeting FXR in Treatment of Cholestasis?", 42nd Annual Meeting of the European Association for the Study of the Liver, (Abstract).
Wagner et al., (2007) "Ursodeoxycholic acid (UDCA) stimulates intestinal fibroblast growth factor 15 (Fgf-15) expression independent of the Farsenoid X Receptor (FXR)", Digestive Disease Week 2007 (DDW): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Wang et al., "FXR: a metabolic regulator and cell protector", Cell Research 18(11): 1087-1095, 2008, doi: 10.1038/cr.2008.289.
Wang et al., (2007) "FXR Modulates Renal Lipid Metabolism and Fibrosis in Diabetic Nephropathy", 2007 Experimental Biology Annual Meeting (FASEB) held jointly with the 2007 Annual Meeting of the American Society for Investigative Pathology, (Abstract).
Wang et al., (2008) "FXR Agonist Modulates Renal Lipid Metabolism, Inflammation, Oxidative Stress and Fibrosis in Diet-induced Obesity and Renal Disease", 2008 Nuclear Receptors: Orphan Brothers, (Abstract).
Wang et al., (2009) "Farsenoid X Receptor Deficiency Accelerates Diabetic Nephropathy in Nephropathy-Resistant C57BL/6 Mice", 42nd Annual Meeting and Exposition of the American Society of Nephrology, (Abstract).
Wang et al., (2010) "Dual Bile Acid Receptors Agonist INT-767 Prevents Diabetic Nephropathy through Multiple Mechanisms", 43rd Annual Meeting and Exposition of the American Society of Nephrology, (Abstract).
Wang et al., (2014) "Treatment with the FXR-TGR5 dual agonist INT-767 decreases NAFLD-NASH in mice fed a Western diet", 65th Annual Meeting and Postgraduate Course of the American Association for the Study of Liver Diseases, (Abstract).
Watanabe et al., "Bile acids lower triglyceride levels via a pathway involving FXR, SHP, and SREBP-1c", The Journal of Clinical Investigation, 113, 1408-1418, May 2004.
Watanabe et al., (2006) "Bile acids induce energy expenditure by promoting intracellular thyroid hormone activation", Nature Publishing Group 439 (26): 484-489.
Watanabe et al., (2010) "Lowering bile acid pool size with an FXR agonist induces obesity and diabetes through the decrease of energy expenditure", 2010 Nuclear Receptors: Development, Physiology and Disease, (Abstract).
Watts, (2013) "Hepatic Steatosis, Dyslipoproteinaemia and Cardiometabolic Disease", 2013 Annual Scientific Meeting of the Australian Diabetes Educators Association (ADEA) and the Australian Diabetes Society (ADS), (Abstract).
Willson et al., "Chemical Genomics: Functional Analysis of Orphan Nuclear Receptors in the Regulation of Bile Acid Metabolism", Medicinal Research Reviews, 21, 513-522, 2001.
Winkler et al., (2012) "Transcriptional regulation of hepatic and extrahepatic glucuronidation in tgUGT1A WT mice in obstructive cholestasis (BDL) and by FXR agonist GW4064", 63rd Annual Meeting and Postgraduate Course of the American Association for the Study of Liver Diseases, (Abstract).
Wittenburg et al., "FXR and ABCG5/ABCG8 as Determinants of Cholesterol Gallstone Formation From Quantitative Trait Locus Mapping in Mice", Gastroenterology, 125, 868-881, Sep. 2003.
Xie et al., (2014) "Metabolites profiling identifies a key role of Farsenoid X Receptor for glucose metabolism in proliferating cells", 5th Asia Pacific Regional Meeting of the International Society for the Study of Xenobiotics (Abstract).
Xing et al., (2007) "Adrenal Expression of 3s-Hydroxysteroid Dehydrogenase Type II Is Regulated by the Farsenoid X Receptor (FXR, NR1H4)", 89th Annual Meeting of the Endocrine Society, (Abstract).
Xing et al., (2008) "FXR Induces Liver Hypertrophy Through the Homeobox Factor Hex", Digestive Disease Week 2008, (Abstract).
Xu et al., (2014) "The Role of Bile Acid Receptor FXR Activation on NHE8 Expression Regulation", 55th Annual Meeting at Digestive Disease Week, (Abstract).
Yamada et al., (2008) "Bile Acids Induce CDX2 Expression via Farsenoid X Receptor (FXR) in Barrett's Oesophagus", 16th Annual Meeting of the United European Gastroenterology Week, (Abstract).
Yan et al., The pathophysiological function of non-gastrointestinal farnesoid X receptor, Pharmacology & Therapeutics, 226, 107867, 1-16. (Year: 2021).
Yang et al., "Spontaneous Development of Liver Tumors in the Absence of the Bile Acid Receptor Farsenoid X Receptor", Cancer Res, 67, 863-867, Feb. 1, 2007.
Yingji et al., (2009) "Bile Acids Induce Expression of CDx2 and MUC2 in Normal Rat Gastric Epithelial Cells via Activation of Nuclear Receptor FXR—a Possible Mechanism of Intestinal Metaplasia in the Stomach", Digestive Disease Week 2009, (Abstract).
Yu et al., (2014) "A Novel Treatment for Liver Injury in Western Diet Mouse Models", 1st Annual In Silico Drug Discovery Conference, (Abstract).
Yu et al., (2014) "A novel treatment for liver injury in Western diet mouse models", 70th Annual Southwest Regional Meeting of the American Chemical Society, (Abstract).
Yu, L., Advanced Drug Delivery Reviews, 2001, 48, 27-42. doi: 10.1016/S0169-409X(01)00098-9 (Year: 2001).
Zhan et al., (2013) "Genome-wide binding and transcriptome analysis of human Farsenoid X Receptor in the liver", 2013 Experimental Biology Annual Meeting, (Abstract).
Zhan et al., (2014) "Genome-Wide Binding and Transcriptome Analysis of Human Farsenoid X Receptor in Primary Human Hepatocytes", PLOS One 9(9).
Zhang et al., "Activation of the nuclear receptor FXR improves hyperglycemia and hyperlipidemia in diabetic mice", PNAS 103(a): 1006-1011, Jan. 24, 2006.
Zhang et al., (2007) "FXR signaling in metabolic disease", FEBS Letters 582: 10-18.
Zhang et al., (2009) "Farsenoid X Receptor agonist WAY-362450 attenuatesliver inflammation and fibrosis in murine model of non-alcoholic steatohepatitis", Journal of Hepatology, 51: 380-388.
Zhang et al., (2010) "Identification of Novel Pathways That Control FXR-mediated Hypocholesterolemia", 2010 Nuclear Receptors: Development, Physiology and Disease (X8), (Abstract).
Zhang et al., (2010) "Identification of Novel Pathways that Control FXR-Regulated Cholesterol Homeostasis", 11th Annual Conference on Arteriosclerosis, Thrombosis and Vascular Biology, (Abstract).
Zhang et al., (2015) "GW4064, an agonist of Farsenoid X Receptor (FXR), represses CYP3A4 expression in human hepatocytes by inducing small heterodimer partner (SHP) expression", downloaded from dmd.aspetjournals.org at ASPET Journals on Mar. 10, 2015, 23 pages.

(56) References Cited

OTHER PUBLICATIONS

Zhou et al., PPARa-UGT axis activation represses intestinal FXR-FGF15 feedback signalling and exacerbates experimental colitis. Nature Communications 2014, 5:4573, 1-15.

Zollner et al., "Role of Nuclear Receptors in the Adaptive Response to Bile Acids and Cholestasis: Pathogenetic and Therapeutic Considerations", Molecular Pharmaceutics 3(3): 231-251, 2006.

Bucar et al., Disappearing Polymorphs Revisited, Angewandte Chemie International Edition, Jun. 1, 2015, vol. 54, No. 24, pp. 6972-6993, DOI: 10.1002/anie.201410356.

Evaluating the Safety, Tolerability, and Efficacy of GS-9674 in Participants with Nonalcoholic Steatohepatitis (NASH), NCT02854605, ClinicalTrials.gov, Aug. 3, 2016. 7 pages.

Extended European Search Report for European Application No. 22174957.5 dated Sep. 5, 2022. 11 pages.

History of Changes for Study: NCT02943460, ClinicalTrials.gov archive [online], Feb. 21, 2019, [Retrieved on Aug. 19, 2022], Internet: clinicaltrials.gov/ct2/history/NCT02943460?V_16=View#StudyPageTop. 13 pages.

RN: 2253764-93-9, STN on the Web REGISTRY database, Chemical Abstract RN, RN: 2253764-93-9, Dec. 9, 2018, printed Mar. 10, 2023. 2 pages.

Study to Evaluate the Safety, Tolerability, and Efficacy of Cilofexor in Adults With Primary Sclerosing Cholangitis Without Cirrhosis, NCT02943460, ClinicalTrials.gov, Oct. 24, 2016. 8 pages.

Yuki Kagobutsu Kessho Sakusei Handobukku—Genri to Nouhau—[Handbook for preparing crystals of organic compounds—Principle and know-how], Jul. 25, 2008, pp. 57-79.

*p < 0.05 vs. 1 mg/kg;  p < 0.05 vs 5 mg/kg; * p < 0.05 vs. 100 mg/kg; one outlier from the 10 mg/kg group of Example 3 due to >3 SD from mean.

SEQUENCE LISTING

```
<160> NUMBER OF SEQ ID NOS: 1

<210> SEQ ID NO 1
<211> LENGTH: 25
<212> TYPE: PRT
<213> ORGANISM: Artificial Sequence
<220> FEATURE:
<223> OTHER INFORMATION: Synthetic

<400> SEQUENCE: 1

Cys Pro Ser Ser His Ser Ser Leu Thr Glu Arg His Lys Ile Leu His
1               5                   10                  15

Arg Leu Leu Gln Glu Gly Ser Pro Ser
            20                  25
```

FXR (NR1H4) MODULATING COMPOUNDS

CROSS REFERENCE TO RELATED APPLICATIONS

This application is a continuation of U.S. patent application Ser. No. 17/217,781, filed Mar. 30, 2021, now abandoned, which is a continuation of U.S. patent application Ser. No. 16/989,335, filed Aug. 10, 2020, now U.S. Pat. No. 10,981,881, which is a continuation of U.S. patent application Ser. No. 16/541,073, filed Aug. 14, 2019, now U.S. Pat. No. 10,774,054, which is a continuation of U.S. patent application Ser. No. 15/618,666, filed Jun. 9, 2017, now U.S. Pat. No. 10,421,730, which claims the benefit under 35 U.S.C. § 119(e) to U.S. Provisional Application No. 62/349,490, filed Jun. 13, 2016, all of which are hereby incorporated by reference in their entireties.

SEQUENCE LISTING

The Sequence Listing associated with this application is provided in text format in lieu of a paper copy, and is hereby incorporated by reference into the specification. The name of the text file containing the Sequence Listing is 1165_PC_ST25.txt. The text file created on May 16, 2017, is about 550 bytes and submitted electronically via EFS-Web.

FIELD

The present disclosure relates to compounds which bind to the NR1H4 receptor (FXR) and act as agonists or modulators of FXR. The disclosure further relates to the use of the compounds for the treatment and/or prophylaxis of diseases and/or conditions through binding of said nuclear receptor by said compounds.

BACKGROUND

Multicellular organisms are dependent on advanced mechanisms of information transfer between cells and body compartments. The information that is transmitted can be highly complex and can result in the alteration of genetic programs involved in cellular differentiation, proliferation, or reproduction. The signals, or hormones, are often low molecular weight molecules, such as peptides, fatty acid, or cholesterol derivatives.

Many of these signals produce their effects by ultimately changing the transcription of specific genes. One well-studied group of proteins that mediate a cell's response to a variety of signals is the family of transcription factors known as nuclear receptors, hereinafter referred to often as "NR." Members of this group include receptors for steroid hormones, vitamin D, ecdysone, cis and trans retinoic acid, thyroid hormone, bile acids, cholesterol-derivatives, fatty acids (and other peroxisomal proliferators), as well as so-called orphan receptors, proteins that are structurally similar to other members of this group, but for which no ligands are known. Orphan receptors may be indicative of unknown signalling pathways in the cell or may be nuclear receptors that function without ligand activation. The activation of transcription by some of these orphan receptors may occur in the absence of an exogenous ligand and/or through signal transduction pathways originating from the cell surface.

In general, three functional domains have been defined in NRs. An amino terminal domain is believed to have some regulatory function. It is followed by a DNA-binding domain (hereinafter referred to as "DBD"), which usually comprises two zinc finger elements and recognizes a specific Hormone Responsive Element (hereinafter referred to as "HRE") within the promoters of responsive genes. Specific amino acid residues in the "DBD" have been shown to confer DNA sequence binding specificity. A ligand-binding-domain (hereinafter referred to as "LBD") is at the carboxy-terminal region of known NRs.

In the absence of hormone, the LBD appears to interfere with the interaction of the DBD with its HRE. Hormone binding seems to result in a conformational change in the NR and thus opens this interference. A NR without the LBD constitutively activates transcription but at a low level.

Coactivators or transcriptional activators are proposed to bridge between sequence specific transcription factors, and the basal transcription machinery and in addition to influence the chromatin structure of a target cell. Several proteins like SRC-1, ACTR, and Grip1 interact with NRs in a ligand enhanced manner.

Nuclear receptor modulators like steroid hormones affect the growth and function of specific cells by binding to intracellular receptors and forming nuclear receptor-ligand complexes. Nuclear receptor-hormone complexes then interact with a HRE in the control region of specific genes and alter specific gene expression.

The Farnesoid X Receptor alpha (hereinafter also often referred to as NR1H4 when referring to the human receptor) is a prototypical type 2 nuclear receptor which activates genes upon binding to a promoter region of target genes in a heterodimeric fashion with Retinoid X Receptor. The relevant physiological ligands of NR1H4 are bile acids. The most potent one is chenodeoxycholic acid (CDCA), which regulates the expression of several genes that participate in bile acid homeostasis. Farnesol and derivatives, together called farnesoids, are originally described to activate the rat orthologue at high concentration but they do not activate the human or mouse receptor. FXR is expressed in the liver, throughout the entire gastrointestinal tract including the esophagus, stomach, duodenum, small intestine, colon, ovary, adrenal gland and kidney. Beyond controlling intracellular gene expression, FXR seems to be also involved in paracrine and endocrine signalling by upregulating the expression of the cytokine Fibroblast Growth Factor 15 (rodents) or 19 (monkeys, humans A).

Although numerous FXR agonists are known, there is a need for improved FXR agonists.

SUMMARY

The present disclosure provides compounds bind to the NR1H4 receptor (FXR) and act as agonists or modulators of FXR. The disclosure further relates to the use of the compounds for the treatment and/or prophylaxis of diseases and/or conditions through binding of said nuclear receptor by said compounds.

The present disclosure provides compounds according to Formula (I):

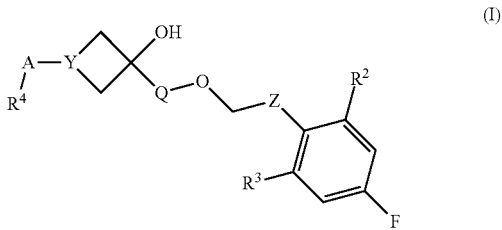

wherein:
- Q is phenylene or pyridylene, each of which is optionally substituted with one or two substituents independently selected from halogen, methyl, $C_{1-4}$-alkoxy, halo-$C_{1-4}$-alkoxy, —$CH_2F$, —$CHF_2$, and —$CF_3$;
- Y is N or CH;
- A is pyridylene or phenylene, each of which is optionally substituted with one or two groups independently selected from halogen, $C_{1-4}$-alkoxy, halo-$C_{1-4}$-alkoxy, $C_{1-4}$-alkyl, and halo-$C_{1-4}$-alkyl;
- Z is isoxazole substituted with $R^1$ or pyrazole substituted with $R^1$;
- $R^1$ is $C_{1-4}$-alkyl or $C_{3-6}$-cycloalkyl, wherein
  - said $C_{1-4}$-alkyl is optionally substituted with 1 to 3 substituents independently selected from fluoro, hydroxyl, $C_{1-3}$-alkoxy, and fluoro-$C_{1-3}$-alkoxy, and
  - said $C_{3-6}$-cycloalkyl is optionally substituted with 1 to 3 substituents independently selected from fluoro, hydroxyl, $C_{1-3}$-alkyl, fluoro-$C_{1-3}$-alkyl, $C_{1-3}$-alkoxy, and fluoro-$C_{1-3}$-alkoxy;
- $R^2$ and $R^3$ are independently selected from hydrogen, halogen, methoxy, —$CF_3$, —$CHF_2$, —$CH_2F$, —$OCH_2F$, —$OCHF_2$, —$OCF_3$, and methyl;
- $R^4$ is —$CO_2R^5$ or —$C(O)NR^5R^6$;
- $R^5$ is hydrogen, $C_{1-6}$-alkyl, or halo-$C_{1-6}$-alkyl; and
- $R^6$ is hydrogen or $C_{1-6}$-alkyl, wherein said $C_{1-6}$-alkyl is optionally substituted with 1 to 6 substituents independently selected from halogen, —$SO_3H$, and —$CO_2H$;

or a pharmaceutically acceptable salt, a stereoisomer, a mixture of stereoisomers, or a tautomer thereof.

Some embodiments provide for pharmaceutical compositions comprising a compound of formula (I) and a pharmaceutically acceptable excipient.

Also provided herein are methods of treating a patient having an FXR mediated condition comprising administering a compound of formula (I) to a patient in need thereof.

DETAILED DESCRIPTION

Definitions

Figure 1:
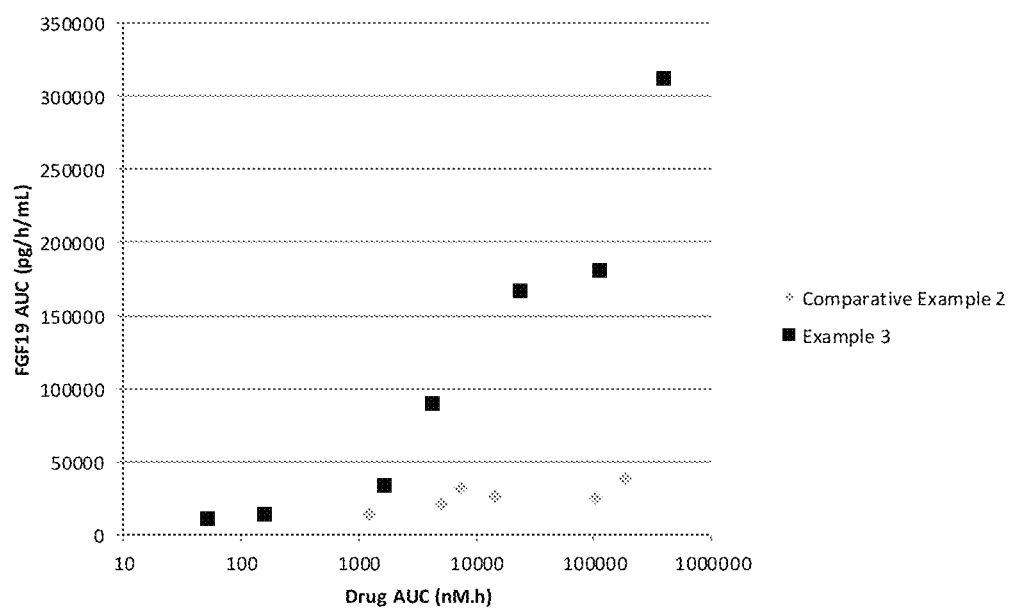
FIG. 1: Plasma exposure of Example 3 and Comparative Example 2 versus plasma FGF19 levels in cynomolgus monkey.

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

A dash ("-") that is not between two letters or symbols is used to indicate a point of attachment for a substituent. For example, —$C(O)NH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

In the context of the present disclosure "alkyl" means a saturated hydrocarbon chain, which may be straight chained or branched. In the context of the present disclosure, "$C_{1-6}$-alkyl" means a saturated alkyl chain having 1 to 6 carbon atoms which may be straight chained or branched. Examples thereof include methyl, ethyl, propyl, isopropyl, n-butyl, isobutyl, tert-butyl, n-pentyl, isopentyl, neopentyl and n-hexyl.

The term "haloalkyl" means that one or more hydrogen atoms in the alkyl chain are replaced by a halogen. A non-limiting example thereof is $CF_3$.

A "cycloalkyl" group means a saturated or partially unsaturated mono-, bi- or spirocyclic hydrocarbon ring system.

An "alkoxy" group refers to —O-alkyl, wherein alkyl is as defined herein. Examples of alkoxy groups include methoxy, ethoxy, n-propoxy, iso-propoxy, n-butoxy, tert-butoxy, sec-butoxy, n-pentoxy, n-hexoxy, and 1,2-dimethyl-butoxy.

"Halogen" or "halo" refers to a F, Cl, Br, or I atom.

"Hydroxyl" or "hydroxy" refers to —OH.

"Haloalkoxy" refers to an alkoxy group as defined herein wherein one or more hydrogen atoms in the alkyl chain are replaced by a halogen.

"Fluoroalkyl" refers to an alkyl group as defined herein wherein one or more hydrogen atoms in the alkyl chain are replaced by fluoro.

"Fluoroalkoxy" refers to an alkoxy group as defined herein wherein one or more hydrogen atoms in the alkyl chain are replaced by fluoro.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

Furthermore, the compounds of the present disclosure may be subject to tautomerism. Where tautomerism, e.g. keto-enol tautomerism, of compounds of the present disclosure or their prodrugs may occur, the individual forms, like e.g. the keto and enol form, are each within the scope of the disclosure as well as their mixtures in any ratio. The same applies for stereoisomers, like e.g. enantiomers, cis/trans isomers, conformers and the like.

The term "protecting group" refers to a moiety of a compound that masks or alters the properties of a functional group or the properties of the compound as a whole. Chemical protecting groups and strategies for protection/deprotection are well known in the art. See e.g., Protective Groups in Organic Chemistry, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. The term "deprotecting" refers to removing the protecting group.

A "leaving group" includes a molecular fragment that can depart with a pair of electrons from a covalent bond to the reacting carbon atom during a chemical reaction.

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

In some embodiments, the compounds of the present disclosure can be in the form of a "prodrug." The term "prodrug" is defined in the pharmaceutical field as a biologically inactive derivative of a drug that upon administration to the human body is converted to the biologically active parent drug according to some chemical or enzymatic pathway. Examples of prodrugs include esterified carboxylic acids.

In the human liver, UDP-glucuronosyltransferases act on certain compounds having amino, carbamyl, thio (sulfhydryl) or hydroxyl groups to conjugate uridine diphosphate-α-D-glucuronic acid through glycoside bonds, or to esterify compounds with carboxy or hydroxyl groups in the process of phase II metabolism. Compounds of the present disclosure may be glucuronidated, that is to say, conjugated to glucuronic acid, to form glucuronides, particularly (β-D) glucuronides.

One step in the formation of bile is the conjugation of the individual bile acids with an amino acid, particularly glycine or taurine. Compounds of the present disclosure may be conjugated with glycine or taurine at a substitutable position.

The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. In case the compounds of the present disclosure contain one or more acidic or basic groups, the disclosure also comprises their corresponding pharmaceutically or toxicologically acceptable salts, in particular their pharmaceutically utilizable salts. Thus, the compounds of the present disclosure which contain acidic groups can be present on these groups and can be used according to the disclosure, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present disclosure which contain one or more basic groups, i.e. groups which can be protonated, can be present and can be used according to the disclosure in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present disclosure simultaneously contain acidic and basic groups in the molecule, the disclosure also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present disclosure also includes all salts of the compounds of the present disclosure which, owing to low physiological compatibility, are not directly suitable for use in pharmaceuticals but which can be used, for example, as intermediates for chemical reactions or for the preparation of pharmaceutically acceptable salts.

Further the compounds of the present disclosure may be present in the form of solvates, such as those which include as solvate water, or pharmaceutically acceptable solvates, such as alcohols, in particular ethanol. A "solvate" is formed by the interaction of a solvent and a compound.

In certain embodiments, provided are optical isomers, racemates, or other mixtures thereof of the compounds described herein or a pharmaceutically acceptable salt or a mixture thereof. If desired, isomers can be separated by methods well known in the art, e.g. by liquid chromatography. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high pressure liquid chromatography (HPLC) column.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another. "Diastereomers" are stereoisomers that have at least two asymmetric atoms, but which are not mirror-images of each other.

The compounds disclosed herein and their pharmaceutically acceptable salts may include an asymmetric center and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

The disclosure also includes "deuterated analogs" of compounds of Formula (I) in which from 1 to n hydrogens attached to a carbon atom is/are replaced by deuterium, in which n is the number of hydrogens in the molecule. Such compounds may exhibit increased resistance to metabolism and thus be useful for increasing the half-life of any compound of Formula I when administered to a mammal, e.g. a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Furthermore, the present disclosure provides pharmaceutical compositions comprising at least one compound of the present disclosure, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing at least one compound of the present disclosure and a pharmaceutically acceptable carrier.

LIST OF ABBREVIATIONS AND ACRONYMS

| Abbreviation | Meaning |
| --- | --- |
| (±)-BINAP | (±)-2,2'-Bis(diphenylphosphino)-1,1'-binaphthalene |
| 2-MeTHF | 2-methyl tetrahydrofuran |
| ACN or MeCN | Acetonitrile |
| aq. | aqueous |
| Bn | Benzyl |
| BOC or Boc | t-Butyloxycarbonyl |
| BSA | Bovine serum albumin |
| BSS | Balanced Salt Solution |
| calcd | calculated |
| DAST | (diethylamino)sulfur trifluoride |
| DCM | Dichloromethane |
| DIBAL-H | Diisobutylaluminum hydride |
| DMF | Dimethylformamide |
| DMSO | Dimethylsulfoxide |
| EA | Ethyl acetate |
| EDTA | Ethylenediaminetetraacetic acid |
| ESI | Electronspray Ionization |
| Et | Ethyl |
| Et$_2$O | Diethyl ether |
| EtOAc | Ethyl acetate |
| FBS | Fetal bovine serum |
| h or hr(s) | Hour(s) |
| HATU | 1-[Bis(dimethylamino)methylene]-1H-1,2,3-triazolo[4,5-b]pyridinium 3-oxid hexafluorophosphate |
| HPLC | High performance liquid chromatography |
| IPA | Isopropyl alcohol |
| IPTG | Isopropyl β-D-1-thiogalactopyranoside |
| LCMS or LC/MS | Liquid Chromatography Mass Spectrometry |
| Me | Methyl |
| MEM | Minimum Essential Medium |
| MeOH | Methanol |
| min | Minute(s) |
| MS | Mass Spectrometry |
| m/z | Mass-to-charge ratio |
| NADPH | Dihydronicotinamide-adenine dinucleotide phosphate |

-continued

| Abbreviation | Meaning |
| --- | --- |
| NMP | N-methylpyrrolidone |
| NMR | Nuclear Magnetic Resonance spectroscopy |
| n-BuLi | n-butyllithium |
| rpm | Revolutions per minute |
| PE | Petroleum ether |
| RT or rt | Room temperature |
| sat. | saturated |
| TBAF | Tetrabutylammonium fluoride |
| TBDMS | t-butyldimethylsilyl |
| TBS | t-butyldimethylsilyl |
| TEMPO | 2,2,6,6-Tetramethylpiperidine 1-oxyl |
| TFA | Trifluoroacetic acid |
| THF | tetrahydrofuran |
| TMS | trimethylsilyl |
| UPLC | Ultra Performance Liquid Chromatography |

Compounds

Provided herein are compounds according to Formula (I):

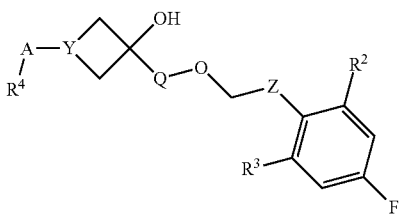

(I)

wherein:
- Q is phenylene or pyridylene, each of which is optionally substituted with one or two substituents independently selected from halogen, methyl, $C_{1-4}$-alkoxy, halo-$C_{1-4}$-alkoxy, —$CH_2F$, —$CHF_2$, and —$CF_3$;
- Y is N or CH;
- A is pyridylene or phenylene, each of which is optionally substituted with one or two groups independently selected from halogen, $C_{1-4}$-alkoxy, halo-$C_{1-4}$-alkoxy, $C_{1-4}$-alkyl, and halo-$C_{1-4}$-alkyl;
- Z is isoxazole substituted with $R^1$ or pyrazole substituted with $R^1$;
- $R^1$ is $C_{1-4}$-alkyl or $C_{3-6}$-cycloalkyl, wherein
  said $C_{1-4}$-alkyl is optionally substituted with 1 to 3 substituents independently selected from fluoro, hydroxyl, $C_{1-3}$-alkoxy, and fluoro-$C_{1-3}$-alkoxy, and
  said $C_{3-6}$-cycloalkyl is optionally substituted with 1 to 3 substituents independently selected from fluoro, hydroxyl, $C_{1-3}$-alkyl, fluoro-$C_{1-3}$-alkyl, $C_{1-3}$-alkoxy, and fluoro-$C_{1-3}$-alkoxy;
- $R^2$ and $R^3$ are independently selected from hydrogen, halogen, methoxy, —$CF_3$, —$CHF_2$, —$CH_2F$, —$OCH_2F$, —$OCHF_2$, —$OCF_3$, and methyl;
- $R^4$ is —$CO_2R^5$ or —$C(O)NR^5R^6$;
- $R^5$ is hydrogen, $C_{1-6}$-alkyl, or halo-$C_{1-6}$-alkyl; and
- $R^6$ is hydrogen or $C_{1-6}$-alkyl, wherein said $C_{1-6}$-alkyl is optionally substituted with 1 to 6 substituents independently selected from halogen, —$SO_3H$, and —$CO_2H$;

or a pharmaceutically acceptable salt, a stereoisomer, a mixture of stereoisomers, or a tautomer thereof.

One embodiment provides for compounds of Formula (Ia):

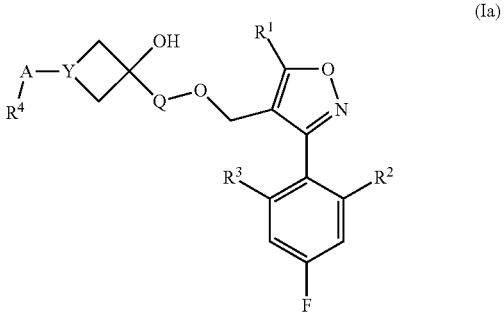

(Ia)

wherein:
- Q is phenylene or pyridylene, each of which is optionally substituted with one or two substituents independently selected from halogen, methyl, $C_{1-4}$-alkoxy, halo-$C_{1-4}$-alkoxy, —$CH_2F$, —$CHF_2$, and —$CF_3$;
- Y is N or CH;
- A is pyridylene or phenylene, each of which is optionally substituted with one or two groups independently selected from halogen, $C_{1-4}$-alkoxy, halo-$C_{1-4}$-alkoxy, $C_{1-4}$-alkyl, and halo-$C_{1-4}$-alkyl;
- $R^1$ is $C_{1-4}$-alkyl or $C_{3-6}$-cycloalkyl, wherein
  said $C_{1-4}$-alkyl is optionally substituted with 1 to 3 substituents independently selected from fluoro, hydroxyl, $C_{1-3}$-alkoxy, and fluoro-$C_{1-3}$-alkoxy, and
  said $C_{3-6}$-cycloalkyl is optionally substituted with 1 to 3 substituents independently selected from fluoro, hydroxyl, $C_{1-3}$-alkyl, fluoro-$C_{1-3}$-alkyl, $C_{1-3}$-alkoxy, and fluoro-$C_{1-3}$-alkoxy;
- $R^2$ and $R^3$ are independently selected from hydrogen, halogen, methoxy, —$CF_3$, —$CHF_2$, —$CH_2F$, —$OCH_2F$, —$OCHF_2$, —$OCF_3$, and methyl;
- $R^4$ is —$CO_2R^5$ or —$C(O)NR^5R^6$;
- $R^5$ is hydrogen, $C_{1-6}$-alkyl, or halo-$C_{1-6}$-alkyl;
- $R^6$ is hydrogen or $C_{1-6}$-alkyl, wherein said $C_{1-6}$-alkyl is optionally substituted with 1 to 6 substituents independently selected from halogen, —$SO_3H$, and —$CO_2H$;

or a pharmaceutically acceptable salt, a stereoisomer, a mixture of stereoisomers, or a tautomer thereof.

One embodiment provides for compounds of formula (Ia):

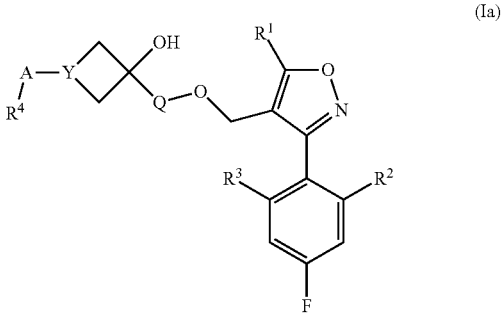

(Ia)

wherein:
- Q is phenylene optionally substituted with one or two halogen;
- Y is N or CH;

A is pyridylene optionally substituted with one or two groups independently selected from halogen and $C_{1-4}$-alkoxy;

$R^1$ is $C_{1-4}$-alkyl or $C_{3-6}$-cycloalkyl;

$R^2$ and $R^3$ are independently selected from hydrogen and halogen;

$R^4$ is $—CO_2R^5$ or $—C(O)NR^5R^6$;

$R^5$ is hydrogen; and $R^6$ is $C_{1-2}$-alkyl optionally substituted with $—CO_2H$ or $—SO_3H$;

or pharmaceutically acceptable salt, a stereoisomer, a mixture of stereoisomers, or a tautomer thereof.

In one embodiment, Q is phenylene or pyridylene, each of which is optionally substituted with one or two substituents independently selected from halogen, methyl, $—CHF_2$, and $—CF_3$. In some embodiments, Q is phenylene optionally substituted with one or two substituents independently selected from halogen, methyl, and $—CF_3$. In some embodiments, Q is pyridylene optionally substituted with one or two substituents independently selected from halogen, methyl, and $—CF_3$.

In one embodiment, Q is phenylene optionally substituted with one or two halogen. In some embodiments, Q is pyridylene optionally substituted with one or two halogen. In some embodiments, Q is phenylene optionally substituted with one or two chloro. In some embodiments, Q is pyridylene optionally substituted with one or two chloro.

In one embodiment, Q is phenylene substituted with one chloro. In some embodiments, Q is pyridylene substituted with one chloro.

In one embodiment, $R^1$ is $C_{1-4}$-alkyl. In some embodiments, $R^1$ is $C_{3-6}$-cycloalkyl. In some embodiments, $R^1$ is cyclopropyl or methyl. In some embodiments, $R^1$ is cyclopropyl.

In one embodiment, $R^2$ and $R^3$ are not both hydrogen. In some embodiments, $R^2$ and $R^3$ are independently selected from hydrogen, halogen, methoxy, $—OCHF_2$, $—OCF_3$, and methyl. In some embodiments, $R^2$ and $R^3$ are independently selected from halogen, methoxy, $—OCHF_2$, $—OCF_3$, and methyl.

In one embodiment, $R^2$ and $R^3$ are halogen. In some embodiments, $R^2$ and $R^3$ are chloro.

In one embodiment, one of $R^2$ and $R^3$ is a halogen and the other is hydrogen. In one embodiment, one of $R^2$ and $R^3$ is a chloro and the other is hydrogen. In some embodiments, one of $R^2$ and $R^3$ is a fluoro and the other is hydrogen.

In one embodiment, Y is N. In some embodiments, Y is CH.

In one embodiment, A is pyridylene optionally substituted with one or two halogen. In some embodiments, A is pyridylene optionally substituted with one or two $C_{1-4}$-alkoxy.

In one embodiment, A is pyridylene substituted with one fluoro. In some embodiments, A is pyridylene substituted with one methoxy. In one embodiment, A is unsubstituted pyridylene.

In one embodiment, A is phenylene optionally substituted with one or two halogen. In one embodiment, A is phenylene optionally substituted with one or two $C_{1-4}$-alkoxy.

In one embodiment, A is phenylene substituted with one fluoro. In one embodiment, A is phenylene substituted with one methoxy. In one embodiment, A is unsubstituted phenylene.

In one embodiment, $R^4$ is $—CO_2R^5$, and $R^5$ is hydrogen. In one embodiment, $R^4$ is $—CO_2R^5$ and $R^5$ is $C_{1-6}$-alkyl or halo-$C_{1-6}$-alkyl.

In one embodiment, $R^4$ is $—C(O)NR^5R^6$, $R^5$ is $C_{1-6}$-alkyl or halo-$C_{1-6}$-alkyl, and $R^6$ is $C_{1-2}$-alkyl, wherein said $C_{1-2}$-alkyl is substituted with $—SO_3H$ or $—CO_2H$.

In one embodiment, $R^4$ is $—C(O)NR^5R^6$, $R^5$ is hydrogen, and $R^6$ is $C_{1-2}$-alkyl, wherein said $C_{1-2}$-alkyl is substituted with $—SO_3H$ or $—CO_2H$.

In one embodiment, $R^4$-A is:

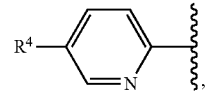

wherein the pyridylene is optionally substituted with one or two groups independently selected from halogen, $C_{1-4}$-alkoxy, halo-$C_{1-4}$-alkoxy, $C_{1-4}$-alkyl, and halo-$C_{1-4}$-alkyl.

In one embodiment, $R^4$-A is:

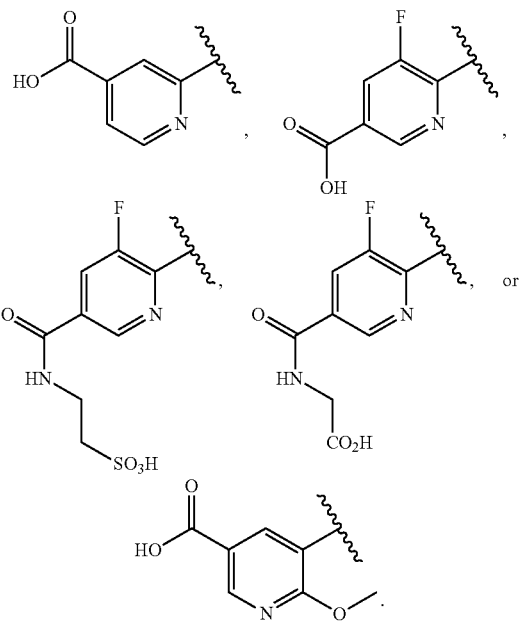

In one embodiment, $R^4$-A is:

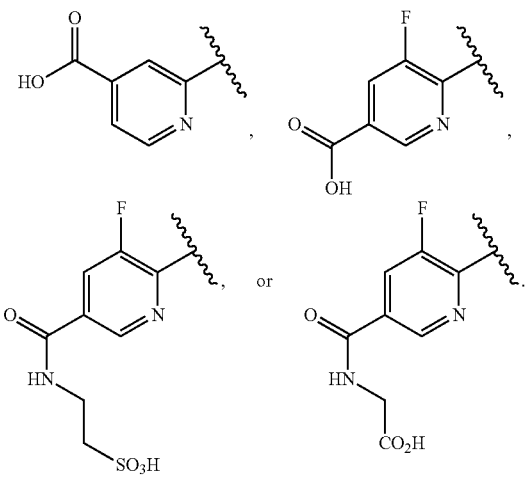

In one embodiment, R⁴-A is:
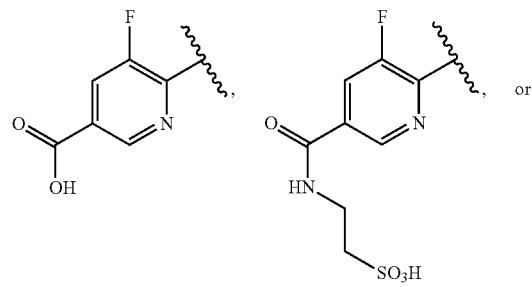
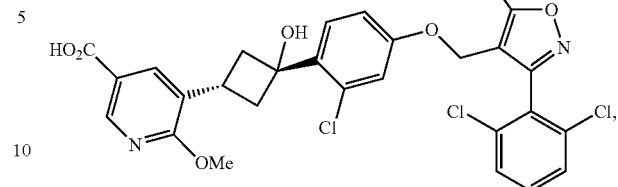
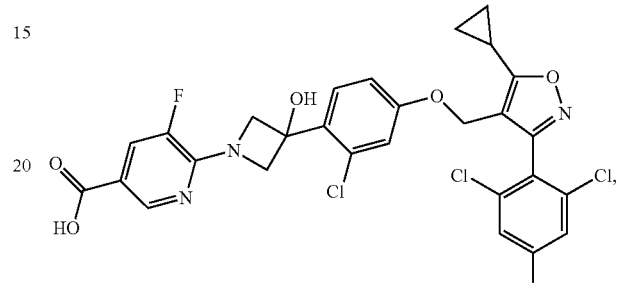
In one embodiment, R⁴-A is
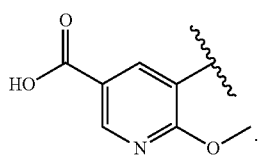 [SMILES: *c1cc(C(=O)O)cnc1OC]
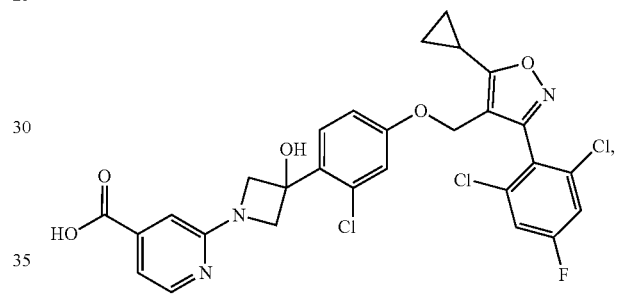
In one embodiment, provided is a compound selected from the group consisting of:
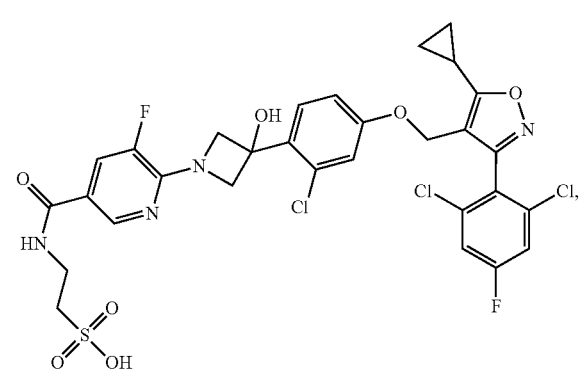
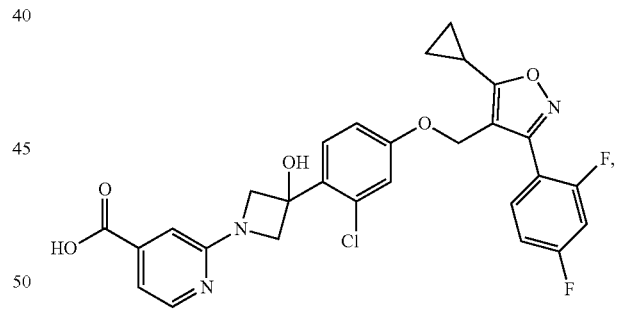
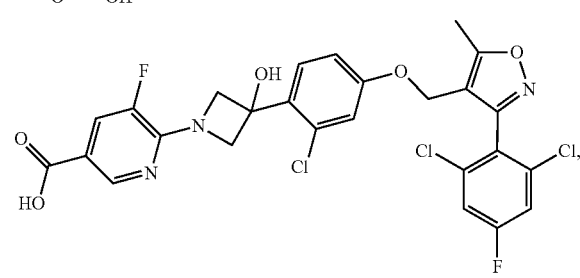
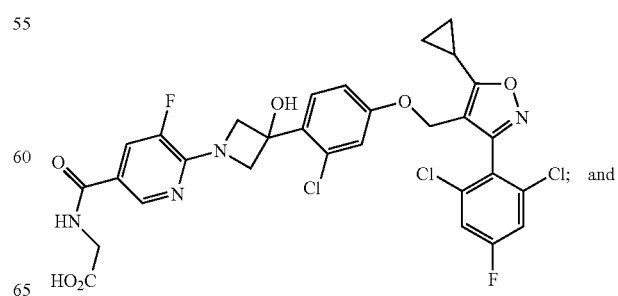

-continued

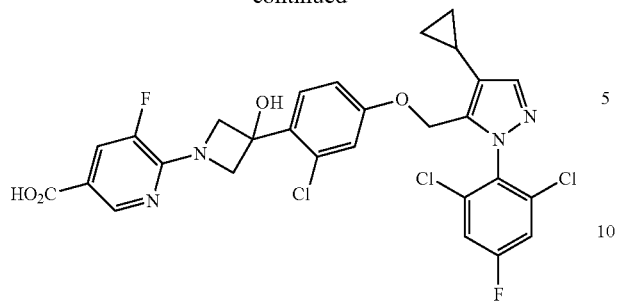

or a pharmaceutically acceptable salt, a stereoisomer, a mixture of stereoisomers, or a tautomer thereof.

In one embodiment, provided herein is a compound having the following formula:

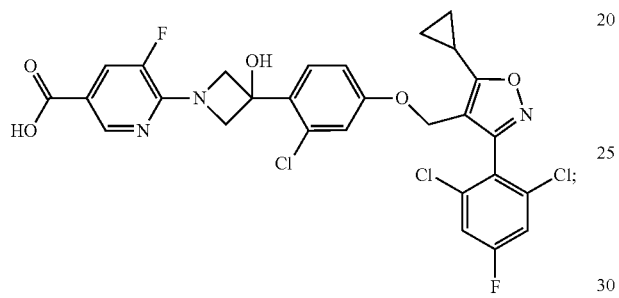

or a pharmaceutically acceptable salt thereof.

In one embodiment, provided herein is a compound having the following formula:

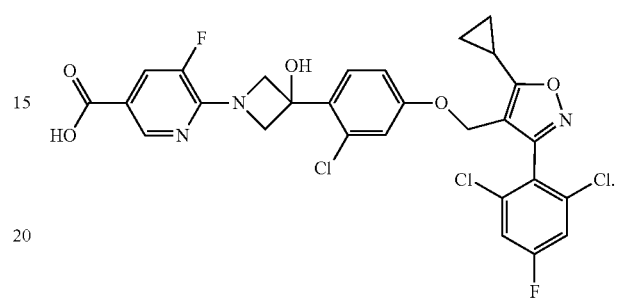

The chemical name of each of these compounds is provided in Table 1 below.

TABLE 1

| Example | Structure | IUPAC Name |
|---|---|---|
| 1 | 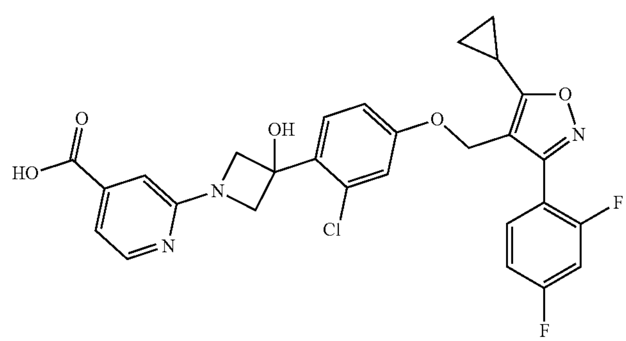 [SMILES: O=C(O)c1ccnc(N2CC(O)(c3ccc(OCc4c(-c5ccc(F)cc5F)noc4C4CC4)cc3Cl)C2)c1] | 2-(3-(2-chloro-4-((5-cyclopropyl-3-(2,4-difluorophenyl)isoxazol-4-yl)methoxy)phenyl)-3-hydroxyazetidin-1-yl)isonicotinic acid |
| 2 | 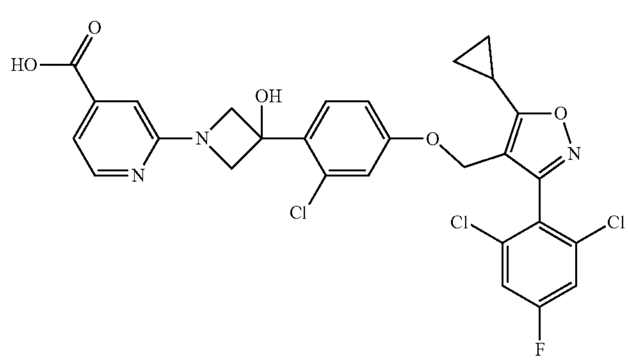 [SMILES: O=C(O)c1ccnc(N2CC(O)(c3ccc(OCc4c(-c5c(Cl)cc(F)cc5Cl)noc4C4CC4)cc3Cl)C2)c1] | 2-(3-(2-chloro-4-((5-cyclopropyl-3-(2,6-dichloro-4-fluorophenyl)isoxazol-4-yl)methoxy)phenyl)-3-hydroxyazetidin-1-yl)isonicotinic acid |

TABLE 1-continued

| Example | Structure | IUPAC Name |
|---|---|---|
| 3 | 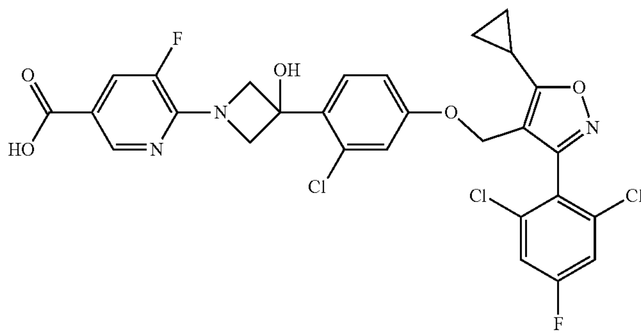 [SMILES: O=C(O)c1cnc(N2CC(O)(c3ccc(OCc4c(-c5c(Cl)cc(F)cc5Cl)noc4C4CC4)cc3Cl)C2)c(F)c1] | 6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinic acid |
| 4 | 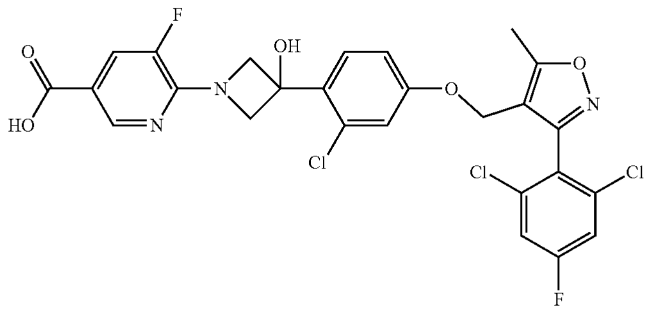 [SMILES: Cc1onc(-c2c(Cl)cc(F)cc2Cl)c1COc1ccc(C2(O)CN(c3ncc(C(=O)O)cc3F)C2)c(Cl)c1] | 6-(3-(2-chloro-4-((3-(2,6-dichloro-4-fluorophenyl)-5-methylisoxazol-4-yl)methoxy)phenyl)-3-hydroxyazetidin-1-yl)-5-fluoronicotinic acid |
| 5 | 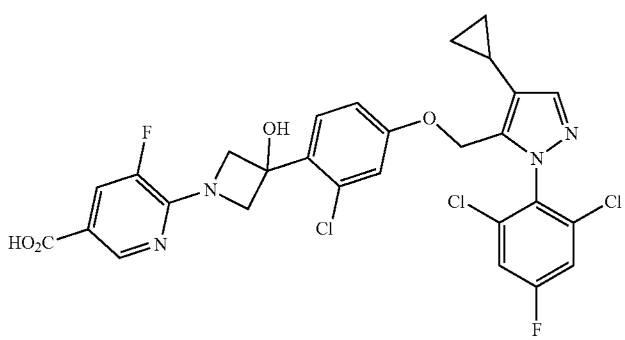 [SMILES: O=C(O)c1cnc(N2CC(O)(c3ccc(OCc4c(C5CC5)cnn4-c4c(Cl)cc(F)cc4Cl)cc3Cl)C2)c(F)c1] | 6-(3-(2-chloro-4-((4-cyclopropyl-1-(2,6-dichloro-4-fluorophenyl)-1H-pyrazol-5-yl)methoxy)phenyl)-3-hydroxyazetidin-1-yl)-5-fluoronicotinic acid |
| 6 | 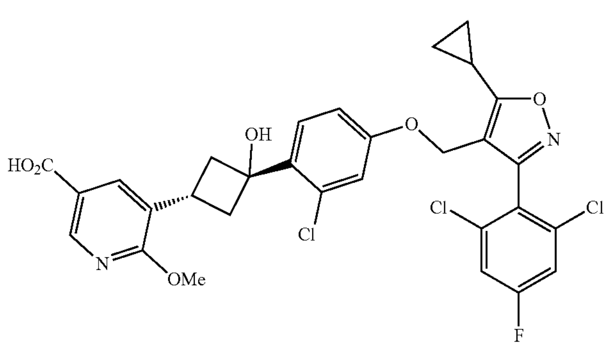 [SMILES: COc1ncc(C(=O)O)cc1[C@H]1C[C@](O)(c2ccc(OCc3c(-c4c(Cl)cc(F)cc4Cl)noc3C3CC3)cc2Cl)C1] | 5-((1S,3S)-3-(2-chloro-4-((5-cyclopropyl-3-(2,6-dichloro-4-fluorophenyl)isoxazol-4-yl)methoxy)phenyl)-3-hydroxycyclobutyl)-6-methoxynicotinic acid |

TABLE 1-continued

| Example | Structure | IUPAC Name |
|---|---|---|
| 7 | 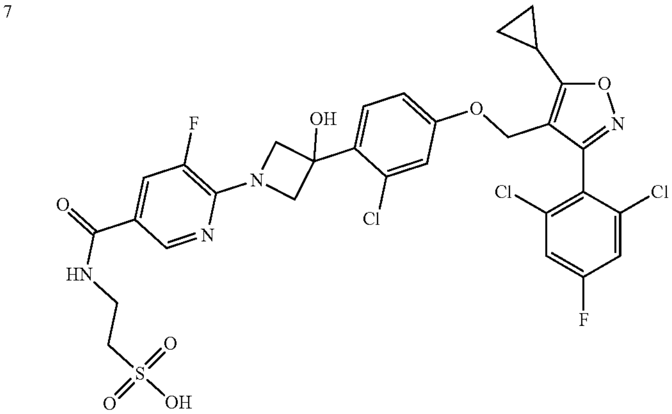 | 2-(6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinamido)ethane-1-sulfonic acid |
| 8 | 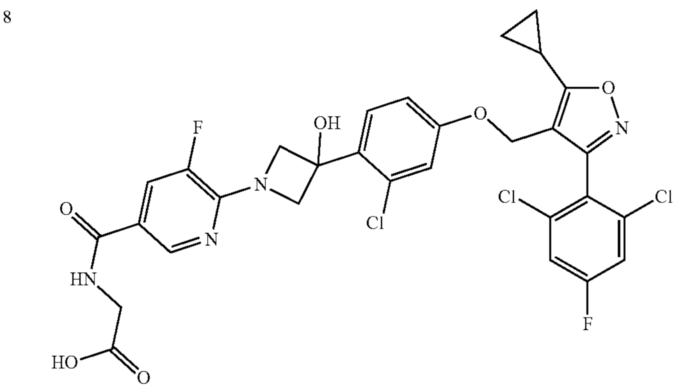 | (6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinoyl)glycine |

Pharmaceutical Compositions and Modes of Administration

The present disclosure further provides pharmaceutical compositions comprising at least one compound of the present disclosure, or a prodrug, a pharmaceutically acceptable salt, or solvate thereof as active ingredient together with a pharmaceutically acceptable carrier.

The pharmaceutical composition of the present disclosure may additionally comprise one or more other compounds as active ingredients like a prodrug or other nuclear receptor modulators.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of the present disclosure can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Since the compounds of the present disclosure mostly represent carboxylic acids or similar anionic isosters thereof, and since salt forms of ionic compounds can substantially affect bioavailability, the compounds of the present disclosure may also be used as salts with various countercations to yield an orally available formulation. Such pharmaceutically acceptable cations may be amongst others mono- or bivalent ions such as ammonium, the alkaline metals sodium or potassium or the alkaline earth metals magnesium or calcium, certain pharmaceutically acceptable amines such as tris(hydroxymethyl)aminomethane, ethylendiamine, diethylamine, piperazine or others, or certain cationic amino acids such as lysine or arginine.

The compounds of the present disclosure may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present disclosure. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In some embodiments, compounds of the present disclosure are administered orally.

Kits

Provided herein are also kits that include a compound of the disclosure, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of Cot activity. The therapeutically effective amount may vary depending on the subject, and disease or condition being treated, the weight and age of the subject, the severity of the disease or condition, and the manner of administering, which can readily be determined by one or ordinary skill in the art.

The disclosure further relates to the use of said compounds for the treatment and/or prophylaxis of diseases and/or conditions through binding of said nuclear receptor by said compounds. Further the present disclosure relates to the use of said compounds for the preparation of a medicament for the treatment and/or prophylaxis of diseases and/or conditions through binding of said nuclear receptor by said compounds.

Also provided herein are methods of treating a patient having a FXR mediated condition comprising administering a compound of formula (I), or pharmaceutically acceptable salt thereof, or a pharmaceutical composition comprising a compound of formula (I), or pharmaceutically acceptable salt thereof.

In some embodiments, a compound of formula (I), or pharmaceutically acceptable salt thereof, or a pharmaceutical composition comprising a compound of formula (I), or pharmaceutically acceptable salt thereof is provided for use in the treatment of a FXR mediated condition.

In some embodiments, a compound of formula (I), or pharmaceutically acceptable salt thereof, or a pharmaceutical composition comprising a compound of formula (I), or pharmaceutically acceptable salt thereof, is provided for the manufacture of a medicament for the treatment of a FXR mediated condition.

In some embodiments, the FXR mediated condition is:
a chronic intrahepatic or some form of extrahepatic cholestatic condition;
liver fibrosis;
an obstructive inflammatory disorder of the liver;
chronic inflammatory disorder of the liver;
liver cirrhosis;
liver steatosis or an associated syndrome;
cholestatic or fibrotic effects that are associated with alcohol-induced cirrhosis or with viral-borne forms of hepatitis;
liver failure or liver ischemia after major liver resection;
chemotherapy associated steatohepatitis (CASH);
acute liver failure; or
Inflammatory Bowel Disease.

In some embodiments, the FXR mediated condition is:
a lipid and lipoprotein disorder;
Type I Diabetes;
Type II Diabetes;
  clinical complications of Type I and Type II Diabetes selected from the group consisting of diabetic nephropathy, diabetic neuropathy, diabetic retinopathy and other observed effects of clinically manifest long term Diabetes;
Non-Alcoholic Fatty Liver Disease (NAFLD);
Non-Alcoholic Steatohepatitis (NASH);
obesity;
a metabolic syndrome selected from the group consisting of combined conditions of dyslipidemia, diabetes and abnormally high body-mass index;
acute myocardial infarction;
acute stroke; or
thrombosis which occurs as an endpoint of chronic obstructive atherosclerosis.

In some embodiments, the FXR mediated condition is:
a non-malignant hyperproliferative disorder; and
a malignant hyperproliferative disorder selected from the group consisting of hepatocellular carcinoma, colon adenoma, and polyposis;
colon adenocarcinoma;
breast cancer;
pancreas adenocarcinoma;
Barrett's esophagus; or
other forms of neoplastic diseases of the gastrointestinal tract and the liver.

In some embodiments, the FXR mediated condition is Non-Alcoholic Steatohepatitis (NASH).

In some embodiments, the present disclosure relates to the use of compounds according to Formula (I) in the preparation of a medicament for the prophylaxis and/or treatment of chronic intrahepatic or some forms of extrahepatic cholestatic conditions, of liver fibrosis, of acute intraheptic cholestatic conditions, of obstructive or chronic inflammatory disorders that arise out of improper bile composition, of gastrointestinal conditions with a reduced uptake of dietary fat and fat-soluble dietary vitamins, of inflammatory bowel diseases, of lipid and lipoprotein disorders, of Type II Diabetes and clinical complications of Type I and Type II Diabetes, of conditions and diseases which result from chronic fatty and fibrotic degeneration of organs due to enforced lipid and specifically triglyceride accumulation and subsequent activation of profibrotic pathways, of obesity and metabolic syndrome (combined conditions of dyslipidemia, diabetes and abnormally high body-mass index), of acute myocardial infarction, of acute stroke, of thrombosis which occurs as an endpoint of chronic obstructive atherosclerosis, of persistant infections by intracellular bacteria or parasitic protozoae, of non-malignant hyperproliferative disorders, of malignant hyperproliferative disorders, of colon adenocarcinoma and hepatocellular carcinoma in particular, of liver steatosis and associated syndromes, of liver failure or liver malfunction as an outcome of chronic liver diseases or of surgical liver resection, of Hepatitis B infection, of Hepatitis C infection and/or of cholestatic and fibrotic effects that are associated with alcohol-induced cirrhosis or with viral-borne forms of hepatitis.

Medicaments as referred to herein may be prepared by conventional processes, including the combination of a compound according to the present disclosure and a pharmaceutically acceptable carrier.

FXR is proposed to be a nuclear bile acid sensor. As a result, it modulates both, the synthetic output of bile acids in the liver and their recycling in the intestine (by regulating bile acid binding proteins). But beyond bile acid physiology, FXR seems to be involved in the regulation of many diverse physiological processes which are relevant in the etiology and for the treatment of diseases as diverse as cholesterol gallstones, metabolic disorders such as Type II Diabetes, dyslipidemias or obesity, chronic inflammatory diseases such as Inflammatory Bowel Diseases or chronic intrahepatic forms of cholestasis and many other diseases.

FXR regulates a complex pattern of response genes in the liver and in the gastrointestinal tract. The gene products have impact on diverse physiological processes. In the course of functional analysis of FXR, the first regulatory network that was analyzed was the regulation of bile acid synthesis. While the LXRs induce the key enzyme of the conversion of cholesterol into bile acids, Cyp7A1, via the induction of the regulatory nuclear receptor LRH-1, FXR represses the induction of Cyp7A1 via the upregulation of mRNA encoding SHP, a further nuclear receptor that is dominant repressive over LRH-1. Since FXR binds the end products of this pathway, primary bile acids such as cholic acid (CA) or CDCA, this can be regarded as an example of feedback inhibition on the gene expression level. Parallel to the repression of bile acid synthesis via SHP, FXR induces a range of so-called ABC (for ATP-binding cassette) transporters that are responsible for the export of toxic bile acids from the hepatocyte cytosol into the canaliculi, the small bile duct ramifications where the bile originates. This hepatoprotective function of FXR became first apparent with the analysis of FXR knockout mice. where under- or overexpression of several ABC-transporters in the liver was shown. Further detailed analysis revealed that the major bile salt excretory pump BSEP or ABCB11 (as well as the key enzyme which mediates lipid transfer from lipoproteins to phospholipids, PLTP, and the two key canalicular membrane transporters for phospholipids, MRP-2 (ABCC4) and MDR-3 (ABCB4), are direct targets for ligand-directed transcriptional activation by FXR.

The fact that FXR seems to be the major metabolite sensor and regulator for the synthesis, export and re-circulation of bile acids suggested the use of FXR ligands to induce bile flow and change bile acid composition towards more hydrophilic composition. With the development of the first synthetic FXR ligand GW4064 as a tool compound and of the semi-synthetic artificial bile acid ligand 6-alpha-ethyl-CDCA, the effects of superstimulation of FXR by potent agonists could be analyzed. It was shown that both ligands induce bile flow in bile duct ligated animals. Moreover, in addition to choleretic effects, also hepatoprotective effects could be demonstrated. This hepatoprotective effect was further narrowed down to an anti-fibrotic effect that results from the repression of Tissue Inhibitors of Matrix-Metalloproteinases, TIMP-1 and 2, the induction of collagen-deposit resolving Matrix-Metalloproteinase 2 in hepatic stellate cells and the subsequent reduction of alpha-collagen mRNA and Transforming growth factor beta (TGF-beta) mRNA which are both pro-fibrotic factors by FXR agonists. Furthermore, anti-cholestatic activity was demonstrated in bile-duct ligated animal models as well as in animal models of estrogen-induced cholestasis.

Genetic studies demonstrate that in hereditary forms of cholestasis (Progressive Familiar Intrahepatic Cholestasis=PFIC, Type I-IV) either nuclear localization of FXR itself is reduced as a consequence of a mutation in the FIC1 gene (in PFIC Type I, also called Byler's Disease) (F. Chen et al., Gastroenterology 2004, 126, 756; L. Alvarez et al., Hum. Mol. Genet. 2004, 13, 2451) or levels of the FXR target gene encoding MDR-3 phospholipid export pump are reduced (in PFIC Type III). Taken together there is a growing body of evidence that FXR binding compounds will demonstrate substantial clinical utility in the therapeutic regimen of chronic cholestatic conditions such as Primary Biliary Cirrhosis (PBC) or Primary Sclerosing Cholangitis (PSC).

The deep impact that FXR activation has on bile acid metabolism and excretion is not only relevant for cholestatic syndromes but even more directly for a therapy against gallstone formation. Cholesterol gallstones form due to low solubility of cholesterol that is actively pumped out of the liver cell into the lumen of the canaliculi. It is the relative percentage of content of the three major components, bile acids, phospholipids and free cholesterol that determines the formation of mixed micelles and hence apparent solubility of free cholesterol in the bile. FXR polymorphisms map as quantitative trait loci as one factor contributing to gallstone disease. Using the synthetic FXR tool compound GW4064 it could be demonstrated that activation of FXR leads to an improvement of the Cholesterol Saturation Index (CSI) and directly to an abolishment of gallstone formation in C57L gallstone susceptible mice whereas drug treatment in FXR knockout mice shows no effect on gallstone formation.

These results qualify FXR as a good target for the development of small molecule agonists that can be used to prevent cholesterol gallstone formation or to prevent re-formation of gallstones after surgical removal or shockwave lithotripsy.

Thus, in one embodiment of the disclosure, the compound according to Formula (I) and pharmaceutical compositions comprising said compound is used for the prophylaxis and/or treatment of obstructive or chronic inflammatory disorders that arise out of improper bile composition such as cholelithiasis also known as cholesterol gallstones.

Beyond its strong hepatoprotective and choleretic as well as anti-fibrotic effects that FXR shows upon small molecule stimulated activation in the liver, FXR seems to have a role in protecting the intestine from neoplastic transformation and from the development of polyps and their transition into adenocarcinoma in the gut. Similar to the situation in the intestine absence of FXR leads to a high increase in the formation of Hepatocellular Cacrcinoma (HCC), the most prominent form of liver cancer. Whereas a functional FXR prevents the formation of colon adenocarcinoma and hepatocellular carcinoma, FXR activation induces liver regeneration after hepatectomy.

The combined hepatoprotective, anti-neoplastic and liver regenerative effects associated with FXR activation can be therapeutically exploited for the use of FXR agonists in the treatment of severe liver diseases. In one embodiment, the compounds according to the disclosure and pharmaceutical compositions comprising said compounds are used in the treatment of liver diseases such as HCC, stimulation of liver regrowth and amelioration of side effects associated with major liver resection, liver cirrhosis independent of the etiology and prevention or treatment of liver ischemia in the course of liver transplantation or major liver surgery.

Since the discovery of the first synthetic FXR agonist and its administration to rodents it became evident that FXR is a key regulator of serum triglycerides. Over the past six years accumulating evidence has been published that activation of FXR by synthetic agonists leads to significant reduction of serum triglycerides, mainly in the form of reduced VLDL, but also to reduced total serum cholesterol.

But the lowering of serum triglycerides is not a stand alone effect. Treatment of db/db or ob/ob mice with synthetic FXR agonist GW4064 resulted in marked and combined reduction of serum triglycerides, total cholesterol, free fatty acids, ketone bodies such as 3-OH Butyrate. Moreover, FXR activation engages with the intracellular insulin signaling pathway in hepatocytes, resulting in reduced output of glucose from liver gluconeogenesis but concomitant increase in liver glycogen. Insulin sensitivity as well as glucose tolerance were positively impacted by FXR treatment. An effect on reduction of body weight was also recently observed in mice overfed with a high lipid diet. This weight loss effect might results from FXR's induction of FGF-19, a fibroblast growth factor that is known to lead to weight loss and athletic phenotype. The effect of FXR agonist on reduction of body weight has been demonstrated.

Taken together, these pharmacological effects of FXR agonists can be exploited in different therapeutic ways: FXR binding compounds are thought to be good candidates for the treatment of Type II Diabetes because of their insulin sensitization, glycogenogenic, and lipid lowering effects.

In one embodiment, the compounds according to the disclosure and pharmaceutical compositions comprising said compounds are used in the prophylaxis and/or treatment of Type II Diabetes which can be overcome by FXR-mediated upregulation of systemic insulin sensitivity and intracellular insulin signalling in liver, increased peripheral glucose uptake and metabolisation, increased glycogen storage in liver, decreased output of glucose into serum from liver-borne gluconeogenesis.

In a further embodiment, said compounds and pharmaceutical compositions are used for the prophylaxis and/or treatment of chronic intrahepatic, such as PBC, PSC, progressive familiar cholestasis (PFIC), alcohol-induced cirrhosis and associated cholestasis, and some forms of extrahepatic cholestatic conditions, or liver fibrosis.

The disclosure also relates to a compound of Formula (I) or a pharmaceutical composition comprising said compound for the prophylaxis and/or treatment of gastrointestinal conditions with a reduced uptake of dietary fat and fat-soluble dietary vitamins which can be overcome by increased intestinal levels of bile acids and phospholipids.

In a further embodiment, said compound or pharmaceutical composition is used for preventing and/or treating a disease selected from the group consisting of lipid and lipoprotein disorders such as hypercholesterolemia, hypertriglyceridemia, and atherosclerosis as a clinically manifest condition which can be ameliorated by FXR's beneficial effect on lowering total plasma cholesterol, lowering serum triglycerides, increasing conversion of liver cholesterol into bile acids and increased clearance and metabolic conversion of VLDL and other lipoproteins in the liver.

In one further embodiment, said compound and pharmaceutical composition are used for the prophylaxis and/or treatment of diseases where the combined lipid lowering, anti-cholestatic and anti-fibrotic effects of FXR-targeted medicaments can be exploited for the treatment of liver steatosis and associated syndromes such as Non-Alcoholic Steatohepatitis (NASH), or for the treatment of cholestatic and fibrotic effects that are associated with alcohol-induced cirrhosis, or with viral-borne forms of hepatitis.

In conjunction with the hypolipidemic effects it was also shown that loss of functional FXR leads to increased atherosclerosis in ApoE knockout mice. Therefore, FXR agonists might have clinical utility as anti-atherosclerotic and cardioprotective drugs. The downregulation of Endothelin-1 in Vascular Smooth Muscle Cells might also contribute to such beneficial therapeutic effects.

The disclosure also relates to a compound according to Formula (I) or a pharmaceutical composition comprising said compound for preventive and posttraumatic treatment of a cardiovascular disorder, such as acute myocardial infarction, acute stroke, or thrombosis which occur as an endpoint of chronic obstructive atherosclerosis.

Beyond controlling intestinal and colonic polyp formation, FXR seems to be expressed in breast cancer tissue and cell lines but not in healthy breast tissue and seems to interact with the Estrogen Receptor in ER positive breast cancer cells.

This would allow to regard FXR also as a potential target for the treatment of proliferative diseases, especially metastasizing cancer forms that express a small molecule responsive form of FXR.

In a further embodiment, said compounds and pharmaceutical compositions are used for the prophylaxis and/or treatment of malignant hyperproliferative disorders such as different forms of cancer, specifically certain forms of breast, liver or colon cancer where interference with an FXR ligand will have a beneficial impact.

Finally, FXR seems also to be involved in the control of antibacterial defense in the intestine although an exact mechanism is not provided. From these published data, however, one can conclude that treatment with FXR agonists might have a beneficial impact in the therapy of Inflammatory Bowel Disorders (IBD), in particular those forms where the upper (ileal) part of the intestine is affected (e.g. ileal Crohn's disease) because this seems to be the site of action of FXR's control on bacterial growth. In IBD, the desensitization of the adaptive immune response is somehow impaired in the intestinal immune system. Bacterial overgrowth might then be the causative trigger towards establishment of a chronic inflammatory response. Hence, dampening of bacterial growth by FXR-borne mechanisms might be a key mechanism to prevent acute inflammatory episodes.

Thus, the disclosure also relates to a compound according to Formula (I) or a pharmaceutical composition comprising said compound for preventing and/or treating a disease related to an Inflammatory Bowel Disease, such as Crohn's disease or Colitis ulcerosa. FXR-mediated restoration of intestinal barrier function and reduction in non-commensal bacterial load is believed to be helpful in reducing the exposure of bacterial antigens to the intestinal immune system and can therefore reduce inflammatory responses.

The disclosure further relates to a compound or pharmaceutical composition for the prophylaxis and/or treatment of obesity and associated disorders such as metabolic syndrome (combined conditions of dyslipidemias, diabetes and abnormally high body-mass index) which can be overcome by FXR-mediated lowering of serum triglycerides, blood glucose and increased insulin sensitivity and FXR-mediated weight loss.

In a further embodiment, the compounds or pharmaceutical composition of the present disclosure are useful in preventing and/or treating clinical complications of Type I and Type II Diabetes. Examples of such complications include Diabetic Nephropathy, Diabetic Retinopathy, Diabetic Neuropathies, or Peripheral Arterial Occlusive Disease (PAOD). Other clinical complications of Diabetes are also encompassed by the present disclosure.

Furthermore, conditions and diseases which result from chronic fatty and fibrotic degeneration of organs due to enforced lipid and specifically triglyceride accumulation and subsequent activation of profibrotic pathways may also be prevented and/or treated by administering the compounds or pharmaceutical composition of the present disclosure. Such conditions and diseases encompass NASH and chronic cholestatic conditions in the liver, Glomerulosclerosis and Diabetic Nephropathy in the kidney, Macula Degeneration and Diabetic Retinopathy in the eye and neurodegenerative diseases, such as Alzheimer's Disease in the brain, or Diabetic Neuropathies in the peripheral nervous system.

Dosage

The effective dosage of active ingredient employed may vary depending on the particular compound employed, the mode of administration, the condition being treated and the severity of the condition being treated. Such dosage may be ascertained readily by a person skilled in the art.

When treating or preventing FXR mediated conditions for which compounds of the present disclosure are indicated, generally satisfactory results are obtained when the compounds of the present disclosure are administered at a daily dosage of from about 0.1 milligram to about 100 milligram per kilogram of animal body weight. In some embodiments, the compounds of the present disclosure are given as a single daily dose or in divided doses two to six times a day, or in sustained release form. For most large mammals, the total daily dosage is from about 1 milligram to about 1000 milligrams, or from about 1 milligram to about 50 milligrams. In the case of a 70 kg adult human, the total daily dose will generally be from about 7 milligrams to about 350 milligrams. This dosage regimen may be adjusted to provide the optimal therapeutic response. In some embodiments, the total daily dosage is from about 1 milligram to about 900 milligrams, about 10 milligrams to about 800 milligrams, about 20 milligrams to about 700 milligrams, about 30 milligrams to about 600 milligrams, about 40 milligrams to about 550 milligrams, or about 50 milligrams to about 400 milligrams.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the methods provided herein comprise administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Combination Therapies

In some embodiments, a compound disclosed herein is administered in combination with one or more additional therapeutic agents to treat or prevent a disease or condition disclosed herein. In some embodiments, the one or more additional therapeutic agents are a(n) ACE inhibitor, Acetyl CoA carboxylase inhibitor, Adenosine A3 receptor agonist, Adiponectin receptor agonist, AKT protein kinase inhibitor, AMP-activated protein kinases (AMPK), Amylin receptor agonist, Angiotensin II AT-1 receptor antagonist, Autotaxin inhibitors, Bioactive lipid, Calcitonin agonist, Caspase inhibitor, Caspase-3 stimulator, Cathepsin inhibitor, Caveolin 1 inhibitor, CCR2 chemokine antagonist, CCR3 chemokine antagonist, CCR5 chemokine antagonist, Chloride channel stimulator, CNR1 inhibitor, Cyclin D1 inhibitor, Cytochrome P450 7A1 inhibitor, DGAT1/2 inhibitor, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF1 receptor agonist, Fibroblast growth factor (FGF-15, FGF-19, FGF-21) ligands, Galectin-3 inhibitor, Glucagon receptor agonist, Glucagon-like peptide 1 agonist, G-protein coupled bile acid receptor 1 agonist, Hedgehog (Hh) modulator, Hepatitis C virus NS3 protease inhibitor, Hepatocyte nuclear factor 4 alpha modulator (HNF4A), Hepatocyte growth factor modulator, HMG CoA reductase inhibitor, IL-10 agonist, IL-17 antagonist, Ileal sodium bile acid cotransporter inhibitor, Insulin sensitizer, integrin modulator, intereukin-1 receptor-associated kinase 4 (IRAK4) inhibitor, Jak2 tyrosine kinase inhibitor, Klotho beta stimulator, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, Matrix metalloproteinases (MMPs) inhibitor, MEKK-5 protein kinase inhibitor, Membrane copper amine oxidase (VAP-1) inhibitor, Methionine aminopeptidase-2 inhibitor, Methyl CpG binding protein 2 modulator, MicroRNA-21 (miR-21) inhibitor, Mitochondrial uncoupler, Myelin basic protein stimulator, NACHT LRR PYD domain protein 3 (NLRP3) inhibitor, NAD-dependent deacetylase sirtuin stimulator, NADPH oxidase inhibitor (NOX), Nicotinic acid receptor 1 agonist, P2Y13 purinoceptor stimulator, PDE 3 inhibitor, PDE 4 inhibitor, PDE 5 inhibitor, PDGF receptor beta modulator, Phospholipase C inhibitor, PPAR alpha agonist, PPAR delta agonist, PPAR gamma agonist, PPAR gamma modulator, Protease-activated receptor-2 antagonist, Protein kinase modulator, Rho associated protein kinase inhibitor, Sodium glucose transporter-2 inhibitor, SREBP transcription factor inhibitor, STAT-1 inhibitor, Stearoyl CoA desaturase-1 inhibitor, Suppressor of cytokine signalling-1 stimulator, Suppressor of cytokine signalling-3 stimulator, Transforming growth factor β (TGF-β), Transforming growth factor β activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, WNT modulators, or YAP/TAZ modulator.

Non-limiting examples of the one or more additional therapeutic agents include:

ACE inhibitors, such as enalapril;
Acetyl CoA carboxylase (ACC) inhibitors, such as DRM-01, gemcabene, PF-05175157, and QLT-091382;
Adenosine receptor agonists, such as CF-102, CF-101, CF-502, and CGS21680;
Adiponectin receptor agonists, such as ADP-355;
Amylin/calcitonin receptor agonists, such as KBP-042;
AMP activated protein kinase stimulators, such as 0-304;
Angiotensin II AT-1 receptor antagonists, such as irbesartan;
Autotaxin inhibitors, such as PAT-505, PAT-048, GLPG-1690, X-165, PF-8380, and AM-063;
Bioactive lipids, such as DS-102;
Cannabinoid receptor type 1 (CNR1) inhibitors, such as namacizumab and GWP-42004;
Caspase inhibitors, such as emricasan;
Pan cathepsin B inhibitors, such as VBY-376;
Pan cathepsin inhibitors, such as VBY-825;
CCR2/CCR5 chemokine antagonists, such as cenicriviroc;
CCR2 chemokine antagonists, such as propagermanium;
CCR3 chemokine antagonists, such as bertilimumab;
Chloride channel stimulators, such as cobiprostone;
Diglyceride acyltransferase 2 (DGAT2) inhibitors, such as IONIS-DGAT2Rx;
Dipeptidyl peptidase IV inhibitors, such as linagliptin;
Eotaxin ligand inhibitors, such as bertilimumab;
Extracellular matrix protein modulators, such as CNX-024;
Farnesoid X receptor (FXR) agonists, such as AGN-242266, AKN-083, EDP-305, GNF-5120, LJN-452, LMB-763, obeticholic acid, Px-102, Px-103, M790, M780, M450, M480, PX20606, EYP-001, and INT-2228;
Farnesoid X receptor (FXR)/G-protein coupled bile acid receptor 1(TGR5) agonists, such as INT-767;
Fatty acid synthase inhibitors, such as TVB-2640;
Fibroblast growth factor 19 (rhFGF19)/cytochrome P450 (CYP)7A1 inhibitors, such as NGM-282;
Fibroblast growth factor 21(FGF-21) ligand, such as BMS-986171, BMS-986036;
Fibroblast growth factor 21(FGF-21)/glucagon like peptide 1 (GLP-1) agonists, such as YH-25723;
Galectin-3 inhibitors, such as GR-MD-02;
Glucagon-like peptide 1(GLP1R) agonists, such as AC-3174, liraglutide, semaglutide;
G-protein coupled bile acid receptor 1(TGR5) agonists, such as RDX-009, INT-777;
Heat shock protein 47 (HSP47) inhibitors, such as ND-L02-s0201;
HMG CoA reductase inhibitors, such as atorvastatin, fluvastatin, pitavastatin, pravastatin, rosuvastatin, and simvastatin;
IL-10 agonists, such as peg-ilodecakin;
Ileal sodium bile acid cotransporter inhibitors, such as A-4250, volixibat potassium ethanolate hydrate (SHP-262), and GSK2330672;
Insulin sensitizers, such as, KBP-042, MSDC-0602K, Px-102, RG-125 (AZD4076), and VVP-100X;
beta Klotho (KLB)-FGF1c agonist, such as NGM-313;
5-Lipoxygenase inhibitors, such as tipelukast (MN-001);
Lipoprotein lipase inhibitors, such as CAT-2003;
LPL gene stimulators, such as alipogene tiparvovec;

Liver X receptor (LXR) modulators, such as PX-L603, PX-L493, BMS-852927, T-0901317, GW-3965, and SR-9238;

Lysophosphatidate-1 receptor antagonists, such as BMT-053011, UD-009. AR-479, ITMN-10534, BMS-986020, and KI-16198;

Lysyl oxidase homolog 2 inhibitors, such as simtuzumab;

Semicarbazide-Sensitive Amine Oxidase/Vascular Adhesion Protein-1 (SSAONAP-1) Inhibitors, such as PXS-4728A;

Methionine aminopeptidase-2 inhibitors, such as ZGN-839;

Methyl CpG binding protein 2 modulators, such as mercaptamine;

Mitochondrial uncouplers, such as 2,4-dinitrophenol;

Myelin basic protein stimulators, such as olesoxime;

NADPH oxidase 1/4 inhibitors, such as GKT-831;

Nicotinic acid receptor 1 agonists, such as ARI-3037MO;

NACHT LRR PYD domain protein 3 (NLRP3) inhibitors, such as KDDF-201406-03, and NBC-6;

Nuclear receptor modulators, such as DUR-928;

P2Y13 purinoceptor stimulators, such as CER-209;

PDE 3/4 inhibitors, such as tipelukast (MN-001);

PDE 5 inhibitors, such as sildenafil;

PDGF receptor beta modulators, such as BOT-191, BOT-509;

PPAR agonists, such as elafibranor (GFT-505), MBX-8025, deuterated pioglitazone R-enantiomer, pioglitazone, DRX-065, saroglitazar, and IVA-337;

Protease-activated receptor-2 antagonists, such as PZ-235;

Protein kinase modulators, such as CNX-014;

Rho associated protein kinase (ROCK) inhibitors, such as KD-025;

Sodium glucose transporter-2(SGLT2) inhibitors, such as ipragliflozin, remogliflozin etabonate, ertugliflozin, dapagliflozin, and sotagliflozin;

SREBP transcription factor inhibitors, such as CAT-2003 and MDV-4463;

Stearoyl CoA desaturase-1 inhibitors, such as aramchol;

Thyroid hormone receptor beta agonists, such as MGL-3196, MGL-3745, VK-2809;

TLR-4 antagonists, such as JKB-121;

Tyrosine kinase receptor modulators, such as CNX-025;

GPCR modulators, such as CNX-023; and

Nuclear hormone receptor modulators, such as Px-102.

In certain specific embodiments, the one or more additional therapeutic agents are selected from A-4250, AC-3174, acetylsalicylic acid, AK-20, alipogene tiparvovec, aramchol, ARI-3037M0, ASP-8232, bertilimumab, Betaine anhydrous, BI-1467335, BMS-986036, BMS-986171, BMT-053011, BOT-191, BTT-1023, CAT-2003, cenicriviroc, CER-209, CF-102, CGS21680, CNX-014, CNX-023, CNX-024, CNX-025, cobiprostone, colesevelam, dapagliflozin, deuterated pioglitazone R-enantiomer, 2,4-dinitrophenol, DRX-065, DS-102, DUR-928, EDP-305, elafibranor (GFT-505), emricasan, enalapril, ertugliflozin, evogliptin, F-351, GKT-831, GNF-5120, GR-MD-02, hydrochlorothiazide, icosapent ethyl ester, IMM-124-E, INT-767, IONIS-DGAT2Rx, ipragliflozin, Irbesarta, propagermanium, IVA-337, JKB-121, KB-GE-001, KBP-042, KD-025, M790, M780, M450, metformin, sildenafil, LC-280126, linagliptin, liraglutide, LJN-452, LMB-763, MBX-8025, MDV-4463, mercaptamine, MGL-3196, MGL-3745, MSDC-0602K, namacizumab, NC-101, ND-L02-s0201, NGM-282, NGM-313, NGM-386, NGM-395, norursodeoxycholic acid, 0-304, obeticholic acid, 25HC3S, olesoxime, PAT-505, PAT-048, peg-ilodecakin, pioglitazone, pirfenidone, PRI-724, PX20606, Px-102, PX-L603, PX-L493, PXS-4728A, PZ-235, RDX-009, remogliflozin etabonate, RG-125 (AZD4076), saroglitazar, semaglutide, simtuzumab, solithromycin, sotagliflozin, statins (atorvastatin, fluvastatin, pitavastatin, pravastatin, rosuvastatin, simvastatin), TCM-606F, TEV-45478, tipelukast (MN-001), TLY-012, TRX-318, TVB-2640, UD-009, ursodeoxycholic acid, VBY-376, VBY-825, VK-2809, vismodegib, volixibat potassium ethanolate hydrate (SHP-626), VVP-100X, WAV-301, WNT-974, and ZGN-839.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

The compounds of the present disclosure can be prepared according to the procedures of the following Schemes and Examples, using appropriate materials and are further exemplified by the following specific examples. Moreover, by utilizing the procedures described herein, in conjunction with ordinary skills in the art, additional compounds of the present disclosure claimed herein can be readily prepared. The compounds illustrated in the examples are not, however, to be construed as forming the only genus that is considered as the disclosure. The examples further illustrate details for the preparation of the compounds of the present disclosure. Those skilled in the art will readily understand that known variations of the conditions and processes of the following preparative procedures can be used to prepare these compounds. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. The instant compounds are generally isolated in the form of their pharmaceutically acceptable salts, such as those described above. In general, compounds described herein are typically stable and isolatable at room temperature and pressure The amine-free bases corresponding to the isolated salts can be generated by neutralization with a suitable base, such as aqueous sodium hydrogen carbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization. The carboxylic free acids corresponding to the isolated salts can be generated by neutralization with a suitable acid, such as aqueous hydrochloric acid, sodium hydrogen sulfate, sodium dihydrogen phosphate, and extraction of the liberated carboxylic-free acid into an organic solvent, followed by evaporation. The carboxylic acid, isolated in this manner, can be further converted into another pharmaceutically acceptable salt by dissolution in an organic solvent, followed by addition of the appropriate base and subsequent evaporation, precipitation or crystallization.

An illustration of the preparation of compounds of the present disclosure is shown below. Unless otherwise indicated in the schemes, the variables have the same meaning as described above. The examples presented below are intended to illustrate particular embodiments of the disclosure. Suitable starting materials, building blocks and reagents employed in the synthesis as described below are commercially available from Sigma-Aldrich or Acros Organics, for example, or can be routinely prepared by procedures described in the literature, for example in "March's Advanced Organic Chemistry: Reactions, Mechanisms, and Structure", 5$^{th}$ Edition; John Wiley & Sons or T. Eicher, S. Hauptmann "The Chemistry of Heterocycles; Structures, Reactions, Synthesis and Application", 2$^{nd}$ edition, Wiley-VCH 2003; Fieser et al. "Fiesers' Reagents for organic Synthesis" John Wiley & Sons 2000.

General Synthetic Scheme

Compounds of Formula (I) wherein Y is N can be synthesized according to the following general synthetic scheme.

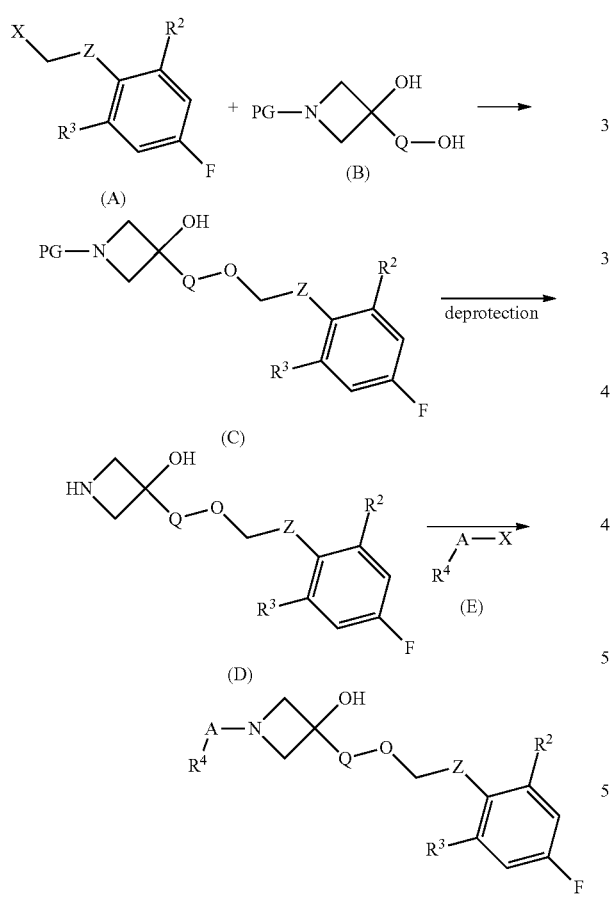

In the general synthetic scheme above, X is a leaving group, PG is a protecting group, and the remaining variables are as provided herein. A compound of formula (C) can be prepared by reacting a compound of formula (A) with a compound of formula (B) in the presence of a base to form a compound of formula (C). A compound of formula (D) is formed from a compound of formula (C) under appropriate deprotection conditions. A compound of formula (D) can be combined with a compound of formula (E) in the presence of a base to give a compound of Formula (I).

Appropriate compounds of structure (A) and (B) can be prepared according to the specific methods described in the following Examples or by methods known in the art. In some embodiments, X is halo. In some embodiments, PG is BOC.

General Synthesis 1

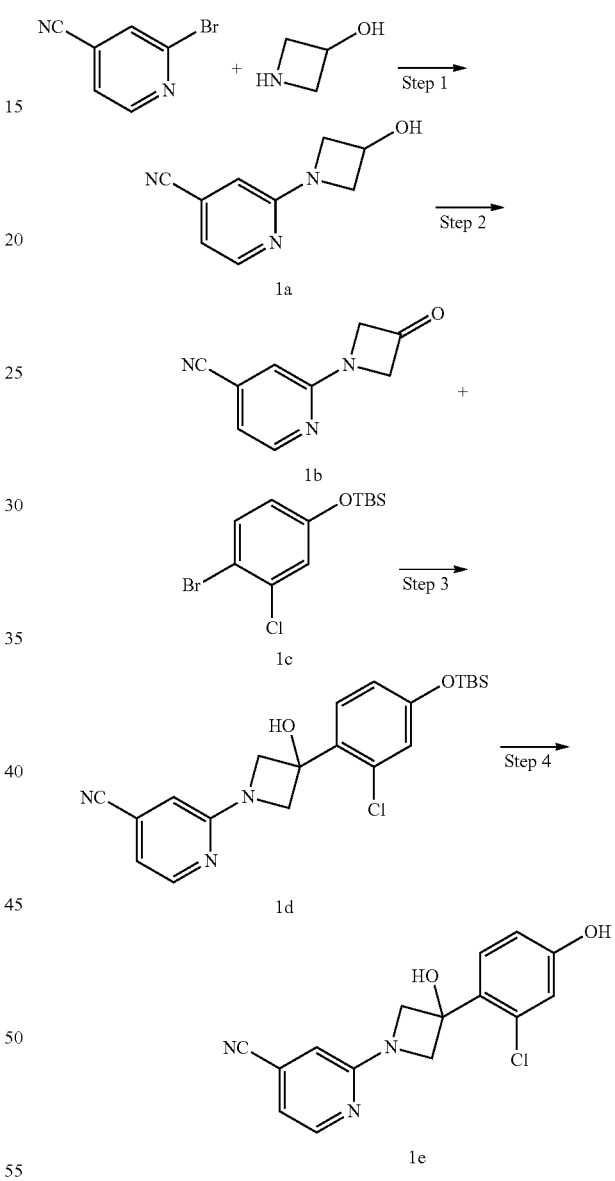

Step 1: 2-(3-hydroxyazetidin-1-yl)isonicotinonitrile (1a)

Potassium carbonate (4.6 g, 33 mmol) was added to 2-chloro-4-pyridinecarbonitrile (2.0 g, 14.4 mmol) and 3-hydroxyazetidine hydrochloride (1.7 g, 16 mmol) in NMP (12 mL) at room temperature, and the mixture was heated to 80° C. for 2 hrs in a sealed tube. The mixture was cooled to room temperature, treated with H$_2$O and extracted with EtOAc. The organic layers, were washed with brine, dried with Na₂SO₄ and concentrated. Purification by chromatography (ISCO 24 g silica column) using a gradient 1:1 hexanes/EtOAc—100% EtOAc gave 2-(3-hydroxyazetidin-1-yl)isonicotinonitrile (1a).

Step 2: 2-(3-oxoazetidin-1-yl)isonicotinonitrile (1b)

N-methylmorpholine (1.9 g, 16 mmol) then tetrapropylammonium perruthenate (190 mg, 0.5 mmol) were added to 2-(3-hydroxyazetidin-1-yl)isonicotinonitrile (1.9 g, 10.7 mmol) in CH₂Cl₂ (200 mL) with molecular sieves (1 g, activated powdered, 4 Å) at room temperature. After 20 minutes with vigorous stirring, the mixture was filtered through a pad of Celite and concentrated. Purification by chromatography (ISCO 24 g silica column) using a gradient 100% hexanes—1:3 hexanes/EtOAc gave 2-(3-oxoazetidin-1-yl)isonicotinonitrile (1b).

Synthesis of 1c: (4-bromo-3-chlorophenoxy)(tert-butyl)dimethylsilane (1c)

To the solution of 4-bromo-3-chlorophenol (250 g, 1.21 mol) and TBSCl (272 g, 1.81 mol) in DMF (2.0 L) was added imidazole (164 g, 2.41 mol). Then the reaction was stirred at 30° C. for 12 h. The reaction mixture was poured into H₂O (3 L) and extracted with EtOAc (2 L) twice. The combined organic layers were washed with H₂O (1 L) and brine (1 L), dried over Na₂SO₄, filtered and concentrated in vacuo. Purification by silica gel chromatography eluted with petroleum ether gave (4-bromo-3-chlorophenoxy)(tert-butyl)dimethylsilane (1c).

Step 3: 2-(3-(4-((tert-Butyldimethylsilyl)oxy)-2-chlorophenyl)-3-hydroxyazetidin-1-yl)isonicotinonitrile (1d)

Isopropylmagnesium chloride lithium chloride complex (1.3 ml, 1.7 mmol, 1.5 M in THF) was added dropwise to (4-bromo-3-chlorophenoxy)(tert-butyl)dimethylsilane (1c, 370 mg, 1.15 mmol) in THF (0.9 ml) at room temperature. After 3 h, the reaction was cooled to 0° C. and treated with 2-(3-oxoazetidin-1-yl)isonicotinonitrile (199 mg, 1.15 mmol) in one portion as a solid. After 1 h, the reaction was quenched with H₂O and EtOAc. The organic layer was washed with brine, dried with Na₂SO₄ and concentrated. Purification by chromatography (ISCO 4 g silica column) using a gradient 100% hexanes—1:3 hexanes/EtOAc gave 2-(3-(4-((tert-butyldimethylsilyl)oxy)-2-chlorophenyl)-3-hydroxyazetidin-1-yl)isonicotinonitrile (1d).

Step 4: 2-(3-(2-Chloro-4-hydroxyphenyl)-3-hydroxyazetidin-1-yl)isonicotinonitrile (1e)

To a solution of 2-(3-(4-((tert-butyldimethylsilyl)oxy)-2-chlorophenyl)-3-hydroxyazetidin-1-yl)isonicotinonitrile (1d) (180 mg, 0.43 mmol) in 2-MeTHF (4 mL) was added 1 M TBAF solution in THF (0.6 mL, 0.59 mmol) at room temperature. After 30 minutes, the mixture was quenched with water, extracted with EtOAc. The organic phase was washed with brine (10 mL), dried with Na₂SO₄, and concentrate to give 2-(3-(2-chloro-4-hydroxyphenyl)-3-hydroxyazetidin-1-yl)isonicotinonitrile (1e), which was used without further purification.

General Synthesis 2

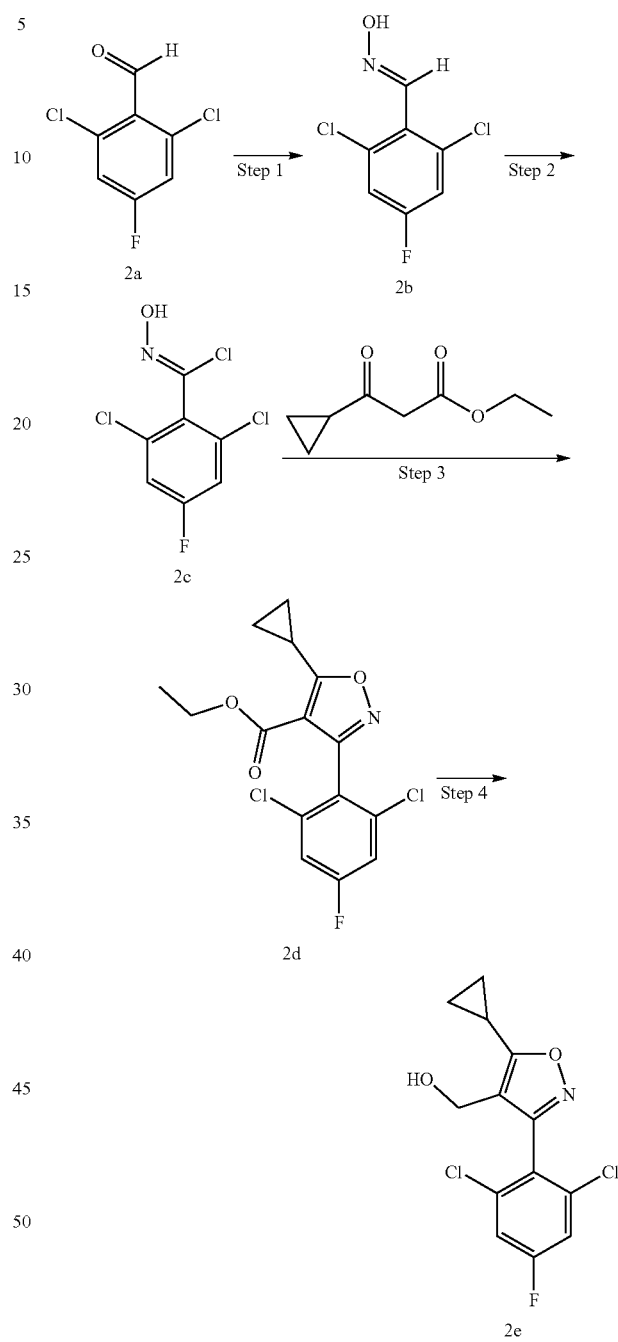

Step 1: 2,6-dichloro-4-fluorobenzaldehyde oxime (2b)

A suspension of 2,6-dichloro-4-fluorobenzaldehyde (6.0 g, 31.2 mmol), NH₂OH·HCl (4.3 g, 62.4 mmol), Na₂CO₃ (8.3 g, 78.7 mmol) in ethanol-water (50 ml, 5:1) was stirred at room temperature for 3 h. The reaction was condensed under vacuum and the residue was treated with water followed by extraction with ethyl acetate. The ethyl acetate layer was washed with brine, dried over Na₂SO₄, and concentrated to afford 2,6-dichloro-4-fluorobenzaldehyde oxime (2b).

Step 2: 2,6-dichloro-4-fluoro-N-hydroxybenzimidoyl chloride (2c)

To a solution of 2,6-dichloro-4-fluorobenzaldehyde oxime (2b, 5.5 g, 26.7 mmol) in DMF (10 mL) was added N-chlorosuccinimide (4.3 g, 32.0 mmol). The reaction was stirred at RT for 1 h. The mixture quenched with H₂O and extracted with EtOAc. The combined organic layers were washed with brine, dried over anhydrous Na₂SO₄, filtered and concentrated to give the 2,6-dichloro-4-fluoro-N-hydroxybenzimidoyl chloride (2c) that was used without further purification in the next step.

Step 3: ethyl 5-cyclopropyl-3-(2,6-dichloro-4-fluorophenyl)isoxazole-4-carboxylate (2d)

To a solution of 3-cyclopropyl-3-oxo-propionic acid ethyl ester (5.0 g, 32.0 mmol) in 30 mL THF was added Et₃N (10.8 g, 107.2 mmol), the reaction was stirred at RT for 30 min, then the reaction mixture from the previous step (2,6-dichloro-4-fluoro-N-hydroxybenzimidoyl chloride (2c)) was added dropwise. The resulting mixture was stirred for 2 h at RT. The solvent was removed and the residue was partitioned with 100 mL water and 50 mL EtOAc. The organic layer was washed with brine, dried, filtered, concentrated and purified by silica gel column (PE/EA=10/1) to give ethyl 5-cyclopropyl-3-(2,6-dichloro-4-fluorophenyl) isoxazole-4-carboxylate (2d).

Step 4: (5-cyclopropyl-3-(2,6-dichloro-4-fluorophenyl)isoxazol-4-yl)methanol (2e)

To the solution of ethyl 5-cyclopropyl-3-(2,6-dichloro-4-fluorophenyl)isoxazole-4-carboxylate (2d, 3.4 g, 9.3 mmol) in THF (30 ml) was added LiAlH₄ (11.1 ml, 11.1 mmol, 1 M in hexane) dropwise at 0° C. The reaction was stirred for 30 min. 1.0 ml water was added, then 2.0 g 10% NaOH, 3.0 mL water were added. The mixture was filtered and concentrated. The crude was purified by silica gel column (PE/EA=2/1) to give (5-cyclopropyl-3-(2,6-dichloro-4-fluorophenyl)isoxazol-4-yl)methanol (2e). LCMS (ESI): m/z 302.0 (M+1)⁺. ¹H NMR (500 MHz, CDCl₃): δ 7.22-7.20 (d, J=8.5 Hz, 2H), 4.42-4.41 (d, J=6.0 Hz, 2H), 2.19-2.16 (m, 1H), 1.41-1.39 (m, 1H), 1.29-1.26 (m, 2H), 1.16-1.13 (m, 2H).

General Synthesis 3

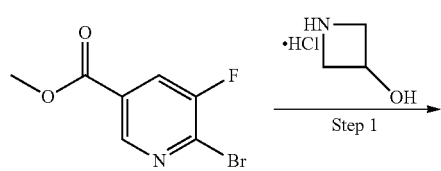

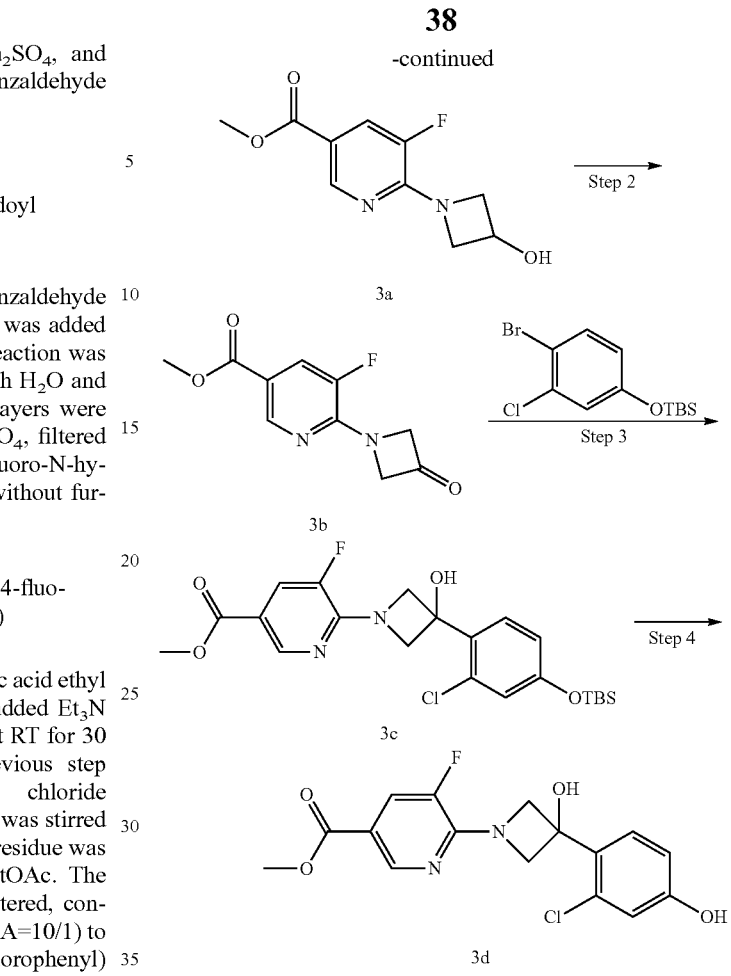

Step 1: methyl 5-fluoro-6-(3-hydroxyazetidin-1-yl)nicotinate (3a)

A mixture of azetidin-3-ol hydrochloride (2.8 g, 26 mmol), methyl 6-bromo-5-fluoronicotinate (5.0 g, 21 mmol), and potassium carbonate (7.4 g, 53 mmol) in DMF (100 mL) was heated at 65° C. for 19 hours. The mixture was purified by flash chromatography (silica gel) to provide the desired product. LCMS-ESr (m/z): [M+H]⁺ calcd for C₁₀H₁₂FN₂O₃: 227.1; found: 227.0.

Step 2: methyl 5-fluoro-6-(3-oxoazetidin-1-yl)nicotinate (3b)

A solution of methyl 5-fluoro-6-(3-hydroxyazetidin-1-yl) nicotinate (4.7 g, 21 mmol) in dichloromethane (270 mL) was treated with Dess-Martin periodinane (9.7 g, 23 mmol). After 6 hours of stirring at room temperature, an additional portion of Dess-Martin periodinane (1.5 g) was added, and the mixture was allowed to stir overnight at room temperature. After stirring overnight, the mixture was treated with aqueous sodium thiosulfate solution and saturated aqueous sodium hydrogen carbonate solution. The aqueous phase was extracted three times with dichloromethane. The combined extracts were dried over anhydrous magnesium sulfate, filtered, concentrated to dryness under reduced pressure. The residue was purified twice by flash chromatography (silica gel) to provide the desired material. LCMS-ESI⁺ (m/z): [M+H2O+H]⁺ calcd for C₁₀H₁₂FN₂O₄: 243.1; found: 243.0.

Step 3: methyl 6-(3-(4-((tert-butyldimethylsilyl)oxy)-2-chlorophenyl)-3-hydroxyazetidin-1-yl)-5-fluoronicotinate (3c)

A solution of (4-bromo-3-chlorophenoxy)(tert-butyl)dimethylsilane (4.5 g, 14 mmol) in 2-methyltetrahydrofuran (14 mL) was treated with isopropylmagnesium chloride/lithium chloride solution (Aldrich, 1.3M, 11 mL, 15 mmol) dropwise via syringe. The resulting mixture was stirred for approximately one hour and then was cooled in an ice-water bath. Methyl 5-fluoro-6-(3-oxoazetidin-1-yl)nicotinate (2.0 g, 8.9 mmol) was added portions over 2 hours. The mixture was allowed to stand overnight at room temperature. The mixture was quenched with 10% aqueous citric acid solution. The aqueous phase was extracted three times with ethyl acetate. The combined organics were washed once with saturated aqueous sodium chloride solution, dried over anhydrous magnesium sulfate, filtered, and concentrated under reduced pressure to provide the crude desired product which was carried forward without further purification. LCMS-ESI$^+$ (m/z): [M+H]$^+$ calcd for $C_{22}H_{29}ClFN_2O_4Si$: 467.2; found: 467.1.

Step 4: methyl 6-(3-(2-chloro-4-hydroxyphenyl)-3-hydroxyazetidin-1-yl)-5-fluoronicotinate (3d)

Crude methyl 6-(3-(4-((tert-butyldimethylsilyl)oxy)-2-chlorophenyl)-3-hydroxyazetidin-1-yl)-5-fluoronicotinate (approximately 10 mmol) was taken up in tetrahydrofuran (70 mL) and treated with tetra-n-butylammonium fluoride solution (Aldrich, 1.0 M in THF, 18 mL, 18 mmol). The mixture was allowed to stand at room temperature until deemed complete by LC/MS and then purified by flash chromatography (silica gel) to provide Intermediate 3d. LCMS-ESr (m/z): [M+H]$^+$ calcd for $C_{16}H_{15}ClFN_2O_4$: 353.1; found: 353.0.

Example 1

5-((4-Bromo-3-chlorophenoxy)methyl)-4-cyclopropyl-1-(2,6-dichlorophenyl)-1H-pyrazole

Step 1: 2,4-difluorobenzaldehyde oxime

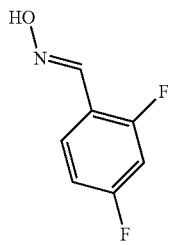 [SMILES: O/N=C/c1ccc(F)cc1F]

This compound was synthesized according to the procedure as described in General Synthesis 2, Step 1 starting with 2,4-difluorobenzaldehyde (10 g, 70 mmol).

Step 2: 2,4-difluoro-N-hydroxybenzimidoyl chloride

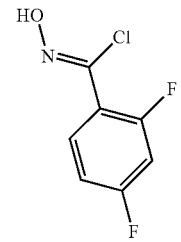 [SMILES: O/N=C(\Cl)c1ccc(F)cc1F]

This compound was synthesized according to the procedure as described in General Synthesis 2, Step 2 starting with 2,4-difluorobenzaldehyde oxime (9 g, 57 mmol).

Step 3: ethyl 5-cyclopropyl-3-(2,4-difluorophenyl)isoxazole-4-carboxylate

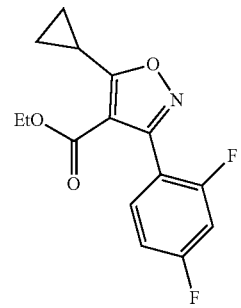 [SMILES: CCOC(=O)c1c(-c2ccc(F)cc2F)noc1C1CC1]

This compound was synthesized according to the procedure as described in General Synthesis 2, Step 3 starting with 2,4-difluoro-N-hydroxybenzimidoyl chloride (11 g, 57 mmol).

Step 4: (5-cyclopropyl-3-(2,4-difluorophenyl)isoxazol-4-yl)methanol

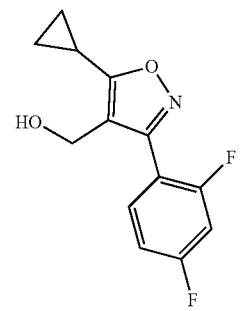 [SMILES: OCc1c(-c2ccc(F)cc2F)noc1C1CC1]

This compound was synthesized according to the procedure as described in General Synthesis 2, Step 4 starting with ethyl 5-cyclopropyl-3-(2,4-difluorophenyl)isoxazole-4-carboxylate (2.2 g, 8 mmol).

Step 5: 4-(Chloromethyl)-5-cyclopropyl-3-(2,4-difluorophenyl)isoxazole

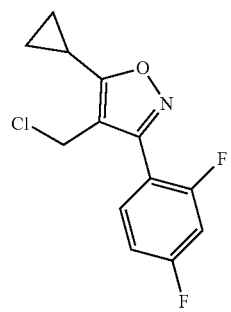 [SMILES: Fc1ccc(-c2noc(C3CC3)c2CCl)c(F)c1]

To a solution of (5-cyclopropyl-3-(2,4-difluorophenyl)isoxazol-4-yl)methanol (113 mg, 0.45 mmol) in CH$_2$Cl$_2$ (2.3 mL) was added thionyl chloride (164 µL, 2.3 mmol) at 0° C. The mixture was heated to reflux for 15 min and cooled to room temperature. The mixture was concentrated in vacuo. Additional CH$_2$Cl$_2$ (5 mL) was added and the mixture was concentrated again. This process was repeated a third time to remove excess thionyl chloride. The crude residue was used in the next step without further purification.

Step 6: 2-(3-(2-Chloro-4-((5-cyclopropyl-3-(2,4-difluorophenyl)isoxazol-4-yl)methoxy)phenyl)-3-hydroxyazetidin-1-yl)isonicotinonitrile

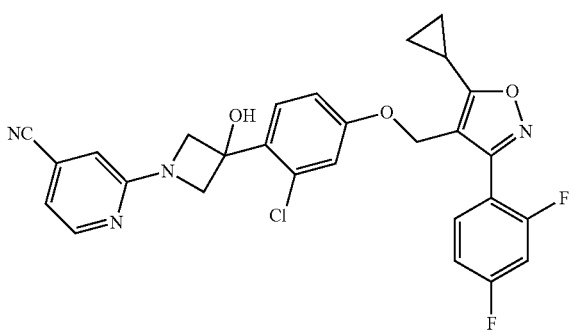 [SMILES: N#Cc1ccnc(N2CC(O)(c3ccc(OCc4c(-c5ccc(F)cc5F)noc4C4CC4)cc3Cl)C2)c1]

4-(chloromethyl)-5-cyclopropyl-3-(2,4-difluorophenyl)isoxazole (113 mg, 0.45 mmol), 2-(3-(2-chloro-4-hydroxyphenyl)-3-hydroxyazetidin-1-yl)isonicotinonitrile (Intermediate 1e) (149 mg, 0.5 mmol) and K$_2$CO$_3$ (124 mg, 0.9 mmol) were combined in anhydrous DMF (2.3 mL) at room temperature. The mixture was heated to 65° C. under nitrogen. After 2 h, the solution was cooled to room temperature, quenched with H$_2$O and extracted with EtOAc. The combined organic layers were washed with brine, dried over anhydrous Na$_2$SO$_4$, filtered and concentrated. Purification by chromatography: ISCO (12 g silica column) using a gradient of 100% CH$_2$Cl$_2$–3:1 CH$_2$Cl$_2$/premixed 60:35:5 CH$_2$Cl$_2$:Et$_2$O:MeOH gave the title compound.

Step 7: 2-(3-(2-chloro-4-((5-cyclopropyl-3-(2,4-difluorophenyl)isoxazol-4-yl)methoxy)phenyl)-3-hydroxyazetidin-1-yl)isonicotinic acid (Example 1)

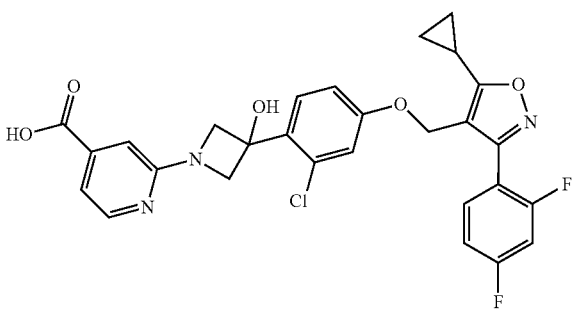 [SMILES: O=C(O)c1ccnc(N2CC(O)(c3ccc(OCc4c(-c5ccc(F)cc5F)noc4C4CC4)cc3Cl)C2)c1]

10 M aqueous sodium hydroxide (0.67 ml) was added to 2-(3-(2-chloro-4-((5-cyclopropyl-3-(2,4-difluorophenyl)isoxazol-4-yl)methoxy)phenyl)-3-hydroxyazetidin-1-yl)isonicotinonitrile (210 mg, 0.39 mmol) in ethanol (2 mL) and H$_2$O (2 mL) at room temperature and the mixture was heated at 60° C. for 90 minutes in a sealed tube. The mixture was cooled to room temperature and adjusted pH to about 5 with 1 M HCl which caused a precipitate to fall out of solution. The solution was filtered and the solid was rinsed with Et$_2$O and dried in vacuo to give 2-(3-(2-chloro-4-((5-cyclopropyl-3-(2,4-difluorophenyl)isoxazol-4-yl)methoxy)phenyl)-3-hydroxyazetidin-1-yl)isonicotinic acid (Example 1). $^1$H NMR (300 MHz, DMSO-d6) $^1$H NMR (300 MHz, DMSO-d$_6$) δ 13.41 (s, 1H), 8.19 (dd, J=5.2, 0.8 Hz, 1H), 7.59 (td, J=8.5, 6.5 Hz, 1H), 7.49-7.34 (m, 2H), 7.28-7.15 (m, 1H), 7.05-6.96 (m, 2H), 6.88-6.74 (m, 2H), 6.20 (s, 1H), 5.00 (s, 2H), 4.47 (d, J=9.3 Hz, 2H), 4.18 (d, J=9.2 Hz, 2H), 2.40 (tt, J=8.3, 5.3 Hz, 1H), 1.20-1.00 (m, 4H). MS (ESI$^+$) (m/z) 554.0 (M+H).

Example 2
2-(3-(2-chloro-4-((5-cyclopropyl-3-(2,6-dichloro-4-fluorophenyl)isoxazol-4-yl)methoxy)phenyl)-3-hydroxyazetidin-1-yl)isonicotinic Acid
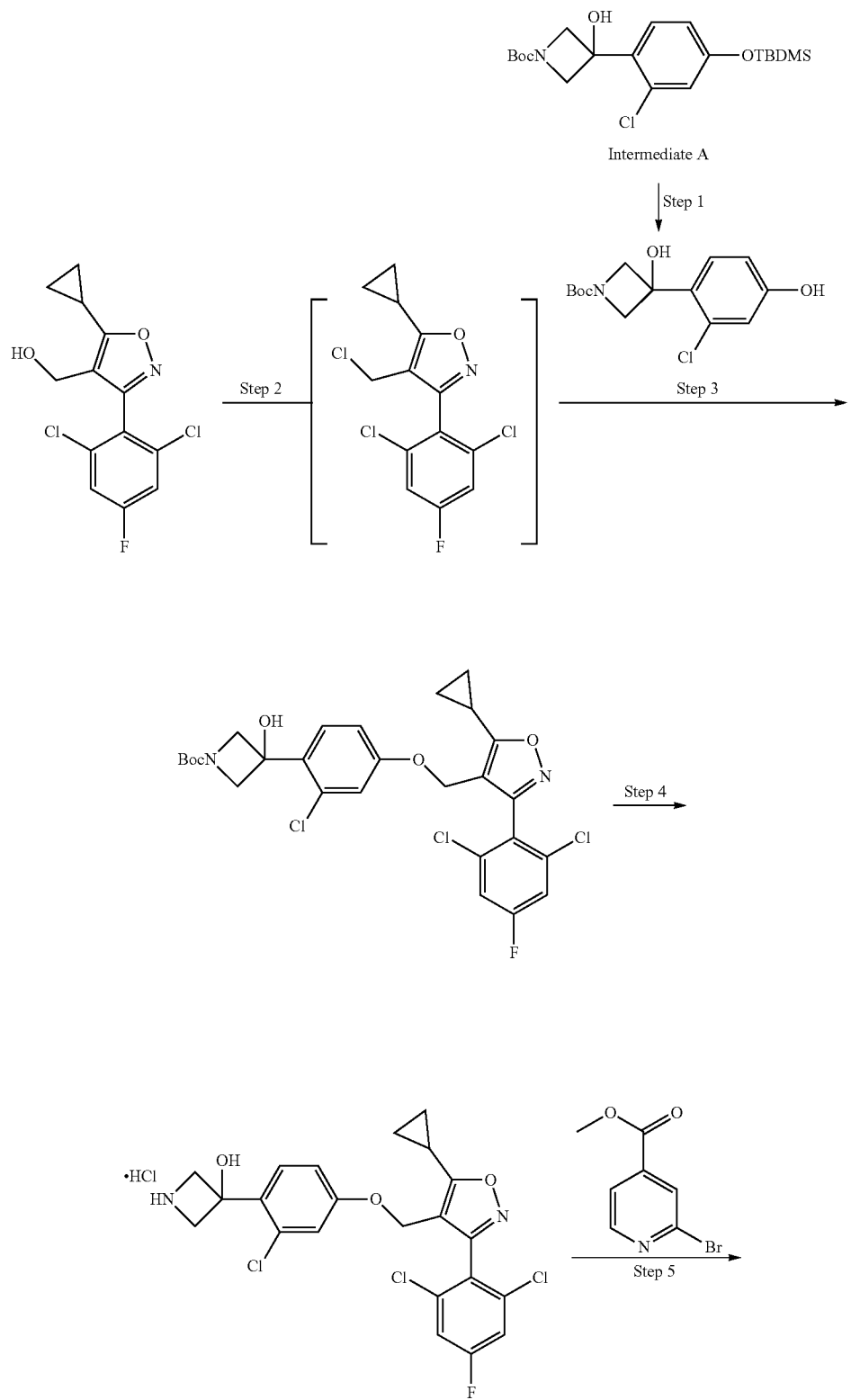

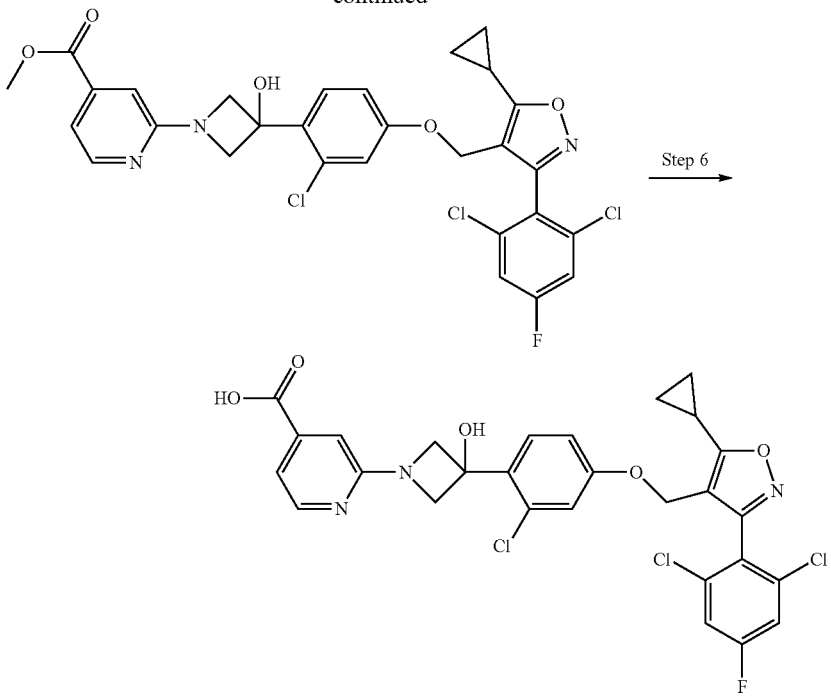

Example 2

Synthesis of Intermediate A

To a solution of (4-bromo-3-chlorophenoxy)(tert-butyl)dimethylsilane (1c, 60 g, 187 mmol) in THF (500 mL) was added dropwise n-BuLi (2.5 M, 75 mL) at −78° C. under N$_2$. The reaction was stirred at −78° C. for 1 h. Next a solution of tert-butyl 3-oxoazetidine-1-carboxylate (27 g, 155 mmol) in THF (500 mL) was added dropwise to the mixture at −78° C. Then the reaction was stirred at 20° C. for 3 h. The reaction mixture was poured into H$_2$O (1 L) and extracted with EtOAc (2 L) three times. The combined organic layers were washed with water (1 L), dried over Na$_2$SO$_4$, filtered and concentrated in vacuo. The crude product was purified by silica gel chromatography eluted with 10:1 petroleum ether:EtOAc to give 3-(4-((tert butyldimethylsilyl)oxy)-2-chlorophenyl)azetidin-3-ol (Intermediate A).

Step 1: tert-butyl 3-(2-chloro-4-hydroxyphenyl)-3-hydroxyazetidine-1-carboxylate To a solution of tert-butyl 3-(4-((tert-butyldimethylsilyl)oxy)-2-chlorophenyl)-3-hydroxyazetidine-1-carboxylate (Intermediate A, 1.27 g, 3.07 mmol) in THF (50.0 mL) at −10° C. was added 1M TBAF in THF (3.68 mL, 3.68 mmol) dropwise. The reaction was stirred for 2 hours and was concentrated to afford tert-butyl 3-(2-chloro-4-hydroxyphenyl)-3-hydroxyazetidine-1-carboxylate, which was used without further purification.

Step 2: 4-(chloromethyl)-5-cyclopropyl-3-(2,6-dichloro-4-fluorophenyl)isoxazole A solution of (5-cyclopropyl-3-(2,6-dichloro-4-fluorophenyl)isoxazol-4-yl)methanol (2e); 845 mg, 2.80 mmol) in DCM (28.0 mL) was cooled to 0° C. Thionyl chloride (1.02 mL, 14.0 mmol) was added and the solution was heated at 45° C. for 1 hour. The reaction was concentrated to dryness and used without purification in the next step.

Step 3: tert-butyl 3-(2-chloro-4-((5-cyclopropyl-3-(2,6-dichloro-4-fluorophenyl)isoxazol-4-yl)methoxy)phenyl)-3-hydroxyazetidine-1-carboxylate A solution of tert-butyl 3-(2-chloro-4-hydroxyphenyl)-3-hydroxyazetidine-1-carboxylate (922 mg, 3.07 mmol) in DMF (28.0 mL) was added to crude 4-(chloromethyl)-5-cyclopropyl-3-(2,6-dichloro-4-fluorophenyl)isoxazole, followed by the addition of potassium carbonate (773 mg, 5.60 mmol). The mixture was heated at 60° C. for 8 hours. The reaction was concentrated, diluted with water and extracted with EtOAc (3×). The combined organic layers were washed with water, brine, dried over MgSO$_4$, filtered and concentrated. The crude product was purified by silica gel chromatography (DCM/Et$_2$O/MeOH) to afford tert-butyl 3-(2-chloro-4-((5-cyclopropyl-3-(2,6-dichloro-4-fluorophenyl)isoxazol-4-yl)methoxy)phenyl)-3-hydroxyazetidine-1-carboxylate. LCMS-ESr (m/z): [(M+H)—BOC]$^+$ calcd 483.04; found 483.04.

Step 4: 3-(2-chloro-4-((5-cyclopropyl-3-(2,6-dichloro-4-fluorophenyl)isoxazol-4-yl)methoxy)phenyl)azetidin-3-ol To a solution of tert-butyl 3-(2-chloro-4-((5-cyclopropyl-3-(2,6-dichloro-4-fluorophenyl)isoxazol-4-yl)methoxy)phenyl)-3-hydroxyazetidine-1-carboxylate (1.52 g, 2.60 mmol) in DCM (130 mL) was added 4 N HCl in 1,4-dioxane (26.0 mL, 104 mmol). The solution was stirred at room temperature for 2.5 hours and was concentrated to dryness to afford 3-(2-chloro-4-((5-cyclopropyl-3-(2,6-dichloro-4-fluorophenyl)isoxazol-4-yl)methoxy)phenyl)azetidin-3-ol as the hydrochloride salt, which was used without further purification. LCMS-ESr (m/z): [M+H]+ calcd 483.04; found 483.03.

Step 5: methyl 2-(3-(2-chloro-4-((5-cyclopropyl-3-(2,6-dichloro-4-fluorophenyl)isoxazol-4-yl)methoxy)phenyl)-3-hydroxyazetidin-1-yl)isonicotinate A mixture of methyl 2-bromopyridine-4-carboxylate (0.466 g, 2.16 mmol), 3-(2-chloro-4-((5-cyclopropyl-3-(2,6-dichloro-4-fluorophenyl)isoxazol-4-yl)methoxy)phenyl)azetidin-3-ol as the hydrochloride salt (1.02 g, 1.96 mmol), cesium carbonate (2.56 g, 7.85 mmol), (±)-BINAP (0.244 g, 0.392 mmol), palladium acetate trimer (88.0 mg, 0.131 mmol) and 1,4-dioxane (40.0 mL) was heated at 85° C. for 18 hours. The reaction was cooled to room temperature, filtered over celite and purified by silica gel chromatography (acetone/hexanes) to afford methyl 2-(3-(2-chloro-4-((5-cyclopropyl-3-(2,6-dichloro-4-fluorophenyl)isoxazol-4-yl)methoxy)phenyl)-3-hydroxyazetidin-1-yl)isonicotinate. LCMS-ESr (m/z): [M+H]+ calcd 618.08; found 618.20.

Step 6: 2-(3-(2-chloro-4-((5-cyclopropyl-3-(2,6-dichloro-4-fluorophenyl)isoxazol-4-yl)methoxy)phenyl)-3-hydroxyazetidin-1-yl)isonicotinic Acid (Example 2)

To a solution of 2-(3-(2-chloro-4-((5-cyclopropyl-3-(2,6-dichloro-4-fluorophenyl)isoxazol-4-yl)methoxy)phenyl)-3-hydroxyazetidin-1-yl)isonicotinate (617 mg, 0.997 mmol) in THF/water (1:1, 10 mL) was added lithium hydroxide monohydrate (83.6 mg, 1.99 mmol). The solution was stirred for 90 minutes, concentrated to remove THF and diluted with water. Acetic acid (0.23 mL, 3.99 mmol) was added while stirring which resulted in the precipitation of solids. The solids were filtered, washed with water, IPA and ether, and dried under vacuum to afford 2-(3-(2-chloro-4-((5-cyclopropyl-3-(2,6-dichloro-4-fluorophenyl)isoxazol-4-yl)methoxy)phenyl)-3-hydroxyazetidin-1-yl)isonicotinic acid (Example 2). LCMS-ESI+ (m/z): [M+H]+ calcd 604.06; found 604.15. $^1$H NMR (300 MHz, DMSO-d$_6$) δ 13.47 (br s, 1H), 8.18 (dd, J=5.3, 0.8 Hz, 1H), 7.69 (d, J=8.5 Hz, 2H), 7.37 (d, J=8.7 Hz, 1H), 7.02 (dd, J=5.3, 1.4 Hz, 1H), 6.93 (d, J=2.6 Hz, 1H), 6.86 (br s, 1H), 6.75 (dd, J=8.6, 2.6 Hz, 1H), 6.20 (s, 1H), 4.91 (s, 2H), 4.49 (d, J=9.3 Hz, 2H), 4.19 (d, J=9.3 Hz, 2H), 2.46-2.37 (m, 1H), 1.23-1.04 (m, 4H).

Example 3

6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinic Acid

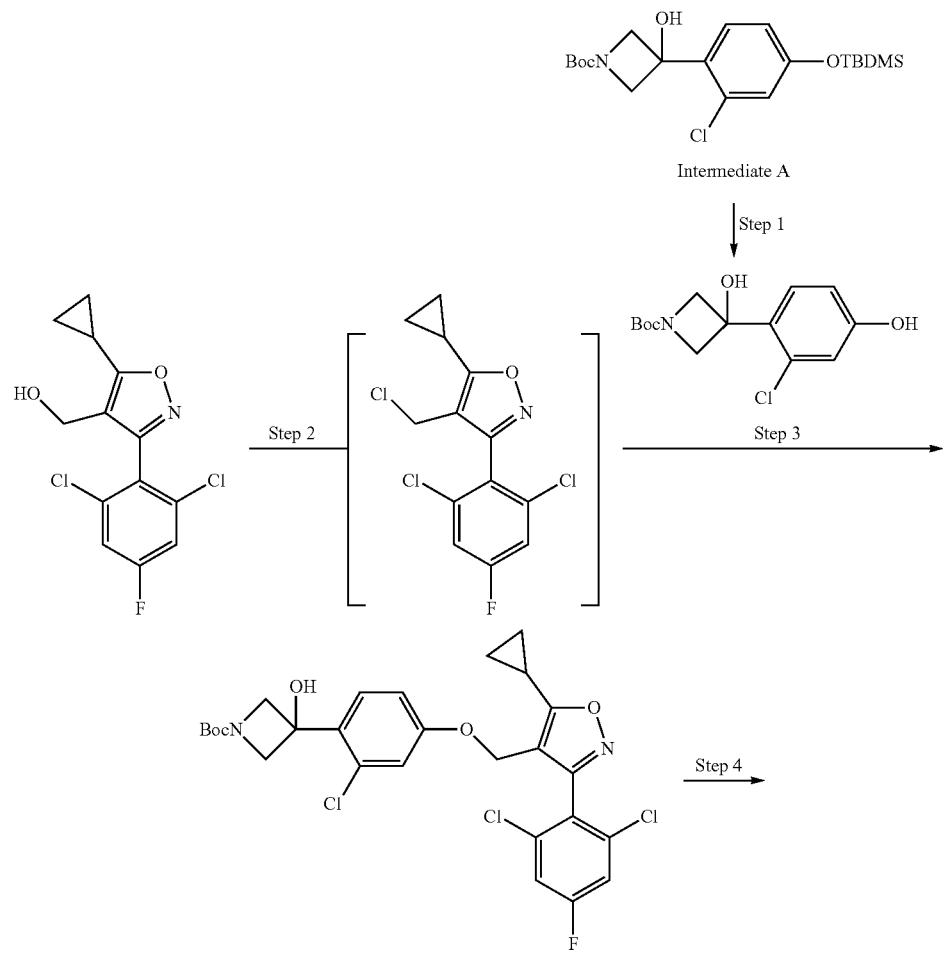

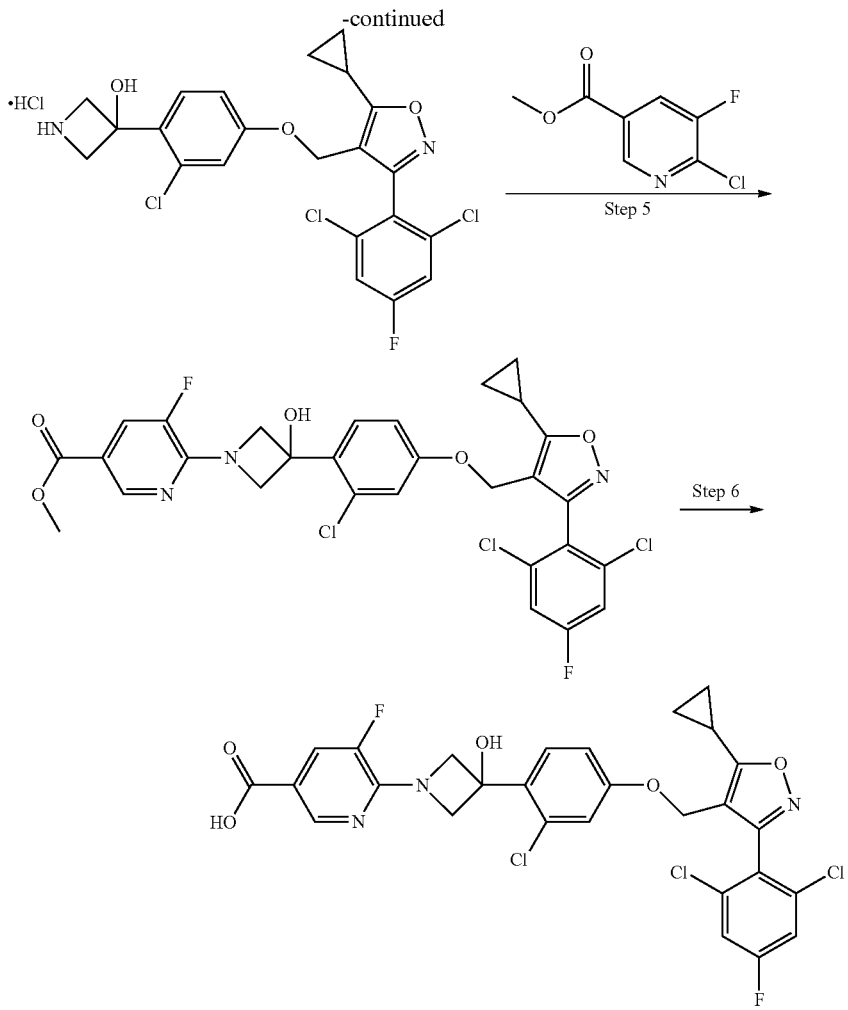

Example 3

Steps 1-4 were as described for the synthesis of Example 2.

Step 5: methyl 6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinate A mixture of methyl 6-chloro-5-fluoropyridine (235 mg, 1.24 mmol), 3-(2-chloro-4-((5-cyclopropyl-3-(2,6-dichloro-4-fluorophenyl)isoxazol-4-yl)methoxy)phenyl)azetidin-3-ol as the hydrochloride salt (495 mg, 0.952 mmol) and potassium carbonate (1.05 g, 7.61 mmol) in DMF (30.0 mL) was heated at 60° C. for 1 hour. The reaction was concentrated, diluted with water and extracted with EtOAc (3×). The combined organic layers were washed with brine, dried over MgSO₄, filtered and concentrated. The crude mixture was purified by silica gel chromatography (DCM/Et₂O/MeOH) to afford methyl 6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinate. LCMS-ESI⁺ (m/z): [M+H]⁺ calcd 636.07; found 635.96.

Step 6: 6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinic Acid (Example 3)

To a solution of methyl 6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinate (364 mg, 0.571 mmol) in THF/water (1:1, 20.0 mL) was added lithium hydroxide monohydrate (41.3 mg, 0.984 mmol). The solution was stirred for 18 hours, concentrated to remove THF and diluted with water (10.0 mL). The pH was adjusted to 3 using 1N HCl. The solids were filtered, washed with water, dissolved in ACN/water and lyophilized to afford 6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinic acid (Example 3). LCMS-ESI⁺ (m/z): [M+H]⁺ calcd 622.05; found 622.12. ¹H NMR (400 MHz, DMSO-d₆) δ 12.84 (bs, 1H), 8.44 (t, J=1.7 Hz, 1H), 7.79-7.63 (m, 3H), 7.39 (d, J=8.7 Hz, 1H), 6.95 (d, J=2.5 Hz, 1H), 6.77 (dd, J=8.6, 2.6 Hz, 1H), 6.28 (s, 1H), 4.93 (s, 2H), 4.70 (d, J=9.8 Hz, 2H), 4.34 (d, J=9.5 Hz, 2H), 2.50-2.43 (m, 1H), 1.22-1.08 (m, 4H).

51

Intermediate 4: (3-(2,6-dichloro-4-fluorophenyl)-5-methylisoxazol-4-yl)methanol

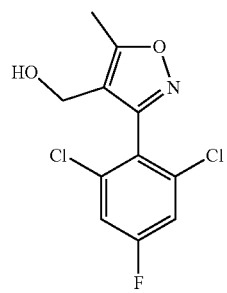 [SMILES: Cc1onc(-c2c(Cl)cc(F)cc2Cl)c1CO]

Following General Synthesis 2, beginning with 2,6-dichloro-4-fluorobenzaldehyde in Step 1 and using ethyl acetoacetate in Step 3, (3-(2,6-dichloro-4-fluorophenyl)-5-methylisoxazol-4-yl)methanol (Intermediate 4) was synthesized. LCMS-ESr (m/z): [M+H]$^+$ calcd 276.00; found 276.05.

Example 4

Preparation of 6-(3-(2-chloro-4-((3-(2,6-dichloro-4-fluorophenyl)-5-methylisoxazol-4-yl)methoxy)phenyl)-3-hydroxyazetidin-1-yl)-5-fluoronicotinic Acid

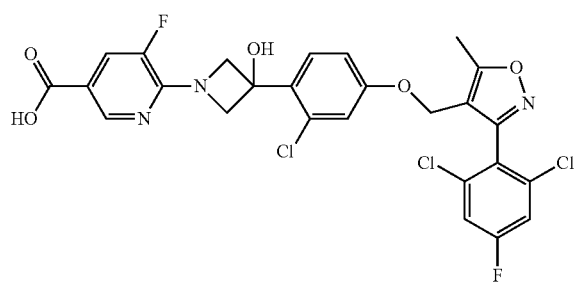 [SMILES: Cc1onc(-c2c(Cl)cc(F)cc2Cl)c1COc1ccc(C2(O)CN(c3ncc(C(=O)O)cc3F)C2)c(Cl)c1]

Following the general procedure described for Example 3, using intermediate 4, 6-(3-(2-chloro-4-((3-(2,6-dichloro-4-fluorophenyl)-5-methylisoxazol-4-yl)methoxy)phenyl)-3-hydroxyazetidin-1-yl)-5-fluoronicotinic acid was synthesized. LCMS-ESI$^+$ (m/z): [M+H]$^+$ calcd 596.04; found 596.12. $^1$H NMR (400 MHz, DMSO-d$_6$) δ 12.82 (bs, 1H), 8.44 (t, J=1.6 Hz, 1H), 7.74-7.66 (m, 3H), 7.39 (d, J=8.7 Hz, 1H), 6.90 (d, J=2.6 Hz, 1H), 6.75 (dd, J=8.7, 2.6 Hz, 1H), 6.26 (s, 1H), 4.87 (s, 2H), 4.69 (d, J=9.8 Hz, 2H), 4.34 (d, J=9.8 Hz, 2H), 2.57 (s, 3H).

52

Example 5

6-(3-(2-chloro-4-((4-cyclopropyl-1-(2,6-dichloro-4-fluorophenyl)-1H-pyrazol-5-yl)methoxy)phenyl)-3-hydroxyazetidin-1-yl)-5-fluoronicotinic Acid

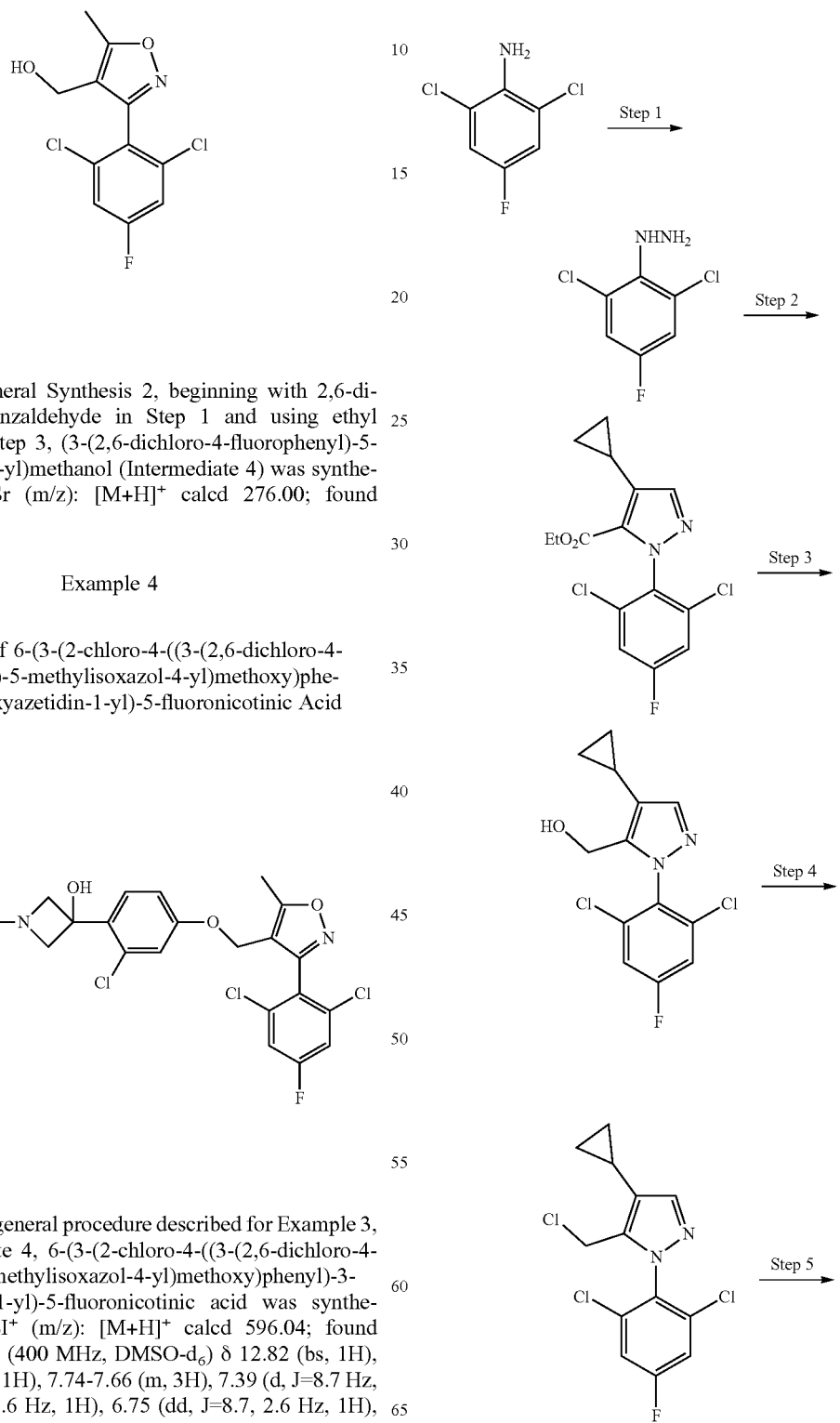

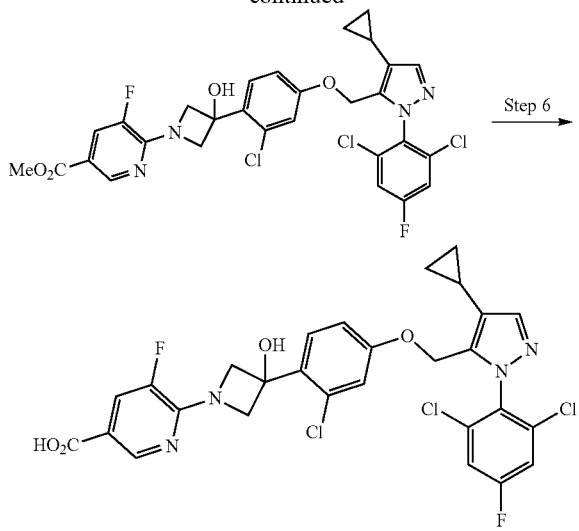

Example 5

Step 1: (2,6-dichloro-4-fluorophenyl)hydrazine hydrochloride

To a −5° C. solution (internal temperature, wet ice/acetone bath) of 2,6-dichloro-4-fluoroaniline (3.0 g, 17 mmol) in 37% hydrochloric acid (30 mL) and trifluoroacetic acid (20 mL) was added dropwise an aqueous solution of sodium nitrite (1.4 g, 20 mmol, 6 mL water). The reaction was stirred for 90 minutes, then a solution of stannous chloride dihydrate (5.6 g, 25 mmol) in 37% hydrochloric acid (16 mL) was added over 15 minutes, keeping the internal temperature ≤2° C. The mixture was stirred overnight at room temperature. The mixture was filtered and the collected solid was washed with isopropyl alcohol and dried under house vacuum to provide the title compound. LCMS-ESI+ (m/z): [M+H]+ calcd for $C_6H_6Cl_2FN_2$: 195.0; found: 194.9.

Step 2: ethyl 4-cyclopropyl-1-(2,6-dichloro-4-fluorophenyl)-1H-pyrazole-5-carboxylate N,N-Dimethylformamide dimethyl acetal (2.7 mL, 20 mmol) was added to ethyl 3-cyclopropyl-2-oxopropanoate (Synnovator, 1.6 g, 10 mmol) and stirred overnight at room temperature. The mixture was then concentrated to dryness under reduced pressure. To the residue was added successively ethanol (40 mL), (2,6-dichloro-4-fluorophenyl)hydrazine hydrochloride (2.6 g, 11 mmol), and 37% hydrochloric acid (150 µL). The reaction was stirred at room temperature for four hours, followed by 2 days of heating at reflux. The cooled mixture was purified by flash chromatography (silica gel) to provide the title compound. LCMS-ESI+ (m/z): [M+H]+ calcd for $C_{15}H_{14}C_2FN_2O_2$: 343.0; found: 343.1.

Step 3: (4-cyclopropyl-1-(2,6-dichloro-4-fluorophenyl)-1H-pyrazol-5-yl)methanol A solution of ethyl 4-cyclopropyl-1-(2,6-dichloro-4-fluorophenyl)-1H-pyrazole-5-carboxylate (1.5 g, 4.4 mmol) in tetrahydrofuran (50 mL) was cooled to between −12 and −10° C. A solution of lithium aluminum hydride (Aldrich, 2 M in tetrahydrofuran, 2.6 mL, 5.2 mmol) was added dropwise. The mixture was allowed to stir for 35 minutes. The mixture was quenched (Fieser procedure) and purified by flash chromatography (silica gel) to provide the title compound. LCMS-ESI+ (m/z): [M+H]+ calcd for $C_{13}H_{12}Cl_2FN_2O$: 301.0; found: 301.1.

Step 4: 5-(chloromethyl)-4-cyclopropyl-1-(2,6-dichloro-4-fluorophenyl)-1H-pyrazole Thionyl chloride (110 µL, 1.5 mmol) was added to a solution of (4-cyclopropyl-1-(2,6-dichloro-4-fluorophenyl)-1H-pyrazol-5-yl)methanol (0.15 g, 0.51 mmol) in dichloromethane (2.5 mL). The mixture was heated at 60° C. for 40 minutes and then concentrated under reduced pressure to provide the crude desired product, which was carried forward without further purification. LCMS-ESI+ (m/z): [M+H]+ calcd for $C_{13}H_{11}Cl_3FN_2$: 319.0; found: 319.1.

Step 5: methyl 6-(3-(2-chloro-4-((4-cyclopropyl-1-(2,6-dichloro-4-fluorophenyl)-1H-pyrazol-5-yl)methoxy)phenyl)-3-hydroxyazetidin-1-yl)-5-fluoronicotinate A solution of 4-(chloromethyl)-5-cyclopropyl-3-(2,6-dichloro-4-fluorophenyl)isoxazole (0.16 g, 0.51 mmol) in DMF (3 mL) was treated with methyl 6-(3-(2-chloro-4-hydroxyphenyl)-3-hydroxyazetidin-1-yl)-5-fluoronicotinate (0.20 g, 0.56 mmol), sodium iodide (0.13 g, 0.86 mmol), and potassium carbonate (0.14 g, 1.0 mmol). The mixture was heated 65° C. overnight and then purified by flash chromatography (silica gel) to provide the desired material. LCMS-ESI+ (m/z): [M+H]+ calcd for $C_{29}H_{24}Cl_3F_2N_4O_4$: 635.1; found: 635.2.

Step 6: 6-(3-(2-chloro-4-((4-cyclopropyl-1-(2,6-dichloro-4-fluorophenyl)-1H-pyrazol-5-yl)methoxy)phenyl)-3-hydroxyazetidin-1-yl)-5-fluoronicotinic acid (Example 5)

A mixture of methyl 6-(3-(2-chloro-4-((4-cyclopropyl-1-(2,6-dichloro-4-fluorophenyl)-1H-pyrazol-5-yl)methoxy)phenyl)-3-hydroxyazetidin-1-yl)-5-fluoronicotinate (0.35 g, 0.39 mmol) and lithium hydroxide monohydrate (49 mg, 1.2 mmol) were taken up in 1:1 aqueous tetrahydrofuran (6 mL), and the mixture was stirred at room temperature. Upon completion, the mixture was acidified with glacial acetic acid and concentrated. The residue was purified by flash chromatography (silica gel) to provide 6-(3-(2-chloro-4-((4-cyclopropyl-1-(2,6-dichloro-4-fluorophenyl)-1H-pyrazol-5-yl)methoxy)phenyl)-3-hydroxyazetidin-1-yl)-5-fluoronicotinic acid (Example 5). LCMS-ESI+ (m/z): [M+H]+ calcd for $C_{28}H_{22}Cl_3F_2N_4O_4$: 621.1; found: 621.2. 1H NMR (400 MHz, DMSO-d6) δ 12.85 (s, 1H), 8.44 (t, J=1.6 Hz, 1H), 7.76 (d, J=8.3 Hz, 2H), 7.70 (dd, J=12.7, 1.7 Hz, 1H), 7.49 (s, 1H), 7.40 (d, J=8.7 Hz, 1H), 7.00 (d, J=2.6 Hz, 1H), 6.80 (dd, J=8.7, 2.6 Hz, 1H), 6.28 (s, 1H), 5.01 (s, 2H), 4.69 (d, J=9.8 Hz, 2H), 4.34 (d, J=9.6 Hz, 2H), 1.89 (tt, J=8.4, 5.1 Hz, 1H), 0.93 (m, 2H), 0.65 (m, 2H).

Example 6
5-((1S,3S)-3-(2-chloro-4-((5-cyclopropyl-3-(2,6-dichloro-4-fluorophenyl)isoxazol-4-yl)methoxy)phenyl)-3-hydroxycyclobutyl)-6-methoxynicotinic Acid
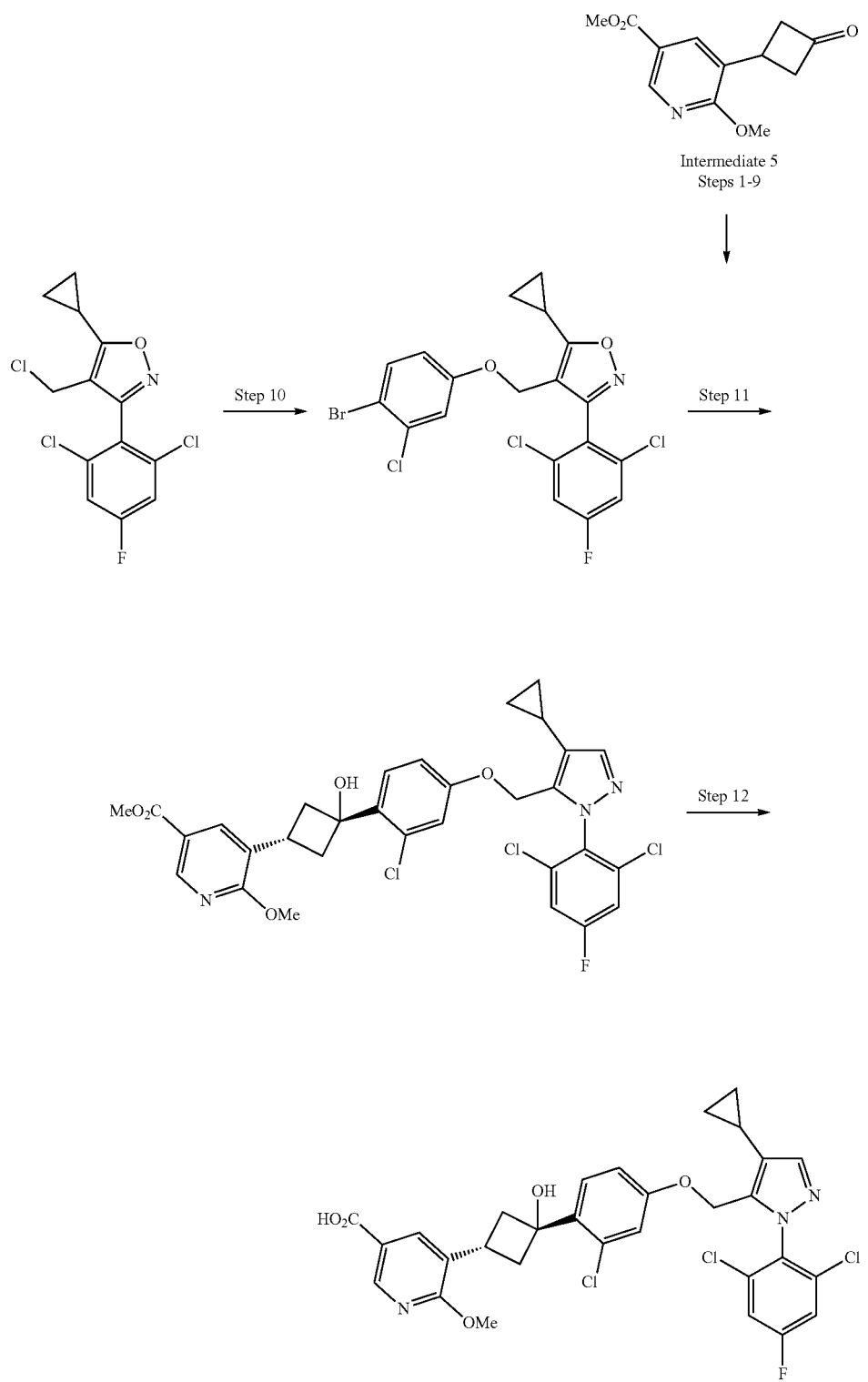

Synthesis of Intermediate 5

Step 1: (5-bromo-6-methoxypyridin-3-yl)methanol

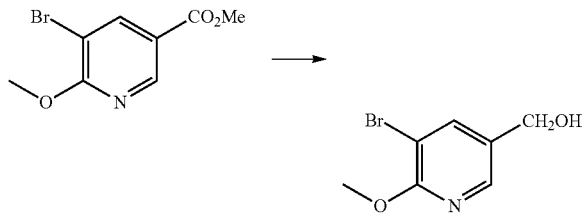

To a solution of methyl 5-bromo-6-methoxynicotinate (52.8 g, 215.0 mmol) in THF (500 mL) was added DIBAL-H (1.0 M, in toluene) (344 ml, 344 mmol) at −20° C. Then the mixture was stirred at RT for 2 h. The mixture was quenched with sat. NH₄Cl and diluted with ethyl acetate. The organic portion was washed with brine, dried over anhydrous sodium sulfate, filtered, concentrated under reduced pressure and purified by flash chromatography on silica gel (PE/EtOAc=4/1) to give the title compound.

Step 2: 3-bromo-5-(((tert-butyldimethylsilyl)oxy)methyl)-2-methoxypyridine

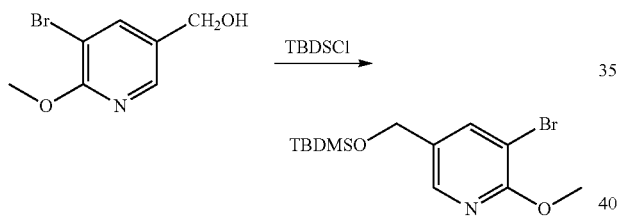

To a solution of (5-bromo-6-methoxypyridin-3-yl)methanol (42.2 g, 194 mmol) and tert-butyldimethylsilyl chloride (35.0 g, 232 mmol) in CH₂Cl₂ (500 ml) was added imidazole (19.8 g, 291 mmol). The mixture was stirred at RT for 8 h. The mixture was quenched with water and diluted with ethyl acetate. The organic portion was washed with brine, dried over anhydrous sodium sulfate, filtered, concentrated under reduced pressure and purified by flash chromatography on silica gel (PE/EtOAc=10/1) to give the title compound.

Step 3: 3-(benzyloxy)-1-(5-(((tert-butyldimethylsilyl)oxy)methyl)-2-methoxypyridin-3-yl)cyclobutan-1-ol

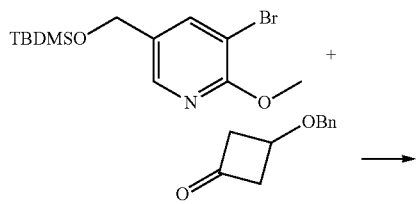

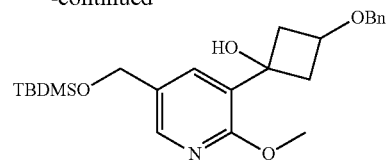

3-bromo-5-(((tert-butyldimethylsilyl)oxy)methyl)-2-methoxypyridine (61.2 g, 184 mmol) was dissolved in absolute THF (500 mL) under argon) a 1.6 M solution of n-butyllithium (138 mL, 221 mmol) in THF was added dropwise at −78° C. The mixture was stirred for 30 min at the same temperature. A solution of 3-(benzyloxy)cyclobutan-1-one (35.7 g, 202 mmol) in THF (100 mL) was then added at −78° C., and the mixture was subsequently stirred at this temperature for 30 min. Saturated aqueous ammonium chloride was subsequently added and the mixture was extracted with ethyl acetate. The organic phase was washed with water and saturated sodium chloride solution, dried over magnesium sulfate and filtered. After removal of the solvent on a rotary evaporator, the residue was purified by flash chromatography on silica gel (PE/EtOAc=2/1) to give the title compound.

Step 4: 3-(benzyloxy)-1-(5-(hydroxymethyl)-2-methoxypyridin-3-yl)cyclobutan-1-ol

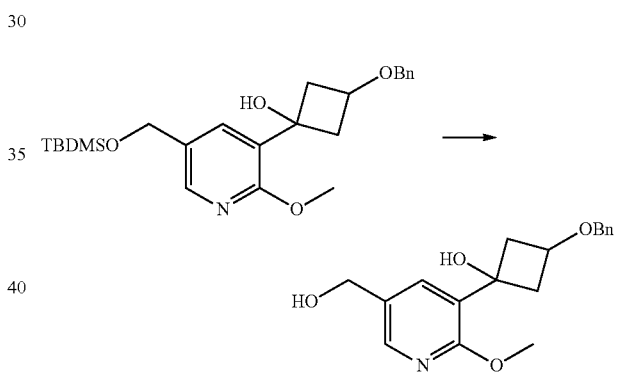

To a solution of 3-(benzyloxy)-1-(5-(((tert-butyldimethylsilyl)oxy)methyl)-2-methoxypyridin-3-yl)cyclobutan-1-ol (31.6 g, 73.6 mmol) in THF (300 mL) was added TBAF (88 mL, 1 mol/L). The mixture was stirred at rt for 6 hours, then poured into water and extracted with ethyl acetate. The organic phase was washed with water and saturated sodium chloride solution, dried over magnesium sulfate and filtered. The organic phase was concentrated to give the title compound.

Step 5: 5-(3-(benzyloxy)-1-hydroxycyclobutyl)-6-methoxynicotinic acid

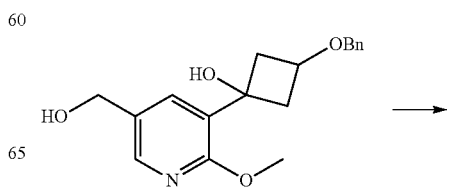

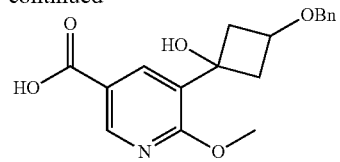

To a solution of 3-(benzyloxy)-1-(5-(hydroxymethyl)-2-methoxypyridin-3-yl)cyclobutan-1-ol (23.2 g, 73.6 mmol) in MeCN (300 mL) and H₂O (100 mL) was added iodobenzene diacetate (64.4 g, 200 mmol) and TEMPO (7.86 g, 50 mmol), and the solution was stirred at room temperature for 2 hrs. The mixture was quenched with sat. sodium bicarbonate solution and diluted with ethyl acetate. The organic portion was washed with brine, dried over anhydrous sodium sulfate, filtered; the organic phase was concentrated to give the title compound.

Step 6: methyl 5-(3-(benzyloxy)-1-hydroxycyclobutyl)-6-methoxynicotinate

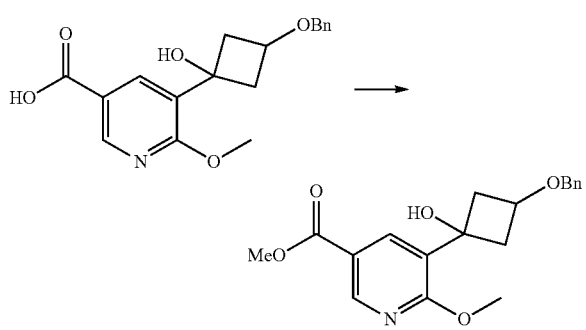

To a solution of 5-(3-(benzyloxy)-1-hydroxycyclobutyl)-6-methoxynicotinic acid (17.5 g, crude) in THF/MeOH (200/50 mL) was added TMSN₂CH₃ (50 mL, 20 mol/L) at 0° C. The mixture was stirred at room temperature for 3 hours, then poured into water and extracted with ethyl acetate. The organic phase was washed with water and saturated sodium chloride solution, dried over magnesium sulfate and filtered. The filtrate was concentrated under reduced pressure and purified by flash chromatography on silica gel (PE/EA=10.1) to give the title compound.

Step 7: methyl 5-(3-(benzyloxy)-1-fluorocyclobutyl)-6-methoxynicotinate

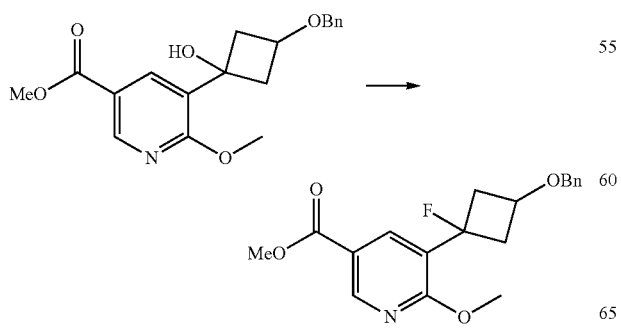

To a cooled solution of methyl 5-(3-(benzyloxy)-1-hydroxycyclobutyl)-6-methoxynicotinate (15.2 g, 44.3 mmol) in DCM (200 mL) was added DAST (8.0 mL) at −78° C. dropwise by syringe. After stirring 5 minutes at −78° C., the reaction was allowed to warm to −20° C. and stirred for 75 minutes, then it was quenched with H₂O (100 mL), diluted with EtOAc and the phases were separated. The organic phase was washed with sat. aq. NaHCO₃ and brine, then dried over MgSO₄, filtered, and concentrated. The crude product was purified by chromatography (PE:EtOAc=4:1) to give the title compound.

Step 8: methyl 5-(3-hydroxycyclobutyl)-6-methoxynicotinate

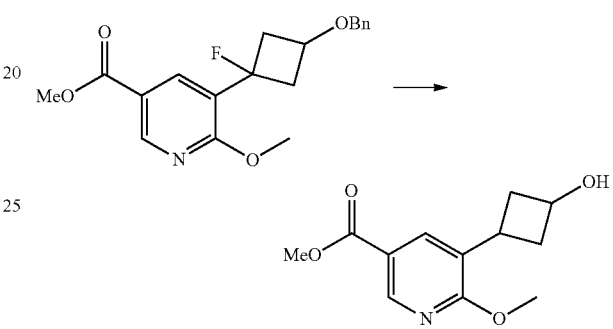

To a solution of methyl 5-(3-(benzyloxy)-1-fluorocyclobutyl)-6-methoxynicotinate (12.7 g, 3.68 mmol) in MeOH (200 mL) and formic acid (10 mL) was added Pd black (3.0 g). The reaction was stirred vigorously under N₂. After about 1.5 hrs, additional Pd black was added (1.5 g) and the reaction stirred overnight. The reaction mixture was filtered and concentrated. The residue was dissolved in EtOAc and washed with sat. Na₂CO₃. The organic phase was dried over MgSO₄, filtered and concentrated to an oily residue. The residue was purified by chromatography (MeOH: CH₂Cl₂=1:20) to give the title compound.

Step 9: methyl 6-methoxy-5-(3-oxocyclobutyl)nicotinate (Intermediate 5)

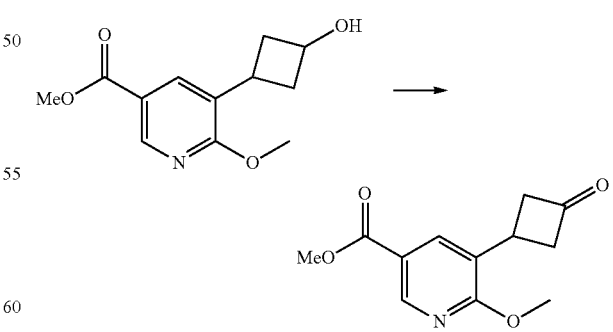

To a solution of methyl 5-(3-hydroxycyclobutyl)-6-methoxynicotinate (4.0 g, 16.9 mmol) in MeCN (100 mL) and H₂O (30 mL) was added iodobenzene diacetate (16.1 g, 50 mmol) and TEMPO (2.92 g, 18.6 mmol), and the solution was stirred at room temperature for 2 hrs. The mixture was quenched with sat. Na$_2$CO$_3$ and then diluted with ethyl acetate. The organic portion was washed with brine, dried over anhydrous sodium sulfate, filtered, and the organic phase was concentrated and purified by chromatography (PE:EA=5:1) to give Intermediate 5.

Step 10: 4-((4-bromo-3-chlorophenoxy)methyl)-5-cyclopropyl-3-(2,6-dichloro-4-fluorophenyl)isoxazole A solution of crude 4-(chloromethyl)-5-cyclopropyl-3-(2, 6-dichloro-4-fluorophenyl)isoxazole (prepared as described in Example 2, step 2; 0.42 g, 1.3 mmol) in N,N-dimethylformamide (DMF, 6 mL) was treated with 4-bromo-3-chlorophenol (0.27 g, 1.3 mmol), sodium iodide (0.34 g, 2.2 mmol), and potassium carbonate (0.37 g, 2.6 mmol). The mixture was heated at 60° C. for 35 minutes before it was cooled and purified by flash chromatography (silica gel) to provide the desired material. LCMS-ESI$^+$ (m/z): [M+H]$^+$ calcd for C$_{19}$H$_{13}$BrCl$_3$FNO$_2$: 491.9; found: 492.0.

Step 11: Methyl 5-(3-(2-chloro-4-((5-cyclopropyl-3-(2,6-dichloro-4-fluorophenyl)isoxazol-4-yl)methoxy)phenyl)-3-hydroxycyclobutyl)-6-methoxynicotinate Under an atmosphere of Argon, a solution of 4-((4-bromo-3-chlorophenoxy)methyl)-5-cyclopropyl-3-(2,6-dichloro-4-fluorophenyl)isoxazole (0.83 g, 1.7 mmmol) in 2-methyltetrahydrofuran (2 mL) was treated with isopropylmagnesium chloride/lithium chloride solution (Aldrich, 1.3 M in tetrahydrofuran, 1.3 mL, 1.7 mmol) dropwise via syringe. After the passage of four hours, an additional volume of isopropylmagnesium chloride/lithium chloride solution (1.3 mL) was added. In a separate vessel, under an atmosphere of Argon, a solution of methyl 6-methoxy-5-(3-oxocyclobutyl) nicotinate (Intermediate 5), 0.21 g, 0.90 mmol) in tetrahydrofuran (5 mL) was treated with lanthanum (III) chloride/2 lithium chloride solution (Aldrich, 0.6 M in tetrahydrofuran, 1.5 mL, 0.9 mmol). This mixture was stirred for one hour at room temperature before it was cooled in a −8° C. wet ice/acetone bath. The Grignard solution from above was added dropwise to the ketone solution via syringe. The reaction mixture was stirred overnight under an Argon atmosphere. The mixture was quenched with saturated aqueous ammonium chloride solution. The aqueous phase was extracted three times with ethyl acetate. The combined organics were washed once with saturated aqueous sodium chloride solution, dried over anhydrous magnesium sulfate, filtered, and concentrated under reduced pressure. The crude residue was purified by flash chromatography (silica gel) to provide the title compound. LCMS-ESI$^+$ (m/z): [M+H]$^+$ calcd for C$_{31}$H$_{27}$Cl$_3$FN$_2$O$_6$: 647.1; found: 647.1.

Step 12: 5-((1S,3S)-3-(2-chloro-4-((5-cyclopropyl-3-(2,6-dichloro-4-fluorophenyl)isoxazol-4-yl)methoxy)phenyl)-3-hydroxycyclobutyl)-6-methoxynicotinic acid (Example 6)

A mixture of methyl 5-(3-(2-chloro-4-((5-cyclopropyl-3-(2,6-dichloro-4-fluorophenyl)isoxazol-4-yl)methoxy)phenyl)-3-hydroxycyclobutyl)-6-methoxynicotinate (0.26 g, 0.40 mmol) and lithium hydroxide monohydrate (33 mg, 0.79 mmol) were taken up in 1:1 aqueous tetrahydrofuran (10 mL) and stirred overnight at room temperature. The volatiles were mostly removed by under reduced pressure. The aqueous mixture was diluted with water and treated dropwise with 10% aqueous hydrochloric acid. The resulting mixture was extracted with ethyl acetate three times. The combined organics were washed with saturated aqueous sodium chloride solution (with a small amount of hydrochloric acid added). The combined organics were dried over anhydrous magnesium sulfate, filtered, and concentrated under reduced pressure. The residue was purified first by flash chromatography (silica gel) and then by preparative HPLC (acetonitrile/water, TFA). The combined fractions collected by HPLC were neutralized with saturated aqueous sodium hydrogen carbonate solution, saturated with sodium chloride, and extracted three times with ethyl acetate. The combined organics were dried over anhydrous magnesium sulfate, filtered, and concentrated. The residue was taken up in ethyl acetate, treated with anhydrous magnesium sulfate, filtered, and concentrated. Again the residue was taken up in ethyl acetate and filtered through a pad of Celite diatomaceous earth. The filtrate was concentrated to provide 5-((1S, 3S)-3-(2-chloro-4-((5-cyclopropyl-3-(2,6-dichloro-4-fluorophenyl)isoxazol-4-yl)methoxy)phenyl)-3-hydroxycyclobutyl)-6-methoxynicotinic acid (Example 6). LCMS-ESI$^+$ (m/z): [M+H]$^+$ calcd for C$_{30}$H$_{25}$Cl$_3$FN$_2$O$_6$: 633.1; found: 633.1. 1H NMR (400 MHz, DMSO-d6) δ 13.00 (bs, 1H), 8.58 (d, J=2.2 Hz, 1H), 8.13 (dd, J=2.3, 0.8 Hz, 1H), 7.72 (d, J=8.5 Hz, 2H), 7.51 (d, J=8.7 Hz, 1H), 6.94 (d, J=2.6 Hz, 1H), 6.79 (dd, J=8.7, 2.6 Hz, 1H), 4.94 (s, 2H), 3.90 (s, 3H), 3.15-3.03 (m, 2H), 2.91 (p, J=8.8 Hz, 1H), 2.49-2.41 (m, 1H), 2.41-2.30 (m, 2H), 1.21-1.09 (m, 4H).

Example 7

2-(6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinamido)ethane-1-sulfonic Acid

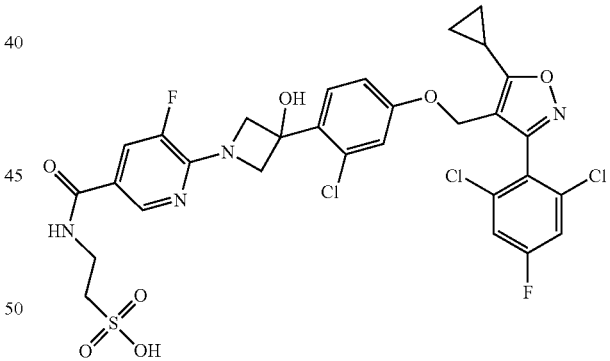

A solution of 6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinic acid (Example 3, 0.11 g, 0.18 mmol) in DMF (4 mL) was treated with HATU (1-[bis(dimethylamino)methylene]-1H-1,2,3-triazolo[4,5-b] pyridinium 3-oxid hexafluorophosphate, 0.10 g, 0.27 mmol) followed by taurine (34 mg, 0.27 mmol) and N,N-diisopropylethylamine (90 μL, 0.54 mmol). The mixture was stirred overnight at room temperature and was then purified by preparative HPLC (water/acetonitrile/TFA). The combined fractions were treated with ammonium hydroxide solution and concentrated to give 2-(6-(3-(2-chloro-4-((5-cyclopropyl-3-(2,6-dichloro-4-fluorophenyl)isoxazol-4-yl)methoxy) phenyl)-3-hydroxyazetidin-1-yl)-5-fluoronicotinamido)ethane-1-sulfonic acid (Example 7) as the ammonium salt. LCMS-ESI$^+$ (m/z): [M+H]$^+$ calcd for $C_{30}H_{26}Cl_3F_2N_4O_7S$: 729.1; found: 729.2. $^1$H NMR (400 MHz, DMSO-d6) δ 8.34 (m, 2H), 7.73-7.61 (m, 3H), 7.37 (d, J=8.6 Hz, 1H), 7.29-6.95 (m, 4H), 6.92 (d, J=2.5 Hz, 1H), 6.75 (dd, J=8.6, 2.5 Hz, 1H), 6.22 (s, 1H), 4.90 (s, 2H), 4.63 (d, J=9.6 Hz, 2H), 4.29 (d, J=9.6 Hz, 2H), 3.46 (q, J=6.5 Hz, 2H), 2.63 (t, J=7.3 Hz, 2H), 2.45-2.38 (m, 1H), 1.16 (dt, J=8.5, 3.1 Hz, 2H), 1.10 (dt, J=5.4, 2.9 Hz, 2H).

Example 8

(6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinoyl)glycine

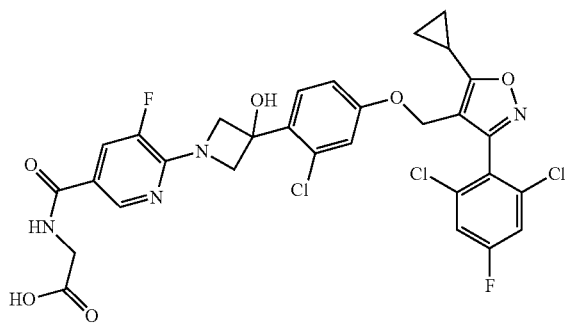 [SMILES: O=C(O)CNC(=O)c1cnc(N2CC(O)(c3ccc(OCc4c(-c5c(Cl)cc(F)cc5Cl)noc4C4CC4)cc3Cl)C2)c(F)c1]

Step 1: methyl (6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinoyl)glycinate A solution of 6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinic acid (Example 3, 0.12 g, 0.19 mmol) in DMF (4 mL) was treated with HATU (1-[bis(dimethylamino)methylene]-1H-1,2,3-triazolo[4,5-b]pyridinium 3-oxid hexafluorophosphate, 0.11 g, 0.29 mmol) followed by glycine methyl ester hydrochloride (36 mg, 0.29 mmol) and N,N-diisopropylethylamine (100 µL, 0.58 mmol). The mixture was stirred overnight at room temperature and was then quenched with saturated aqueous sodium hydrogen carbonate solution. The aqueous phase was extracted twice with ethyl acetate. The combined extracts were washed once with 1:1 saturated aqueous sodium chloride solution/saturated aqueous sodium hydrogen carbonate solution, dried over anhydrous magnesium sulfate, filtered, and concentrated under reduced pressure to give the desired product, which was carried forward without further purification. LCMS-ESr (m/z): [M+H]$^+$ calcd for $C_{31}H_{26}Cl_3F_2N_4O_6$: 693.1; found: 693.2.

Step 2: (6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinoyl)glycine (Example 8)

A mixture of crude methyl (6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinoyl)glycinate (approximately 0.19 mmol) and lithium hydroxide monohydrate (38 mg, 0.91 mmol) in aqueous tetrahydrofuran (2:1, 3 mL) was stirred at room temperature for 3.5 hours. The volatile solvent was removed under reduced pressure. The residue was diluted with water and acidified to pH 1 with 10% aqueous hydrochloric acid. The acidic aqueous mixture was extracted three times with ethyl acetate. The combined organic extracts were washed once with saturated aqueous sodium chloride solution, dried over anhydrous magnesium sulfate, filtered, and concentrated to dryness under reduced pressure. The residue was purified by flash chromatography (silica gel) to provide (6-(3-(2-chloro-4-((5-cyclopropyl-3-(2,6-dichloro-4-fluorophenyl)isoxazol-4-yl)methoxy)phenyl)-3-hydroxyazetidin-1-yl)-5-fluoronicotinoyl)glycine (Example 8). LCMS-ESI$^+$ (m/z): [M+H]$^+$ calcd for $C_{30}H_{24}Cl_3F_2N_4O_6$: 679.1; found: 679.3. $^1$H NMR (400 MHz, DMSO-d6) δ 12.68 (s, 1H), 8.68 (t, J=5.8 Hz, 1H), 8.44 (t, J=1.7 Hz, 1H), 7.80 (dd, J=13.2, 1.8 Hz, 1H), 7.71 (d, J=8.5 Hz, 2H), 7.39 (d, J=8.7 Hz, 1H), 6.95 (d, J=2.5 Hz, 1H), 6.77 (dd, J=8.6, 2.6 Hz, 1H), 6.26 (s, 1H), 4.93 (s, 2H), 4.66 (d, J=9.5 Hz, 2H), 4.32 (d, J=9.3 Hz, 2H), 3.87 (d, J=5.8 Hz, 2H), 2.48-2.42 (partially obscured by DMSO, m, 1H), 1.16 (m, 4H).

Example 9

FRET Activity Assay

Determination of a ligand mediated cofactor peptide interaction to quantify ligand binding to the nuclear receptor FXR was performed as follows.

Preparation of human FXR alpha ligand binding domain: The human FXRalpha LBD was expressed in *E. coli* strain BL21(DE3) as an N-terminally GST tagged fusion protein. The DNA encoding the FXR ligand binding domain was cloned into vector pDEST15 (Invitrogen). Expression was under control of an IPTG inducible T7 promoter. The amino acid boundaries of the ligand binding domain were amino acids 187-472 of Database entry NM_005123 (RefSeq). Expression and purification of the FXR-LBD: An overnight preculture of a transformed *E. coli* strain was diluted 1:20 in LB-Ampicillin medium and grown at 30° C. to an optical density of $OD_{600}$=0.4–0.6. Gene expression was then induced by addition of 0.5 mM IPTG. Cells were incubated an additional 6 h at 30° C., 180 rpm. Cells were collected by centrifugation (7000×g, 7 min, rt). Per liter of original cell culture, cells were resuspended in 10 mL lysis buffer (50 mM Glucose, 50 mM Tris pH 7.9, 1 mM EDTA and 4 mg/mL lysozyme) and left on ice for 30 min. Cells were then subjected to sonication and cell debris removed via centrifugation (22000×g, 30 min, 4° C.). Per 10 mL of supernatant 0.5 mL prewashed Glutathione 4B sepharose slurry (Qiagen) was added and the suspension kept slowly rotating for 1 h at 4° C. Glutathione 4B sepharose beads were pelleted by centrifugation (2000×g, 15 sec, 4° C.) and washed twice in wash buffer (25 mM Tris, 50 mM KCl, 4 mM $MgCl_2$ and 1M NaCl). The pellet was resuspended in 3 mL elution buffer per liter of original culture (elution buffer: 20 mM Tris, 60 mM KCl, 5 mM $MgCl_2$ and 80 mM glutathione added immediately prior to use as powder). The suspension was left rotating for 15 min at 4° C., the beads pelleted and eluted again with half the volume of elution buffer than the first time. The eluates were pooled and dialysed overnight in 20 mM Hepes buffer (pH 7.5) containing 60 mM KCl, 5 mM $MgCl_2$ as well as 1 mM dithiothreitol and 10% (v/v) glycerol. The protein was analysed by SDS-Page.

The method measures the ability of putative ligands to modulate the interaction between the purified bacterial expressed FXR ligand binding domain (LBD) and a synthetic biotinylated peptide based on residues 676-700 of SRC-1 (LCD2, 676-700). The sequence of the peptide used was B-CPSSHSSLTERHKILHRLLQEGSPS-COOH (SEQ ID NO: 1) where the N-terminus was biotinylated (B). The ligand binding domain (LBD) of FXR was expressed as fusion protein with GST in BL-21 cells using the vector pDEST15. Cells were lysed by sonication, and the fusion proteins purified over glutathione sepharose (Pharmacia) according to the manufacturers instructions. For screening of compounds for their influence on the FXR-peptide interaction, the Perkin Elmer LANCE technology was applied. This method relies on the binding dependent energy transfer from a donor to an acceptor fluorophor attached to the binding partner of interest. For ease of handling and reduction of background from compound fluorescence LANCE technology makes use of generic fluorophore labels and time resolved detection Assays were done in a final volume of 25 µL in a 384 well plate, in a Tris-based buffer (20 mM Tris-HCl pH 7.5; 60 mM KCl, 5 mM $MgCl_2$; 35 ng/µL BSA), containing 20-60 ng/well recombinantly expressed FXR-LBD fused to GST, 200-600 nM N-terminally biotinylated peptide, representing SRC1 aminoacids 676-700, 200 ng/well Streptavidin-xlAPC conjugate(Prozyme) and 6-10 ng/well Eu W1024—antiGST (Perkin Elmer). DMSO content of the samples was kept at 1%. After generation of the assay mix and diluting the potentially FXR modulating ligands, the assay was equilibrated for 1 h in the dark at rt in FIA-plates black 384 well (Greiner). The LANCE signal was detected by a Perkin Elmer VICTOR2VTM Multilabel Counter. The results were visualized by plotting the ratio between the emitted light at 665 and 615 nm. A basal level of FXR-peptide formation is observed in the absence of added ligand. Ligands that promote the complex formation induce a concentration-dependent increase in time-resolved fluorescent signal. Compounds which bind equally well to both monomeric FXR and to the FXR-peptide complex would be expected to give no change in signal, whereas ligands which bind preferentially to the monomeric receptor would be expected to induce a concentration-dependent decrease in the observed signal.

To assess the agonistic potential of the compounds, $EC_{50}$ values were determined for example compounds and are listed below in Table 2 (FRET $EC_{50}$).

Example 10

Mammalian One Hybrid (M1H) Assay

Determination of a ligand mediated Gal4 promoter driven transactivation to quantify ligand binding mediated activation of FXR was performed as follows.

The cDNA part encoding the FXR ligand binding domain was cloned into vector pCMV-BD (Stratagene) as a fusion to the yeast GAL4 DNA binding domain under the control of the CMV promoter. The amino acid boundaries of the ligand binding domain were amino acids 187-472 of Database entry NM_005123 (RefSeq). The plasmid pFR-Luc (Stratagene) was used as the reporter plasmid, containing a synthetic promoter with five tandem repeats of the yeast GAL4 binding sites, driving the expression of the Photinus pyralis (American firefly) luciferase gene as the reporter gene. In order to improve experimental accuracy the plasmid pRL-CMV (Promega) was cotransfected. pRL-CMV contains the constitutive CMV promoter, controlling the expression of the Renilla reniformis luciferase. All Gal4 reporter gene assays were done in HEK293 cells (obtained from DSMZ, Braunschweig, Germany) grown in MEM with L-Glutamine and Earle's BSS supplemented with 10% fetal bovine serum, 0.1 mM nonessential amino acids, 1 mM sodium pyruvate, and 100 units Penicilin/Streptavidin per mL at 37° C. in 5% $CO_2$. Medium and supplements were obtained from Invitrogen. For the assay, $5 \times 10^5$ cells were plated per well in 96 well plates in 100 µL per well MEM without Phenol Red and L-Glutamine and with Earle's BSS supplemented with 10% charcoal/dextran treated FBS (HyClone, South Logan, Utah), 0.1 mM nonessential amino acids, 2 mM glutamine, 1 mM sodium pyruvate, and 100 units Penicilin/Streptavidin per mL, incubated at 37° C. in 5% $CO_2$. The following day the cells were >90% confluence. Medium was removed and cells were transiently transfected using 20 µL per well of an OptiMEM—polyethylene-imine-based transfection-reagent (OptiMEM, Invitrogen; Polyethyleneimine, Aldrich Cat No. 40,827-7) including the three plasmids described above. MEM with the same composition as used for plating cells was added 2-4 h after addition of transfection mixture. Then compound stocks, prediluted in MEM were added (final vehicle concentration not exceeding 0.1%). Cells were incubated for additional 16 h before firefly and renilla luciferase activities were measured sequentially in the same cell extract using a Dual-Light-Luciferase-Assay system (Dyer et al., *Anal. Biochem.* 2000, 282, 158-161). All experiments were done in triplicates.

To assess the FXR agonistic potency of the example compounds, potency was determined in the M1H assay and is listed below in Table 2 (M1H $EC_{50}$).

TABLE 2

| Example | FRET $EC_{50}$ (nM) | M1H $EC_{50}$ (nM) |
|---------|---------------------|---------------------|
| 1 | 263 | 3000 |
| 2 | 25 | 831 |
| 3 | 7.4 | 3.8 |
| 4 | 35 | 176 |
| 5 | 18 | 8.6 |
| 6 | 49 | 353 |
| 7 | 6.9 | 1696 |
| 8 | 8.1 | 1264 |

Example 11

Metabolite ID Assay in Human Liver Microsomes

The metabolic stability of Example 3 and Comparative Example 1 in human liver microsmoes was conducted according to the following procedure. Human liver microsomes (35 µL protein concentration 20 mg/mL), 350 µL of 100 mM potassium phosphate buffer (pH 7.4), 245 µL of deionized water and 0.7 µL of compound stock solution (5 mM) were combined in a 1.5 mL microcentrifuge tube. The tube was sealed and gently vortexed for 10 seconds, then placed in an Eppendorf ThermoMixer C and pre-warmed at 37° C. with shaking at 1100 rpm for 5 minutes.

NADPH solution (70 µL; 10 mM in water) was added while shaking, the mixture was aspirated several times with pipet, and 200 µL was removed to a fresh 1.5 mL microcentrifuge tube on ice containing 200 µL of cold acetonitrile. This aliquot was vortexed at high speed for 10 seconds then placed on ice. After 30 and 60 minutes additional 200 µl aliquots were removed and transferred to fresh 1.5 mL microcentrifuge tube on ice containing 200 µL of cold acetonitrile. These were vortexed at high speed for 10 seconds then placed on ice.

The chilled aliquots were centrifuged at 14,300 rpm in a microcentrifuge for 10 minutes at 10° C., then the supernatant was transferred to a deepwell (1 mL) 96 well plate and sealed with a silicon mat. The sample was transferred to the Cool Stack of the autoinjector (temperature set to 10° C.) and 20 µL was injected into the Thermo Elite Orbitrap mass spectrometer. 20 µL samples were analyzed by UPLC-MS in order to identify and quantify the metabolites (Agilent 1290 G4220 binary pump UPLC with Agilent G1316 TCC column oven; Waters Acquity UPLC BEH C18 (130 Å pore size, 1.7 µm particle size, 2.1×50 mm) column held at 40° C.; Agilent 1290 G4212 DAD diode array with wavelength range 190 to 400 nm; Thermo Electron Orbitrap Elite mass spectrometer in FTMS positive mode).

Final microsomal protein concentration: 1 mg/mL

Final NADPH concentration: 1 mM

Final substrate concentration: 5 µM

Time points: 0, 30, 60 minutes

Incubation volume per time point: 200 µL

Comparative Example 1, a direct comparator to Example 3 that lacks a 4-fluorophenyl substituent present in the compounds disclosed herein, was found to be metabolized to a diol compound (M1) under the conditions described above (Scheme 1). Incorporation of the 4-fluoro substituent inhibited formation of metabolite M1 under the same conditions.

Scheme 1

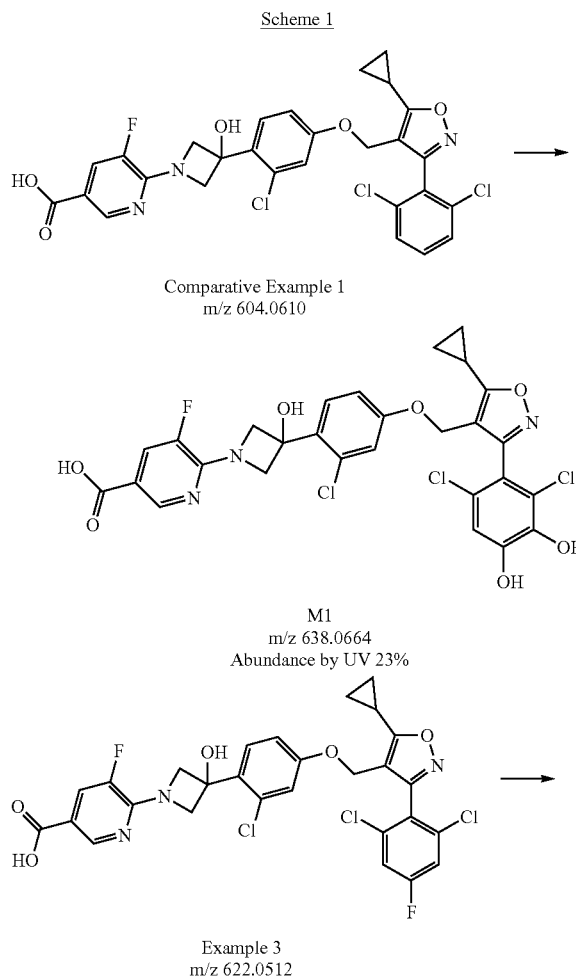

Comparative Example 1
m/z 604.0610

M1
m/z 638.0664
Abundance by UV 23%

Example 3
m/z 622.0512

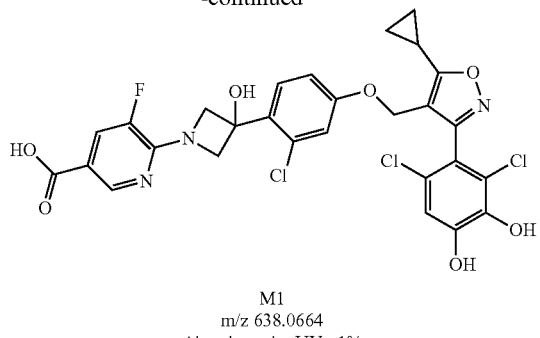

M1
m/z 638.0664
Abundance by UV <1%

Example 12

Assessment of In Vivo Pharmacodynamics in Cynomolgus Monkey

In vivo pharmacodynamics of a representative compound of Formula (I) and a comparative example compound were determined as follows.

Test Article and Formulation

Oral suspension doses of a representative compound of Formula (I) (Example 3) and Comparative Example 2 (Example 13/9 of U.S. Pat. No. 9,139,539) were formulated at concentrations of 2, 6, 20, and 60 mg/mL in aqueous suspensions of 0.5% sodium carboxymethylcellulose (Na CMC), 1% ethanol, and 98.5% 50 mM Tris buffer, at pH 8.

Animals

Each dosing group consisted of three male Cynomolgus monkeys. At dosing, the animals weighed between 2.5 and 4.4 kg.

Dosing

The test articles were administered to the monkeys via oral gavage at 5 mL/kg. Prior to withdrawal, the gavage tube was flushed with approximately 10 mL of water.

Sample Collection

Venous blood samples were taken at specified time points after dosing from each animal. The blood samples were collected and transferred into tubes containing potassium ($K_2$) EDTA anticoagulant.

Determination of FGF19 Concentrations in Plasma

The FGF19 ELISA assay kit from BioVendor (product number RD191107200R) was used to determine FGF19 concentrations in the collected blood samples.

Determination of Drug Concentratsion in Plasma

An aliquot of 50 µL of each plasma sample from the 10 and 30 mg/kg dosing groups and the t=0 samples from the 100 and 300 mg/kg groups were treated with 200 µL of acetonitrile (ACN) containing internal standard. An aliquot of 25 µL of the remaining samples from the 100 mg/kg group was combined with 25 µL of blank plasma to effect a 1:2 dilution and treated with 200 µL of acetonitrile (ACN) containing internal standard. An aliquot of 10 µL of the remaining samples from the 300 mg/kg group was combined with 40 µL of blank plasma to effect a 1:5 dilution and treated with 200 µL of acetonitrile (ACN) containing internal standard. The above solutions were centrifuged at 5000 RPM for 10 minutes and 50 µL of supernatant was transferred to a clean 96-well plate, followed by the addition of 200 µL of water. An aliquot of 10 µL was injected to the API 5000 LC/MS/MS system. Samples exceeding the calibration range of the instrument were diluted and re-analyzed.

HPLC Conditions

A Zorbax Extend C18 HPLC column (50×2.1 mm, 3.5μ) from Agilent Technologies (Part #735700-902) was used. Mobile phase A contained an aqueous solution of 1% acetonitrile in 10 mM ammonium formate adjusted to pH 3.0 with formic acid. Mobile phase B contained and 10% 10 mM ammonium formate in acetonitrile adjusted to pH 5.2 with formic acid. A Thermo Aria multiplexer with two identical Agilent 1200 series binary pumps (P/N G1312A Bin Pump) was used for elution and separation. The elution program used is set forth in the following Table 3.

TABLE 3

| Time (sec) | Step Comments | Flow Rate (mL/min) | Mobile Phase A (%) | Mobile Phase B (%) |
|---|---|---|---|---|
| 30 | Sample Loading | 0.50 | 85 | 15 |
| 180 | Ramp | 0.50 | 50 | 50 |
| 90 | Ramp | 0.50 | 99 | 1 |
| 60 | Elution | 0.50 | 99 | 1 |
| 120 | Re-equilibrium | 0.50 | 85 | 15 |

An API 5000 triple quadrupole mass spectrometer from AB Sciex, Foster City, Calif. was used in multiple reaction monitoring mode to quantify the compounds. The mass spectrometry parameters used are set forth in the following Table 4.

TABLE 4

| Ion source | Spray voltage (V) | Gas 1 (Arb) | Gas 2 (Arb) | Collision gas (Arb) | Dryer temperature (° C.) |
|---|---|---|---|---|---|
| Turbo Ion Spray | 5500 | 70 | 50 | 6 | 550 |

Results

Figure 2:
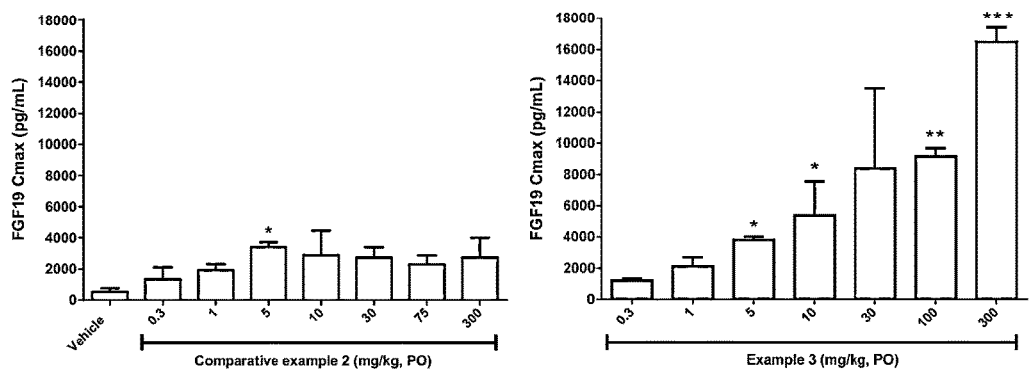
FIG. 2: FGF19 levels generated in cynomolgus monkey with increasing oral doses of Example 3 and Comparative Example 2.

FGF19 levels were compared following oral administration of increasing doses of Example 3 or Comparative Example 2 (3 to 300 mg/kg). Dose-dependent increases in plasma exposure were observed for both compounds and the maximal AUC achieved with each compound at 300 mg/kg were comparable (FIG. 1). Example 3 dose-dependently increased plasma FGF19, reaching a $C_{max}$ of 16000 pg/ml at the highest dose (FIG. 2). Administration of Comparative Example 2 also caused increases in plasma FGF19, but the maximal level of FGF19 was significantly lower ($C_{max}$ 3000 ng/ml) than for Example 3. Furthermore, maximal FGF19 induction by Comparative Example 2 was achieved at 5 mg/kg; higher doses provided no further increase despite greater plasma drug exposures (FIG. 2). This Example demonstrates that IV or oral administration of Example 3 can induce greater FGF19 levels than Comparative Example 2.

Unless otherwise defined, all technical and scientific terms used herein have the same meaning as commonly understood by one of ordinary skill in the art to which this disclosure belongs.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method of treating a patient suffering from Primary Biliary Cirrhosis (PBC) or Primary Sclerosing Cholangitis (PSC) comprising administering to the patient a compound having the structure of Formula (Ia):

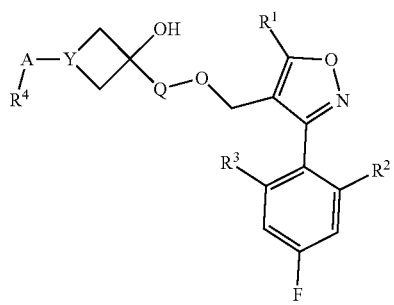

(Ia)

wherein:

Q is phenylene substituted with one chloro;

Y is N;

$R^1$ is cyclopropyl or methyl;

$R^2$ and $R^3$ are chloro;

$R^4$-A is:

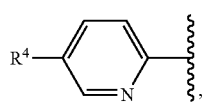

wherein the pyridylene is optionally substituted with one or two groups independently selected from halogen, $C_{1-4}$-alkoxy, halo-$C_{1-4}$-alkoxy, $C_{1-4}$-alkyl, and halo-$C_{1-4}$-alkyl, and $R^4$ is —$CO_2R^5$ or —C(O)$NR^5R^6$;

$R^5$ is hydrogen; and $R^6$ is $C_{1-2}$-alkyl optionally substituted with —$CO_2H$ or —$SO_3H$;

or a pharmaceutically acceptable salt, a stereoisomer, a mixture of stereoisomers, or a tautomer thereof.

2. The method of claim 1, wherein A is pyridylene substituted with one fluoro.

3. The method of claim 1, wherein A is unsubstituted pyridylene.

4. The method of claim 1, wherein $R^4$ is —$CO_2R^5$.

5. The method of claim 1, wherein $R^4$ is —C(O)$NR^5R^6$.

6. The method of claim 1, wherein $R^4$-A is:

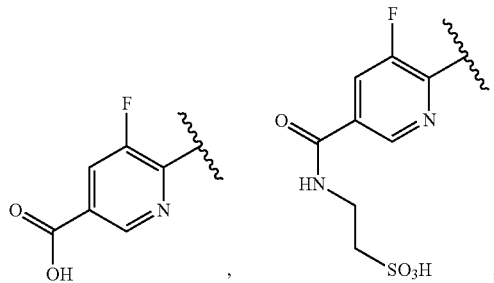

7. The method of claim 1, wherein the compound is selected from the group consisting of:

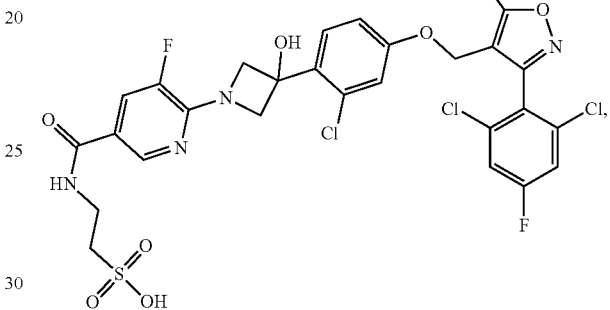

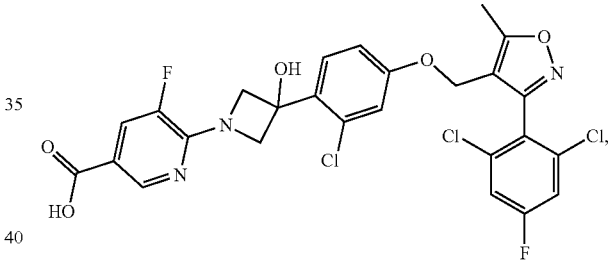

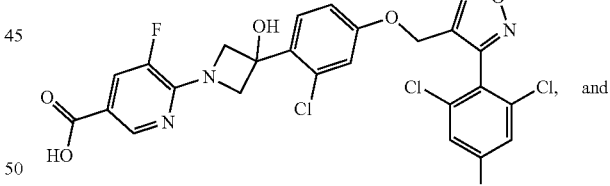

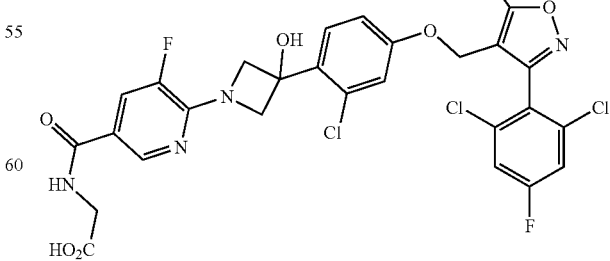

or a pharmaceutically acceptable salt, a stereoisomer, a mixture of stereoisomers, or a tautomer thereof.

8. The method of claim 1, wherein the compound is of the following formula:

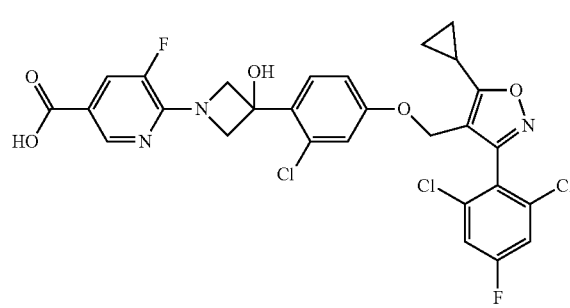

or a pharmaceutically acceptable salt, a stereoisomer, a mixture of stereoisomers, or a tautomer thereof.

9. A method of treating a patient suffering from Primary Biliary Cirrhosis (PBC) or Primary Sclerosing Cholangitis (PSC) comprising administering to the patient a compound having the structure of Formula (Ia):

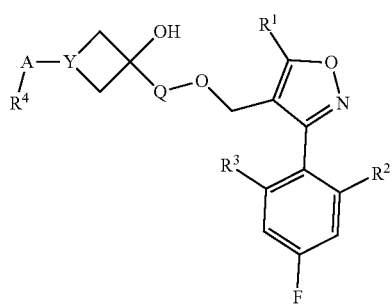

wherein:
Q is phenylene substituted with one chloro;
Y is N;
$R^1$ is cyclopropyl or methyl;
$R^2$ and $R^3$ are chloro;
$R^4$-A is:

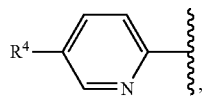

wherein the pyridylene is optionally substituted with one or two groups independently selected from halogen, $C_{1-4}$-alkoxy, halo-$C_{1-4}$-alkoxy, $C_{1-4}$-alkyl, and halo-$C_{1-4}$-alkyl, and $R^4$ is —$CO_2R^5$ or —$C(O)NR^5R^6$;
$R^5$ is hydrogen; and
$R^6$ is $C_{1-2}$-alkyl optionally substituted with —$CO_2H$ or —$SO_3H$;
or a pharmaceutically acceptable salt thereof.

10. The method of claim 9, wherein A is pyridylene substituted with one fluoro.

11. The method of claim 9, wherein A is unsubstituted pyridylene.

12. The method of claim 9, wherein $R^4$ is —$CO_2R^5$.

13. The method of claim 9, wherein $R^4$ is —$C(O)NR^5R^6$.

14. The method of claim 9, wherein $R^4$-A is:

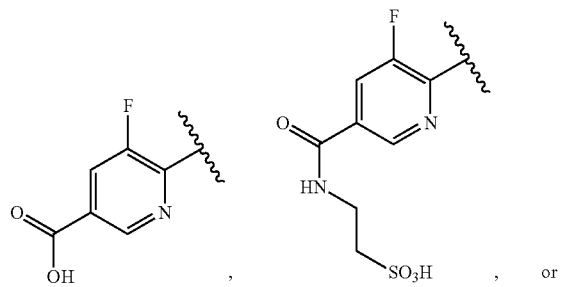

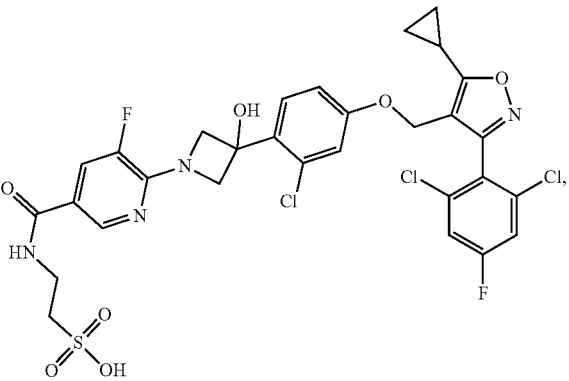

15. The method of claim 9, wherein the compound is selected from the group consisting of:

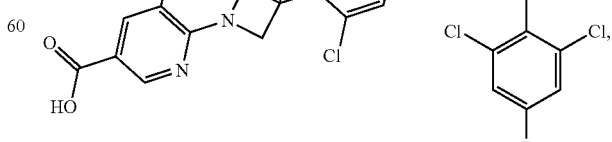

-continued
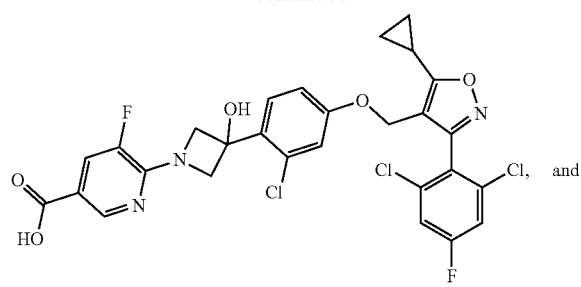
and
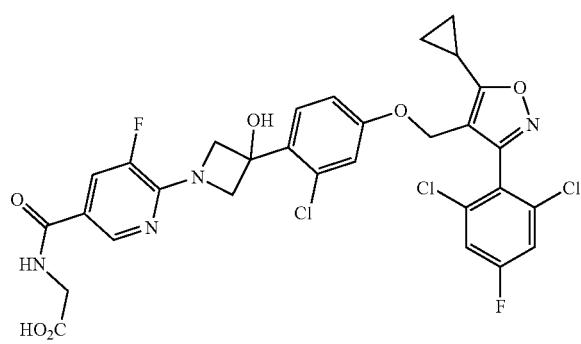
or a pharmaceutically acceptable salt thereof.
16. The method of claim 9, wherein the compound is of the following formula:
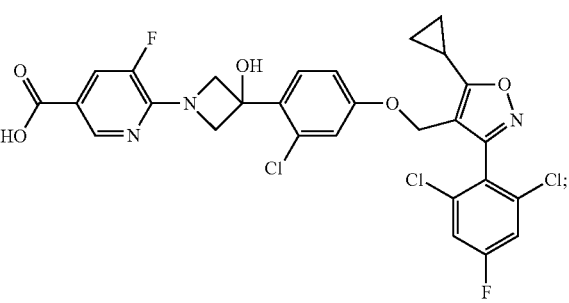 [SMILES: O=C(O)c1cnc(N2CC(O)(c3ccc(OCc4c(-c5c(Cl)cc(F)cc5Cl)noc4C4CC4)cc3Cl)C2)c(F)c1]
or a pharmaceutically acceptable salt thereof.
17. The method of claim 9, wherein the compound is of the following formula:
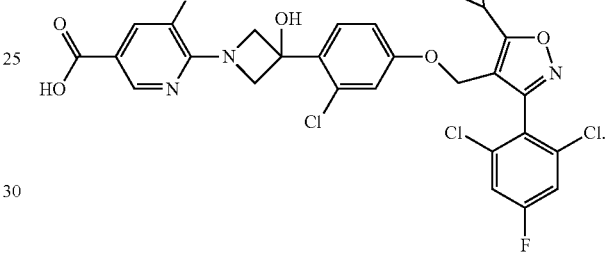
* * * * *